US006566367B2

(12) United States Patent
Bakthavatchalam et al.

(10) Patent No.: US 6,566,367 B2
(45) Date of Patent: May 20, 2003

(54) SPIRO[ISOBENZOFURAN-1,4'-PIPERIDIN]-3-ONES AND 3H-SPIROISOBENZOFURAN-1,4'-PIPERIDINES

(75) Inventors: Rajagopal Bakthavatchalam, Branford, CT (US); Charles A. Blum, Westbrook, CT (US); Harry L. Brielmann, Guilford, CT (US); James William Darrow, Wallingford, CT (US); Stéphane De Lombaert, Madison, CT (US); Alan Hutchison, Madison, CT (US); Jennifer Tran, Guilford, CT (US); Xiaozhang Zheng, Branford, CT (US); Richard Louis Elliott, East Lyme, CT (US); Marlys Hammond, Salem, CT (US)

(73) Assignees: Pfizer Inc., New York, NY (US); Neurogen Corporation, Branford, CT (US)

( * ) Notice: Subject to any disclaimer, the term of this patent is extended or adjusted under 35 U.S.C. 154(b) by 0 days.

(21) Appl. No.: 10/013,846

(22) Filed: Dec. 11, 2001

(65) Prior Publication Data

US 2003/0036652 A1 Feb. 20, 2003

Related U.S. Application Data

(60) Provisional application No. 60/254,990, filed on Dec. 12, 2000.

(51) Int. Cl.$^7$ ........................ C07D 471/10; A61K 31/44
(52) U.S. Cl. ..................... 514/278; 546/17; 546/199
(58) Field of Search .................. 546/199, 17; 514/278

(56) References Cited

U.S. PATENT DOCUMENTS 5,602,024 A   2/1997   Gerald et al. ............... 435/325

FOREIGN PATENT DOCUMENTS

| WO | 0027845 | 5/2000 |
| WO | 0114376 | 3/2001 |
| WO | 0123387 | 4/2001 |
| WO | 0195856 | 12/2001 |
| WO | 2002048152 | * 6/2002 |

OTHER PUBLICATIONS

Michel, Martin C., et al. "XVI. International Union of Pharmacology Recommendations for the Nomenclature of Neuropeptide Y, . . . " Pharmacological Reviews, vol. 50, No. 1 (1998) pp 143–150.

* cited by examiner

Primary Examiner—D. Margaret Seaman
Assistant Examiner—Rita Desai
(74) Attorney, Agent, or Firm—Ladas & Parry

(57) ABSTRACT

Substituted spiro[isobenzofuran-1,4'-piperidin]-3-ones and 3H-spiroisobenzofuran-1,4'-piperidines capable of modulating NPY5 receptor activity are provided. Such compounds may be used to modulate ligand binding to NPY5 receptors in vivo or in vitro, and are particularly useful in the treatment of a variety of disorders (e.g., eating disorders such as obesity or bulimia, psychiatric disorders, diabetes and cardiovascular disorders such as hypertension) in humans, domesticated companion animals and livestock animals. Pharmaceutical compositions and methods for treating such disorders are provided, as are methods for using such compounds for detecting NPY5 receptors.

23 Claims, No Drawings

SPIRO[ISOBENZOFURAN-1,4'-PIPERIDIN]-3-ONES AND 3H-SPIROISOBENZOFURAN-1,4'-PIPERIDINES

This application claims benefit of Provisional Appln No. 60/254,990 filed Dec. 12, 2000.

FIELD OF THE INVENTION

This invention relates generally to substituted spiro [isobenzofuran-1,4'-piperidin]-3-ones and 3H-spiroisobenzofuran-1,4'-piperidines that are modulators of mammalian neuropeptide $Y_5$ (NPY5) receptors, and to the use of such compounds for treating a variety of physiological disorders associated with NPY5 receptor activation, such as feeding disorders, psychiatric disorders and cardiovascular diseases. The invention further relates to the use such compounds as probes for the detection and localization of NPY5 receptors.

BACKGROUND OF THE INVENTION

Neuropeptide Y (NPY) is a 36 amino acid peptide that mediates a variety of physiological effects in humans and other mammals. This is largely conserved across mammalian species, and belongs to a large family of peptides that includes, among others, peptide YY (PYY) and pancreatic peptide (PP). NPY is the most abundant peptide in the mammalian brain, and is also present in sympathetic neurons. In addition, NPY-containing fibers have been found in peripheral tissues, such as around the arteries in the heart, the respiratory tract, the gastrointestinal tract and the genitourinary tract. Central injection of NPY elicits a multitude of physiological responses, such as stimulation of feeding, increase in fat storage, elevation of blood sugar and insulin, anxiolytic behaviors, reduction in locomotor activity, hormone release, increase in blood pressure, reduction in body temperature and catalepsy. In the cardiovascular system, NPY appears to be involved in the regulation of coronary tone. These effects are selectively mediated by various NPY receptors, which currently include the $Y_1$, $Y_2$, $Y_3$, $Y_4$, $Y_5$ and $Y_6$ subtypes, as well as the hypothetical $Y_{1\text{-}like}$ subtype (e.g., Wahlestedt and Reis (1993) *Ann. Rev. Pharmacol. Toxicol.* 33:309; Gehlert and Hipskind (1995) *Curr. Pharm. Design*, 1:295; Michel et al. (1998) *Pharmacol. Rev.* 50:143).

The $Y_5$ receptor subtype (e.g. U.S. Pat. No. 5,602,024) appears to be involved in appetite regulation, including the modulation of food intake and energy expenditure. In addition, studies of seizure-prone mice have suggested that the $NPY_5$ receptor may have an anti-epileptic activity in the control of limbic seizures. $NPY_5$-like receptors have also been implicated in attenuation of morphine withdrawal symptoms, enhancement of diuresis and natriuresis, lowering of blood glucose, inhibition of luteinizing hormone secretion, and reduction of acetylcholine release in the ileum.

Selective peptide agonists and antagonists have been identified for most of the NPY receptor subtypes. Peptides, however, generally have serious shortcomings for therapeutic use including, poor metabolic stability, low oral bioavailability and poor brain permeability. To date, few non-peptide antagonists have been reported. WO 01/14376 describes certain spiro NPY receptor antagonists, but additional antagonists with improved properties are needed as therapeutic agents for the treatment of physiological disorders associated with NPY5 receptor activation, such as feeding disorders (e.g., obesity and bulemia), psychiatric disorders, diabetes and cardiovascular diseases (such as hypertension).

The present invention fulfills this need, and provides further related advantages.

SUMMARY OF THE INVENTION

The present invention provides NPY5 receptor modulators that inhibit or enhance NPY binding to NPY5 receptor. Such modulators generally comprise a substituted spiro [isobenzofuran-1,4'-piperidin]-3-one or 3H-spiroisobenzofuran-1,4'-piperidine characterized by one of the following formulas (or a pharmaceutically acceptable salt or prodrug thereof):

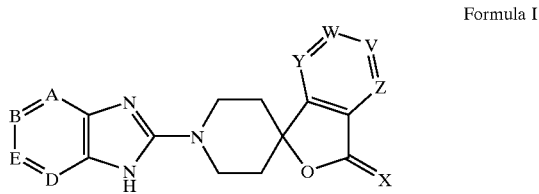

Formula I

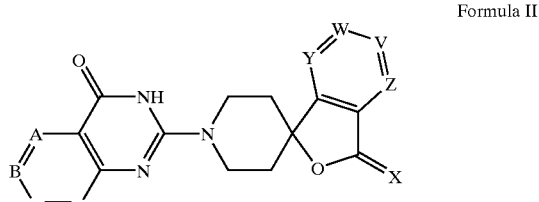

Formula II

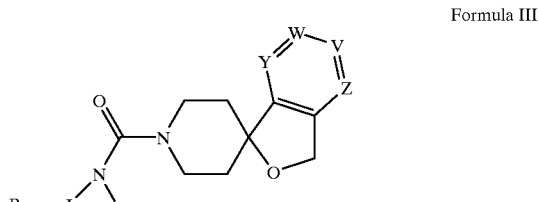

Formula III

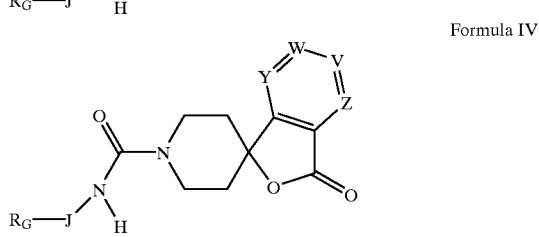

Formula IV

Within Formulas I and II, X is oxygen or $H_2$; A, D, V, W, Y and Z are each independently N or $CR_1$; B is N or $CR_2$; and E is N or $CR_3$. $R_1$ is independently selected at each occurrence from hydrogen, halogen, hydroxy, amino, nitro, cyano, —C(=O)$NH_2$, —COOH and groups of the formula L—$R_A$—Q—G. Within the formula L—$R_A$—Q—G, L is a bond, —O—, —C(=O)—, —OC(=O)—, —C(=O)O—, —O—C(=O)O—, —S(O)$_n$—, —$NR_B$—, —C(=O) $NHR_B$—, —$NHR_B$C(=O)—, —$NR_B$S(O)$_n$— or —S(O)$_n$ $NR_B$—. n is independently chosen at each occurrence from 0, 1 or 2. $R_A$ is ($C_1$–$C_8$)alkyl, ($C_2$–$C_8$)alkenyl, ($C_2$–$C_8$) alkynyl, ($C_3$–$C_8$)cycloalkyl, ($C_3$–$C_8$)cycloalkenyl, ($C_3$–$C_8$) cycloalkynyl or ($C_3$–$C_8$)heterocycloalkyl, each of which is optionally substituted with from 1 to 5 substituents independently selected from hydroxy, halogen, amino, cyano, nitro, ($C_1$–$C_6$)alkyl and halo($C_1$–$C_6$)alkyl. Q is a bond, —O—, —C(=O)—, —OC(=O)—, —C(=O)O—, —O—C(=O)O—, —S(O)n—, —$CHR_B$—, —$NR_B$—, —C(=O)$NHR_B$—, —$NHR_B$C(=O)—, —$NR_B$S(O)$_n$— or —S(O)$_n$$NR_B$. $R_B$ is independently selected at each occurrence from hydrogen, ($C_1$–$C_8$)alkyl, ($C_3$–$C_8$)cycloalkyl, $(C_3-C_8)$cycloalkyl$(C_1-C_8)$alkyl and $(C_1-C_8)$alkyl$(C_3-C_8)$cycloalky. G is: (i) hydrogen; or (ii) $(C_1-C_8)$alkyl, $(C_2-C_8)$alkenyl, $(C_2-C_8)$alkynyl, $(C_3-C_8)$cycloalkyl$(C_1-C_8)$alkyl, or a 3- to 10-membered carbocyclic or heterocyclic group, each of which is optionally substituted with from 1 to 5 substituents independently selected from hydroxy, halogen, amino, cyano, nitro, $(C_1-C_8)$alkyl, halo$(C_1-C_8)$alkyl, $(C_1-C_8)$alkoxy, —NH$(C_1-C_8)$alkyl, —N$(C_1-C_8)$alkyl)$_2$, —NHC(=O)$(C_1-C_8)$alkyl, —N$(C_1-C_8)$alkylC(=O)(alkyl), —NHS(O)s$(C_1-C_8)$alkyl, —S(O)$_s$$(C_1-C_8)$alkyl, —S(O)$_s$NH$(C_1-C_8)$alkyl and —S(O)$_s$N$(C_1-C_8)$alkyl)$_2$, wherein s is 0, 1 or 2.

Within certain embodiments, $R_1$ is independently selected at each occurrence from hydrogen, halogen, hydroxy, nitro, cyano, amino, $(C_1-C_6)$alkyl, $(C_1-C_6)$alkoxy, $(C_3-C_7)$cycloalkyl, $(C_3-C_7)$cycloalkyl$(C_1-C_4)$alkyl, $(C_2-C_6)$alkenyl, $(C_3-C_7)$cycloalkenyl, $(C_2-C_6)$alkynyl, $(C_3-C_7)$cycloalkynyl, halo$(C_1-C_6)$alkyl, halo$(C_1-C_6)$alkoxy, mono and di$(C_1-C_6)$alkylamino, amino$(C_1-C_6)$alkyl, and mono- and di$(C_1-C_6)$alkylamino$(C_1-C_6)$alkyl.

$R_2$ and $R_3$ are independently selected at each occurrence from hydrogen, halogen, hydroxy, amino, nitro, cyano, —C(=O)NH$_2$, —COOH; and groups of the formula T—$R_C$—U—M. Within the formula T—$R_C$—U—M, T is a bond, —O—, —C(=O)—, —OC(=O)—, —C(=O)O—, —O—C(=O)O—, —S(O)$_n$—, —NR$_D$—, —C(=O)NHR$_D$—, —NHR$_D$C(=O)—, —NR$_D$S(O)$_n$— or —S(O)$_n$NR$_D$—. n is independently chosen at each occurrence from 0, 1 or 2. $R_c$ is $(C_1-C_8)$alkyl, $(C_2-C_8)$alkenyl, $(C_2-C_8)$alkynyl or a 3- to 10-membered carbocyclic or heterocyclic group, each of which is optionally substituted with from 1 to 5 substituents independently selected from hydroxy, halogen, amino, cyano, nitro, $(C_1-C_6)$alkyl and halo$(C_1-C_6)$alkyl. U is a bond, —O—, —C(=O)—, —OC(=O)—, —C(=O)O—, —O—C(=O)O—, —S(O)$_n$—, —CHR$_D$—, —NR$_D$—, —C(=O)NHR$_D$—, —NHR$_D$C(=O)—, —NR$_D$S(O)$_n$— or —S(O)$_n$NR$_D$—. $R_D$ is independently selected at each occurrence from hydrogen, $(C_1-C_8)$alkyl, $(C_3-C_8)$cycloalkyl, $(C_3-C_8)$cycloalkyl$(C_1-C_8)$alkyl and $(C_1-C_8)$alkyl$(C_3-C_8)$cycloalkyl. M is: (i) hydrogen; or (ii) $(C_1-C_8)$alkyl, $(C_2-C_8)$alkenyl, $(C_2-C_8)$alkynyl or a 3- to 10-membered carbocyclic or heterocyclic group, each of which is optionally substituted with from 1 to 5 substituents independently selected from hydroxy, halogen, amino, cyano, nitro, $(C_1-C_8)$alkyl, halo$(C_1-C_8)$alkyl, $(C_1-C_8)$alkoxy, —NH$(C_1-C_8)$alkyl, —N$(C_1-C_8)$alkyl)$_2$, —NHC(=O)$(C_1-C_8)$alkyl, —N$(C_1-C_8)$alkylC(=O)(alkyl), —NHS(O)$_s$$(C_1-C_8)$alkyl, —S(O)$_s$$(C_1-C_8)$alkyl, —S(O)$_s$NH$(C_1-C_8)$alkyl and —S(O)$_s$N$(C_1-C_8)$alkyl)$_2$, wherein s is 0, 1 or 2.

Within certain embodiments, $R_2$ and $R_3$ are independently selected from: (i) hydrogen and halogen; and (ii) T—$R_c$, wherein T is a bond, —O—, —C(=O)—, —OC(=O)—, —C(=O)O— or —S(O)$_2$—; and $R_c$ is $(C_1-C_6)$alkyl or a 5- to 6-membered carbocyclic or heterocyclic ring, each of which is optionally substituted as described above.

Within Formulas III and IV, positions designated V, W, Y and Z are as described above, and J is a bond or $(C_1-C_6)$alkyl. Within Formula IV, if $R_G$, M or both are aromatic, then J is $(C_1-C_6)$alkyl.

$R_G$ of Formulas III and IV is $(C_1-C_8)$alkyl, $(C_2-C_8)$alkenyl, $(C_2-C_8)$alkynyl or a 3- to 10-membered carbocyclic or heterocyclic group, each of which is optionally substituted with from 1 to 5 substituents independently selected from: (i) hydrogen, halogen, hydroxy, amino, nitro, cyano, —C(=O)NH$_2$ and —COOH; and (ii) groups of the formula T—$R_C$—U—M. Within the formula T—$R_C$—U—M, T is a bond, —O—, —C(=O)—, —OC(=O)—, —C(=O)O—, —O—C(=O)O—, —S(O)$_n$—, —NR$_D$—, —C(=O)NHR$_D$—, —NHR$_D$C(=O)—, —NR$_D$S(O)$_n$— or —S(O)$_n$NR$_D$—. n is independently chosen at each occurrence from 0, 1 or 2. $R_C$ is $(C_1-C_8)$alkyl, $(C_2-C_8)$alkenyl, $(C_2-C_8)$alkynyl or a 3- to 10-membered carbocyclic or heterocyclic group, each of which is optionally substituted with from 1 to 5 substituents independently selected from hydroxy, halogen, amino, cyano, nitro, $(C_1-C_6)$alkyl and halo$(C_1-C_6)$alkyl. U is a bond, —O—, —C(=O)—, —OC(=O)—, —C(=O)O—, —O—C(=O)O—, —S(O)$_n$—, —CHR$_D$—, —NR$_D$—, —C(=O)NHR$_D$—, —NHR$_D$C(=O)—, —NR$_D$S(O)$_n$— or —S(O)$_n$NR$_D$—. $R_D$ is independently selected at each occurrence from hydrogen, $(C_1-C_8)$alkyl, $(C_3-C_8)$cycloalkyl, $(C_3-C_8)$cycloalkyl$(C_1-C_8)$alkyl and $(C_1-C_8)$alkyl$(C_3-C_8)$cycloalkyl. M is: (i) hydrogen; or (ii) $(C_1-C_8)$alkyl, $(C_2-C_8)$alkenyl, $(C_2-C_8)$alkynyl, $(C_3-C_8)$cycloalkyl$(C_1-C_8)$alkyl or a 3- to 10-membered carbocyclic or heterocyclic group, each of which is optionally substituted with from 1 to 9 substituents independently selected from hydroxy, halogen, amino, cyano, nitro, $(C_1-C_8)$alkyl, $(C_3-C_8)$cycloalkyl, halo$(C_1-C_8)$alkyl, $(C_1-C_8)$alkoxy, —NH$(C_1-C_8)$alkyl, —N$(C_1-C_8)$alkyl)$_2$, —NHC(=O)$(C_1-C_8)$alkyl, —N$(C_1-C_8)$alkylC(=O)(alkyl), —NHS(O)$_s$$(C_1-C_8)$alkyl, —S(O)$_s$$(C_1-C_8)$alkyl, —S(O)$_s$NH$(C_1-C_8)$alkyl and —S(O)$_s$N$(C_1-C_8)$alkyl)$_2$, wherein s is 0, 1 or 2.

Within certain embodiments of Formula III, $R_G$ is: (i) $(C_1-C_6)$alkyl, $(C_2-C_6)$alkenyl or $(C_2-C_6)$alkynyl, each of which is optionally substituted with from 1 to 5 substituents independently selected from hydroxy, halogen, amino, cyano and nitro; or (ii) a 3- to 10-membered carbocyclic or heterocyclic group, optionally substituted with from 1 to 5 substituents independently selected from: (a) hydroxy, halogen, amino, cyano and nitro; and (b) $(C_1-C_6)$alkyl, $(C_2-C_6)$alkenyl, $(C_2-C_6)$alkynyl, $(C_5-C_7)$cycloalkyl $(C_1-C_6)$alkyl, $(C_1-C_6)$alkanesulfonyl, $(C_5-C_7)$cycloalkanesulfonyl, $(C_5-C_7)$cycloalkane $(C_1-C_6)$alkanesulfonyl, $(C_1-C_6)$alkoxy, $(C_5-C_7)$cycloalkoxy, $(C_5-C_7)$cycloalkyl$(C_1-C_6)$ alkoxy, mono—N—and di—N, N—$(C_1-C_6)$alkylamino, mono—N— and di—N,N—$(C_5-C_7$ )cycloalkylamino, N—$(C_1-C_6)$alkyl—N—$(C_5-C_7)$ cycloalkylamino, mono—N—and di—N,N—$(C_5-C_7)$ cycloalkyl$(C_1-C_6)$alkylamino, N—$(C_1-C_6)$alkyl—N—$(C_3-C_7)$cycloalkyl$(C_1-C_6)$ alkylamino, N—$(C_5-C_7)$ cycloalkyl—N—$(C_5-C_7)$cycloalkyl$(C_1-C_6)$alkylamino and 3- to 10-membered carbocyclic and heterocyclic groups, wherein each is optionally independently substituted with from 1 to 9 secondary substituents selected from hydroxy, halogen, amino, cyano and nitro.

Within certain embodiments of Formula III, $R_G$ is:

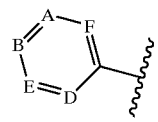

Wherein A, B, E, D and F are independently N or CR$_2$; and $R_2$ is independently selected at each occurrence from: hydrogen, halogen, hydroxy, amino, nitro, cyano, —C(=O)NH$_2$, —COOH and groups of the formula T—$R_C$—U—M, as described above.

Within certain embodiments, substituted spiro [isobenzofuran-1,4'-piperidin]-3-ones or 3H-spiroisobenzofuran-1,4'-piperidines provided herein exhibit a $K_i$ of 1 micromolar or less, 100 nanomolar or less, or 10 nanomolar or less in an NPY5 receptor ligand binding assay. The ligand (e.g., NPY or PYY) in such assays may be radiolabeled.

The present invention further provides NPY5 receptor modulators, comprising a compound as described above associated with (i.e., linked to or combined with) an additional components such as a drug, targeting moiety or carrier.

Within further aspects, the present invention provides pharmaceutical compositions comprising a compound or modulator as described above in combination with a physiologically acceptable carrier or excipient. Within certain embodiments, a pharmaceutical composition provided herein may further comprise one or more additional active agents (i.e., drugs). Pharmaceutical compositions provided herein may be formulated, for example, as an injectible fluid, an aerosol, a cream, a gel, a pill, a capsule, a syrup or a transdermal patch.

The present invention further provides, within other aspects, methods for treating a disease or disorder associated with NPY5 receptor activation, comprising administering to a patient in need of such treatment an effective amount of a compound or modulator as described above. Such diseases and disorders include, for example, eating disorders (e.g., obesity and bulimia nervosa), psychiatric disorders, cardiovascular disorders and diabetes. The compound or modulator may be administered orally, or via another means such as intranasally, intravenously or topically. Within certain embodiments, the patient is a human.

Within further aspects, the present invention provides compounds as described above, wherein the compounds are radiolabeled.

Methods are provided, within other aspects, for determining the presence or absence of NPY5 receptor in a sample, comprising the steps of: (a) contacting a sample with an agent comprising a compound as described above under conditions that permit binding of the agent to NPY5 receptor; and (b) detecting a level of agent bound to NPY5 receptor. Within certain embodiments, the agent is a radiolabeled compound, and the step of detection comprises the steps of: (i) separating unbound agent from bound agent; and (ii) detecting the presence or absence of bound agent in the sample. Detection may be achieved, for example, using autoradiography.

The present invention further provides, within other aspects, methods for modulating binding of NPY to NPY5 receptor. Certain such methods are performed in vitro, and comprise contacting NPY5 receptor with a compound or modulator as described above under conditions and in an amount sufficient to detectably modulate NPY binding to NPY5 receptor. Other such methods may be performed in vivo, and comprise contacting cells expressing NPY5 receptor with a compound or modulator as described above in an amount sufficient to detectably modulate NPY binding to cells expressing a cloned NPY5 receptor in vitro. Modulating of NPY binding may be determined, for example, using a ligand binding assay as provided herein.

Methods are further provided for modulating binding of NPY to NPY5 receptor in a patient, comprising administering to a patient (i.e., a human or non-human animal) a compound or modulator as described above. Patients may include, for example, companion animals such as dogs.

Within certain embodiments of the above methods, the modulation is inhibition and/or the NPY5 receptor is a human NPY5 receptor.

Within further aspects, the present invention provides methods for modulating the signal-transducing activity of NPY5 receptor, comprising contacting an NPY5 receptor, either in vivo or in vitro, with a sufficient amount of an NPY5 receptor modulator, under conditions suitable for binding of NPY to NPY5 receptor.

Also provided by the present invention are packaged pharmaceutical preparations, comprising: (a) a pharmaceutical composition as described above in a container; and (b) instructions for using the composition to treat a patient suffering from a disease or disorder associated with NPY5 receptor activation. Such disorders include, for example, eating disorders, psychiatric disorders, cardiovascular disorders (such as hypertension) and diabetes.

These and other aspects of the present invention will become apparent upon reference to the following detailed description.

DETAILED DESCRIPTION

As noted above, the present invention provides NPY5 receptor modulators comprising small molecule NPY5 receptor ligands that are substituted spiro[isobenzofuran-1,4'-piperidin]-3-ones or 3H-spiroisobenzofuran-1,4'-piperidines. Such modulators may be used in vitro or in vivo, to inhibit or enhance NPY binding to NPY5 receptor in a variety of contexts, discussed in further detail below.

Definitions

Prior to setting forth the invention in detail, it may be helpful to provide definitions of certain terms to be used herein. Compounds of the present invention are generally described using standard nomenclature. For compounds having asymmetric centers, it should be understood that all of the optical isomers and mixtures thereof are encompassed. In addition, compounds with carbon—carbon double bonds may occur in Z- and E-forms, with all isomeric forms of the compounds being included in the present invention. Where a compound exists in various tautomeric forms, the invention is not limited to any one of the specific tautomers, but rather includes all tautomeric forms. Certain compounds are described herein using a general formula that includes variables. Unless otherwise specified, each variable within such a formula is defined independently of other variables.

As used herein, "$C_1$–$C_8$ alkyl" refers to straight or branched chain alkyl groups having 1–8 carbon atoms such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl and 3-methylpentyl. A $C_1$–$C_8$ alkyl substituent may be bonded to an atom within a molecule of interest via any chemically suitable portion of the $C_1$–$C_8$ alkyl group. Preferred alkyl groups are $C_1$–$C_6$ alkyl groups, especially methyl, ethyl, propyl and butyl. Particularly preferred are $C_1$–$C_3$ alkyl groups. Similarly, "$C_2$–$C_8$ alkenyl" refers to straight or branched chain alkene groups having 2 to 8 carbon atoms, with $C_2$–$C_6$ groups preferred, and $C_2$–$C_4$ alkenyl groups particularly preferred. Within an alkenyl group, one or more unsaturated carbon—carbon double bonds are present, and may occur at any stable point along the chain (e.g., ethenyl, allyl and isopropenyl). "$C_2$–$C_8$ alkynyl" refers to straight or branched chain alkyne groups having 2 to 8 carbon atom), with $C_2$–$C_6$ groups preferred, and $C_2$–$C_4$ alkynyl groups particularly preferred. Within an alkynyl group, one or more unsaturated carbon—carbon triple bonds are present, and may occur at any stable point along the chain (e.g., ethynyl and propargyl). A "stable point" is bond that, when unsaturated, results in a chemically stable compound (i.e., a compound that can be isolated, characterized and tested for biological activity).

By "$C_3$–$C_{10}$ cycloalkyl" is meant alkyl groups having 3–10 carbon atoms forming a mono-, bi-, or polycyclic ring system, such as, for example, cyclopropyl, cyclopropylmethyl, cyclobutyl, cyclopentyl, cyclohexyl, cycloheptyl and norbornyl. "$C_3$–$C_8$ cycloalkyl" groups in which 3–8 carbon atoms form a single ring are preferred within certain embodiments and $C_5$–$C_6$ cycloalkyl rings are particularly preferred. Similarly, "cycloalkenyl" or "$C_3$–$C_{10}$ cycloalkenyl" refers to hydrocarbon groups having 3–10 carbon atoms forming a mono-, bi, or polycyclic ring system and containing one or more carbon—carbon double bonds which may occur at any stable point in the ring (e.g., cyclopentenyl, cyclohexenyl or cycloheptenyl). "Cycloalkynyl" or "$C_3$–$C_{10}$ cycloalkynyl" refers to hydrocarbon groups having 3–10 carbon atoms forming a mono-, bi, or polycyclic ring system and containing one or more carbon—carbon triple bonds which may occur at any stable point in the ring.

The term "(cycloalkyl)alkyl" or "($C_3$–$C_{10}$)cycloalkyl ($C_1$–$C_8$)alkyl" refers to a straight or branched alkyl substituent having 1 to 8 carbon atoms, that is further attached to a mono-, bi, or polycyclic ring system having 3–10 carbon atoms (e.g., cyclopropylmethyl, cyclobutylmethyl, cyclopentylmethyl, cyclohexylmethyl and cycloheptylmethyl).

"$C_2$–$C_8$ alkanoyl" refers to an acyl group with 2 to 8 carbon atoms in a linear, branched or cycloalkyl arrangement. $C_2$–$C_6$ alkanoyl groups are preferred, with $C_2$–$C_4$ alkanoyl groups particularly preferred.

"$C_2$–$C_8$ alkanone" refers to a ketone substituent with 2 to 8 carbon atoms in a linear, branched or cyclic arrangement. $C_2$–$C_6$ alkanone groups are preferred, with $C_2$–$C_4$ alkanone groups particularly preferred.

By "$C_1$–$C_8$ alkoxy," in the present invention, is meant an alkyl group of 1 to 8 carbon atoms attached via an oxygen bridge. $C_1$–$C_8$ alkoxy groups include, for example, methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy, and 3-methylpentoxy. $C_1$–$C_6$ alkoxy groups are generally preferred, with $C_1$–$C_4$ alkoxy groups particularly preferred, especially ethoxy and methoxy. Similarly, "$C_1$–$C_8$ alkylthio" refers to an alkyl group of 1 to 8 carbon atoms attached via a sulfur bridge. "$C_3$–$C_{10}$ aryloxy" refers to aryl groups of 3 to 10 carbon atoms attached via an oxygen bridge (e.g., phenoxy).

The term "$C_1$–$C_8$ alkoxycarbonyl" refers to an alkoxy group linked via a carbonyl. In other words, an alkoxycarbonyl group has the general structure —C(=O)—O—alkyl. $C_1$–$C_6$ alkoxycarbonyl groups are generally preferred, with $C_1$–$C_4$ alkoxycarbonyl groups particularly preferred.

"$C_1$–$C_8$ alkanoyloxy," as used herein, refers to an alkanoyl group linked via an oxygen bridge. In other words, an alkanoyloxy group has the general structure —O—C(=O)—alkyl. $C_1$–$C_6$ alkanoyloxy groups are generally preferred, with $C_1$–$C_4$ alkanoyloxy groups particularly preferred.

The term "$C_1$–$C_8$ carbonate" refers to an alkoxycarbonyl group linked via an oxygen bridge. In other words, a carbonate group has the general structure —O—C(=O)—O—alkyl. $C_1$–$C_6$ carbonate groups are generally preferred, with $C_1$–$C_4$ carbonate groups particularly preferred.

Similarly, "$C_2$–$C_8$ alkyl ether" refers to an ether substituent with 2 to 8 carbon atoms, positioned such that at least one carbon atom is located on either side of the oxygen atom. $C_2$–$C_6$ ether groups are preferred, with $C_2$–$C_4$ ether groups particularly preferred.

The term "halogen" includes fluorine, chlorine, bromine and iodine. A "haloalkyl" may be a branched or straight-chain saturated aliphatic hydrocarbon group, substituted with 1 or more halogen atoms. "Halo($C_1$–$C_8$)alkyl" groups have 1 to 8 carbon atoms; "halo($C_1$–$C_6$)alkyl" groups have 1 to 6 carbon atoms. Examples of haloalkyl groups include, but are not limited to, mono-, di- or tri-fluoromethyl; mono-, di- or tri-chloromethyl; mono-, di-, tri-, tetra- or penta-fluoroethyl; and mono-, di-, tri-, tetra- or penta-chloroethyl. Typical haloalkyl groups are trifluoromethyl and difluoromethyl. Preferably not more than 5, and more preferably not more than 3, haloalkyl groups are present in compounds provided herein. The term "haloalkoxy" refers to a haloalkyl group as defined above attached via an oxygen bridge. "Halo($C_1$–$C_8$)alkoxy" groups have 1 to 8 carbon atoms.

The term "hydroxy($C_1$–$C_8$)alkyl" (or "hydroxy($C_1$–$C_6$)alkyl") refer to aliphatic group having from 1 to 8 (or 1 to 6) carbon atoms, and further comprising at least one hydroxyl group on the main carbon chain and/or on a side chain. Hydroxy($C_1$–$C_8$)alkyl groups include, for example, 2-hydroxy-1,1-dimethyl-ethyl, 1-hydroxymethyl-2-methyl-propyl and 2-hydroxy-propyl.

The term "$C_1$–$C_8$ carbamate," as used herein, refers to a group having the general structure —N—C(=O)—O—alkyl. $C_1$–$C_6$ alkyl groups are generally preferred, with $C_1$–$C_4$ alkyl groups particularly preferred.

Any of the above groups may, of course be further substituted with any of the other groups listed above, provided that a stable compound results. Suitable substituents include, for example, halogens, cyano, nitro, $C_1$–$C_8$ alkyl, $C_2$–$C_8$ alkenyl, $C_2$–$C_8$ alkynyl, $C_1$–$C_8$ alkoxy, $C_1$–$C_8$ alkylthio, hydroxy, amino, mono or di($C_1$–$C_8$)alkyl amino, ($C_3$–$C_7$)cycloalkyl($C_0$–$C_3$)alkyl, halo($C_1$–$C_8$)alkyl, halo($C_1$–$C_8$)alkoxy, $C_1$–$C_8$ alkanoyl, $C_1$–$C_8$ alkoxycarbonyl, —COOH, —CONH$_2$, mono- or di-($C_1$–$C_8$) alkylcarboxamido, —SO$_2$NH$_2$, and mono or di($C_1$–$C_8$) alkylsulfonamido. Carbocyclic and heterocyclic groups as described below may also be used as substituents. Preferably, the above groups are substituted with 0 to 5 independently selected substituents; more preferably 0 to 3 independently selected substituents.

A "heteroatom," as used herein, is oxygen, sulfur or nitrogen.

A "carbocyclic group" comprises at least one ring formed entirely by carbon—carbon bonds. Such a group generally has from 1 to 3 fused or pendant rings, preferably one ring or two fused rings. Typically, each ring contains from 3 to 10 ring members, preferably from 5 to 8 ring members. Unless otherwise specified, such a ring may be aromatic or non-aromatic. Representative examples of carbocyclic groups are cycloalkyl groups (e.g. cyclopentane and cyclohexane), cycloalkenes and cycloalkynes, as well as aromatic groups such as phenyl, benzyl, naphthyl, phenoxyl, benzoxyl and phenylethanonyl. Carbon atoms present within a carbocyclic group may, of course, be further bonded to a variety of ring substituents, such as hydrogen, a halogen, cyano, nitro, $C_1$–$C_8$ alkyl, $C_2$–$C_8$ alkenyl, $C_2$–$C_8$ alkynyl, $C_1$–$C_8$ alkoxy, $C_1$–$C_8$ alkylthio, hydroxy, amino, mono or di($C_1$–$C_8$)alkyl amino, ($C_3$–$C_7$)cycloalkyl($C_0$–$C_3$)alkyl, halo($C_1$–$C_8$)alkyl, halo($C_1$–$C_8$)alkoxy, $C_1$–$C_8$ alkanoyl, $C_1$–$C_8$ alkoxycarbonyl, —COOH, —CONH$_2$, mono- or di-($C_1$–$C_8$) alkylcarboxamido, —SO$_2$NH$_2$, and mono or di($C_1$–$C_8$) alkylsulfonamido.

A "heterocyclic group" comprises at least one ring in which at least one ring atom is a heteroatom (i.e., N, O or S), and the remainder of the ring atoms are carbon. Preferably, a heterocyclic group comprises 1–4 heteroatoms; within certain embodiments 1 or 2 heteroatoms is preferred. A heterocyclic group generally has from 1 to 3 fused or pendant rings, preferably one ring or two fused rings. Typically, each ring contains from 3 to 10 ring members, preferably from 5 to 8 ring members, and may be optionally substituted with from 1 to 5 substituents such as halogen, cyano, nitro, $C_1$–$C_8$ alkyl, $C_2$–$C_8$ alkenyl, $C_2$–$C_8$ alkynyl, $C_1$–$C_8$ alkoxy, $C_1$–$C_8$ alkylthio, hydroxy, amino, mono or di($C_1$–$C_8$)alkyl amino, halo($C_1$–$C_8$)alkyl, halo($C_1$–$C_8$) alkoxy, hydroxy($C_1$–$C_8$)alkyl, hydroxy($C_1$–$C_8$)alkoxy $C_2$–$C_8$ alkanoyl, $C_1$–$C_8$ alkoxycarbonyl, —COOH, —$SO_2NH_2$, mono or dialkylsulfonamido, —C(O)$NH_2$ or mono or di($C_1$–$C_8$) alkylcarboxamido. Unless otherwise specified, a heterocyclic group may be aromatic or nonaromatic. As with a carbocyclic group, atoms within a heterocyclic ring may be further linked to a variety of ring substituents.

A heterocyclic ring may be attached to a pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. Preferably, if the total number of S and 0 atoms in the heterocycle exceeds 1, then these heteroatoms are not adjacent to one another. More preferably, the total number of S and 0 atoms in the heterocycle is not more than 1.

Examples of heterocyclic groups include, but are not limited to, acridinyl, azocinyl, benzimidazolyl, benzofuranyl, benzothio-furanyl, benzothiophenyl, benzoxazolyl, benzothiazolyl, benzotriazolyl, benzotetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, dithiazinyl, dihydrofurotetrahydrofuran, furanyl, fuirazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, quinoxalinyl, quinuclidinyl, tetrahydrofuranyl, tetrahydroisoquinolinyl, tetrahydroquinolinyl, tetrazolyl, thiadiazinyl, thiadiazolyl, thianthrenyl, thiazolyl, thienyl, thienothiazolyl, thienooxazolyl, thienoimidazolyl, thiophenyl, triazinyl and xanthenyl. It will be apparent that any such heterocyclic groups may be substituted with one or more substituents as described above.

Preferred heterocyclic groups include, for example, pyridyl, pyrimidinyl (e.g., pyrimidin-2-yl), pyridinyl (pyridin-2-yl, pyridin-3-yl and pyridin-4-yl), morpholinyl (e.g., morpholin-4-yl), piperidinyl (e.g., piperidin-1-yl), pyrrolidinyl (e.g., pyrrolidin-1-yl), tetrazolyl, triazinyl, thienyl, coumarinyl, imidazolyl, oxazolyl, isoxazolyl, indolyl, pyrrolyl, pyrazolyl, quinolinyl, isoquinolinyl, thiazolyl, benzothiadiazolyl, triazolyl, pyrazinyl, furyl, thienyl, benzothienyl, benzofuranyl, tetrahydropyranyl, tetrahydrofuranyl, indanyl, and substituted derivatives of the foregoing such as methyl-tetrahydropyran-2-yl and 2-hydroxy-indan-1-yl.

A "heterocycloalkyl," as used herein is a nonaromatic heterocyclic group having 3–10 carbon atoms, and at least one heteroatom. Preferred heterocycloalkyls are ($C_3$–$C_8$) heterocycloalkyls such as piperidine and pyrrolidine.

A "substituent," as used herein, refers to a molecular moiety that is covalently bonded to an atom within a molecule of interest. For example, a "ring substituent" may be a moiety such as a halogen, alkyl group, haloalkyl group or other group as discussed herein, that is covalently bonded to an atom (preferably a carbon or nitrogen atom) that is a ring member. The term "substitution" refers to replacing a hydrogen atom in a molecular structure with a substituent as described above, such that the valence on the designated atom is not exceeded, and such that a chemically stable compound (i.e., a compound that can be isolated, characterized, and tested for biological activity) results from the substitution. When a substituent is keto (i.e., =0), then 2 hydrogens on the atom are replaced. Keto substituents are not present on aromatic moieties. Groups that are "optionally substituted" are unsubstituted or are substituted by other than hydrogen at one or more available positions, typically 1, 2, 3 or 4 positions, by one or more suitable groups (which may be the same or different) as disclosed herein.

The term "NPY receptor" refers to a protein comprising any NPY receptor polypeptide sequence, with mammalian and especially human and monkey sequences generally preferred. "NPY5 receptor" refers to a protein comprising a NPY receptor subtype $Y_5$ sequence, such as those described within U.S. Pat. No. 5,602,024 and herein. An NPY or NPY5 receptor may consist entirely of a naturally-occurring sequence, or may comprise additional components (e.g., N-terminal leader sequence) that do not substantially inhibit the receptor's ability to bind ligand (i.e., at least 50% of the binding affinity of the receptor for NPY and/or PYY is retained). For example, a chimeric NPY5/NPY1 receptor, as described herein, is considered to be an NPY5 receptor. Similarly, truncated NPY receptor sequences, or sequences containing amino acid deletions, substitutes, additions or modifications may be used, provided that NPY receptor binding properties are not substantially diminished (i.e., at least 50% of the endogenous ligand-binding affinity is retained). The binding affinity of a candidate NPY receptor for ligand may be evaluated using a standard binding assay as provided herein.

A "NPY5 receptor modulator," also referred to herein as a "modulator," is a compound that modulates (i.e., increases or decreases) ligand binding to NPY5 receptor. In other words, a modulator may be an NPY5 receptor antagonist or agonist. Modulators comprise a compound that is a substituted spiro[isobenzofuran-1,4'-piperidin]-3-one or 3H-spiroisobenzofuran-1,4'-piperidine having NPY5 receptor modulating activity. A modulator may consist entirely of such a compound, or may further comprise one or more additional moieties, provided that the modulating activity of the active compound is not substantially diminished (i.e., the ability to increase or decrease ligand binding to NPY5 receptor, as determined using a binding assay provided herein, is not diminished by more than 50%). Such additional moieties include, for example, targeting moieties, other active agents and carriers, any of which may be linked to the active compound via a variety of standard techniques including direct condensation, or by way of bi- or multifunctional linkers. Alternatively, such additional moieties may be combined with the active compound, without covalent linking. A modulator binds "specifically" to NPY5 receptor if it binds human NPY5 receptor (total binding minus nonspecific binding) with a Ki that is 10-fold, preferably 100-fold, and more preferably 1000-fold, less than the Ki measured for modulator binding to other NPY receptors, such as NPY1. A modulator binds with "high affinity" if the $K_i$ at an NPY receptor is less than 1 micromolar, preferably less than 100 nanomolar or 10 nanomolar. Binding assays for evaluating Ki may be performed, for example, using the human in vitro NPY5 binding assay provided in Example 676, herein. Ligand binding to NPY1 receptor may be inhibited within such assays using well known techniques, such as through the use of Thomae compound, as described herein. It will be apparent that either NPY or PYY may be used as the ligand within binding assays.

A "targeting moiety," as used herein, is a substance (e.g., a compound or a cell) that increases the local concentration of a modulator in the vicinity of a target site in a patient. There are a wide variety of targeting moieties known in the art, including antibodies and fragments thereof, receptors, ligands and other molecules that bind to cells of, or close to, a target tissue.

A "carrier," "carrier group" or "carrier molecule" is a substance that may be associated with an active compound prior to administration to a patient, generally for the purpose of controlling stability or bioavailability of the compound. Carriers for use within such formulations are generally biocompatible, and may also be biodegradable. Carriers include, for example, monovalent or multivalent molecules such as serum albumin (e.g., human or bovine), egg albumin, peptides, polylysine and polysaccharides such as aminodextran and polyamidoamines. Carriers also include solid support materials such as beads and microparticles comprising, for example, polylactate polyglycolate, poly (lactide-co-glycolide), polyacrylate, latex, starch, cellulose or dextran. A carrier may bear the compounds in a variety of ways, including covalent bonding either directly or via a linker group, noncovalent interaction or admixture.

A moiety is "associated with" an active compound if the moiety is linked to (covalently or noncovalently) or combined with the active compound.

A "linker," as used herein, is any molecule that does not comprise a compound that modulates NPY binding to an NPY5 receptor, and that can be covalently linked to at least two chemical moieties. Linkers may be used to link another moiety to a compound that modulates NPY binding to an NPY5 receptor. In general, a linker is bi-functional or multi-functional (e.g., a branched structure). Numerous linkers are known in the art, and may be incorporated into an NPY receptor modulator using any appropriate method, which will be apparent to those of ordinary skill in the art.

A "prodrug" is a compound that does not fully satisfy the structural requirements of the compounds provided herein, but is modified in vivo, following administration to a patient, to produce an active compound of the present invention. For example, a prodrug may be an acylated derivative of a compound as provided herein. Prodrugs include compounds wherein hydroxy, amine or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups within the compounds provided herein.

A "patient" is any individual treated with a NPY5 receptor modulator as provided herein. Patients include humans, as well as other animals such as companion animals and livestock. Patients may be afflicted with a condition associated with undesirable NPY5 receptor activation, or may be free of such a condition (i.e., treatment may be prophylactic).

NPY5 Receptor Modulators

As noted above, the present invention provides neuropeptide $Y_5$ (NPY5) receptor modulators (i.e., agents that detectably modulate both ligand binding to NPY5 and NPY5 receptor-mediated signal transduction). Such modulators may be specific for NPY5 (i.e., do not detectably modulate ligand binding to other NPY receptors), or may also inhibit or enhance ligand binding to one or more additional NPY receptors, such as NPY1. NPY5 receptor modulators may be used to modulate NPY binding to NPY5 in vivo, especially in the treatment of feeding disorders (e.g., obesity and bulemia), psychiatric disorders, diabetes and cardiovascular diseases in humans, domesticated companion animals and livestock animals. Modulators may also be used within a variety of in vitro assays, such as assays for receptor activity, as probes for detection and localization of NPY5 receptors and as standards in assays of NPY binding and NPY-mediated cellular functions.

The NPY5 receptor modulators provided herein comprise active compounds that are substituted derivatives of spiro [isobenzofuran-1,4'-piperidin]-3-one or 3H-spiroisobenzofuran-1,4'-piperidine, which detectably modulate the binding of ligand to NPY5 receptor at nanomolar concentrations, preferably at subnanomolar concentrations. Certain active compounds bind specifically and/or with high affinity to NPY5 receptor. Active compounds may include receptor agonists and antagonists.

The present invention is based, in part, on the discovery that small molecules satisfying any one of Formulas I–IV (as well as pharmaceutically acceptable salts and prodrugs thereof) modulate NPY binding to NPY5 receptor.

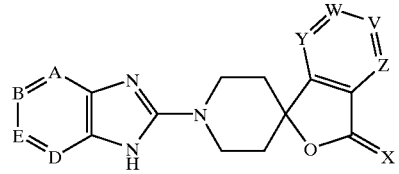

Formula I

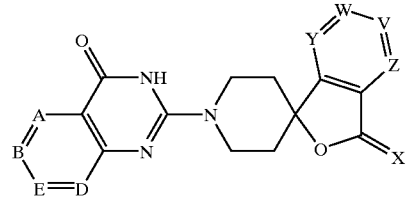

Formula II

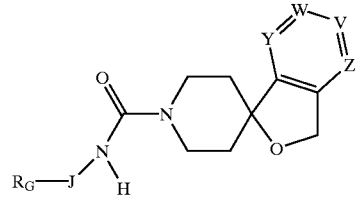

Formula III

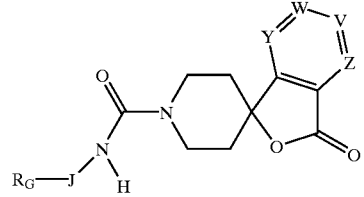

Formula IV

Within Formulas I–IV, X is oxygen or $H_2$; A, D, W, V, Y and Z are independently N or $CR_1$, B is N or $CR_2$ and E is N or $CR_3$. Within certain preferred embodiments, at least two of V, W, Y and Z are $CR_1$; preferably at least two of W, V, Y and Z (especially Y and Z) are CH, with the remainder $CR_1$. Within certain embodiments, W, V, Y and Z are all CH. A and D are preferably independently selected from N, CH and C-halogen; alternatively A and D are preferably $CR_1$, B is preferably $CR_2$ and E is preferably $CR_3$.

Within preferred embodiments of Formula III and Formula IV, positions designated W, V, Y and Z are $CR_1$; more preferably at least two.

$R_1$ is independently selected at each occurrence from hydrogen, halogen, hydroxy, amino, nitro, cyano, —C(=O)$NH_2$ and —COOH and groups of the formula L—$R_A$Q—G. Within L—RA—Q—G, L is a bond, —O—, —C(=O)—, —OC(=O)—, —C(=O)O—, —O—C(=O)O—, —S(O)$_n$—, —$NR_B$—, —C(=O)$NHR_B$—, —$NHR_B$C(=O)—, —$NR_B$S(O)$_n$— or —S(O)$_n$$NR_B$—; preferably L is —O—, —C(=O)—, —OC(=O)—, —C(=O)O— or —$NR_B$. n is independently chosen at each occurrence 0, 1 or 2. $R_A$ is ($C_1$–$C_8$)alkyl, ($C_2$–$C_8$)alkenyl, ($C_2$–$C_8$)alkynyl, ($C_3$–$C_8$) cycloalkyl, ($C_3$–$C_8$)cycloalkenyl, ($C_3$–$C_8$) cycloalkynyl or ($C_3$–$C_8$)heterocycloalkyl, each of which is optionally substituted with from 1 to 5 substituents independently selected from hydroxy, halogen, amino, cyano, nitro, ($C_1$–$C_6$)alkyl and halo($C_1$–$C_6$)alkyl. Preferably $R_A$ is ($C_1$–$C_6$)alkyl, ($C_2$–$C_6$)alkenyl, ($C_2$–$C_6$)alkynyl, ($C_5$–$C_7$) cycloalkyl, or ($C_5$–$C_7$)heterocycloalkyl, each of which is optionally substituted with from 1 to 5 substituents independently selected from hydroxy, halogen, amino, cyano, nitro, ($C_1$–$C_6$)alkyl and halo($C_1$–$C_6$)alkyl.

Within the formula L—$R_A$—Q—G, Q is a bond, —O—, —C(=O)—, —OC(=O)—, —C(=O)O—, —O—C(=O) O—, —S(O)$_n$—, —$CHR_B$—, —$NR_B$—, —C(=O) $NHR_B$—, —$NHR_B$C(=O)—, —$NR_B$S(O)$_n$— or —S(O)$_n$ $NR_B$; preferably Q is a bond, —O— or —$NR_B$—. $R_B$ is independently selected at each occurrence from hydrogen, ($C_1$–$C_8$)alkyl, ($C_3$–$C_8$)cycloalkyl, ($C_3$–$C_8$)cycloalkyl ($C_1$–$C_8$)alkyl and ($C_1$–$C_8$)alkyl($C_3$–$C_8$)cycloalkyl (preferably hydrogen, ($C_1$–$C_6$)alkyl or ($C_5$–$C_7$)cycloalkyl). G is: hydrogen; or ($C_1$–$C_8$)alkyl, ($C_2$–$C_8$)alkenyl, ($C_2$–$C_8$) alkynyl, ($C_3$–$C_8$)cycloalkyl($C_1$–$C_8$)alkyl, or a 3- to 10-membered carbocyclic or heterocyclic group, each of which is optionally substituted with from 1 to 5 substituents independently selected from hydroxy, halogen, amino, cyano, nitro, ($C_1$–$C_8$)alkyl, halo($C_1$–$C_8$)alkyl, ($C_1$–$C_8$) alkoxy, —NH($C_1$–$C_8$)alkyl, —N($C_1$–$C_8$)alkyl)$_2$, —NHC (=O)($C_1$–$C_8$)alkyl, —N($C_1$–$C_8$)alkylC(=O)(alkyl), —NHS(O)$_s$($C_1$–$C_8$)alkyl, —S(O)$_s$($C_1$–$C_8$)alkyl, —S(O)$_s$ NH($C_1$–$C_8$)alkyl and —S(O)$_s$N($C_1$–$C_8$)alkyl)$_2$, wherein s is 0, 1 or 2. Preferably, G is (i) hydrogen; or (ii) ($C_1$–$C_6$)alkyl, ($C_2$–$C_6$)alkenyl, ($C_2$–$C_6$)alkynyl, ($C_5$–$C_7$)cycloalkyl, ($C_5$–$C_7$)cycloalkyl($C_1$–$C_6$)alkyl or ($C_5$–$C_7$) heterocycloalkyl, each of which is optionally substituted with from 1 to 5 substituents independently selected from hydroxy, ($C_1$–$C_6$) alkyl, ($C_1$–$C_6$)alkoxy, halogen, amino, cyano and nitro. More preferably G is hydrogen.

$R_1$ is preferably independently selected at each occurrence from hydrogen, halogen, hydroxy, nitro, cyano, amino, ($C_1$–$C_6$)alkyl, ($C_1$–$C_6$)alkoxy, ($C_1$–$C_6$) alkoxy substituted with amino or mono- or di-($C_1$–$C_6$)alkylamino, ($C_3$–$C_7$) cycloalkyl, ($C_3$–$C_7$)cycloalkyl($C_1$–$C_4$)alkyl, ($C_2$–$C_6$) alkenyl, ($C_3$–$C_7$)cycloalkenyl, ($C_2$–$C_6$)alkynyl, ($C_{3-C7}$) cycloalkynyl, halo($C_1$–$C_6$)alkyl, halo($C_1$–$C_6$)alkoxy, mono and di($C_1$–$C_6$) alkylamino, amino($C_1$–$C_6$)alkyl, and mono- and di($C_1$–$C_6$)alkylamino($C_1$–$C_6$)alkyl. Particularly preferred $R_1$ groups include hydrogen, halogen, hydroxy, nitro, cyano, amino, ($C_1$–$C_6$)alkyl, ($C_1$–$C_6$)alkoxy, halo($C_1$–$C_6$) alkyl and halo($C_1$–$C_6$)alkoxy; especially hydrogen, methyl, ethyl, methoxy, ethoxy, and halogenated derivatives of the foregoing such as trifluoromethyl, trifluoromethoxy and difluoromethoxy.

Within Formulas I and II, $R_2$ and $R_3$ are each independently selected from hydrogen, halogen, hydroxy, amino, nitro, cyano, —C(=O)$NH_2$ and —COOH and groups of the formula T—$R_C$—U—M. Within the formula T—$R_C$—U—M, T is a bond, —O—, —C(=O)—, —OC(=O)—, —C(=O)O—, —O—C(=O)O—, —S(O)$_n$—, —$NR_D$—, —C(=O)NHRD—, —$NHR_D$C(=O)—, —$NR_D$S(O)$_n$— or —S(O)$_n$$NR_D$—, wherein n is 0, 1 or 2. Preferably, T is —O—, —C(=O)—, —OC(=O)—, —C(=O)O—, —S(O)$_n$— or —$NR_D$—. $R_C$ is ($C_1$–$C_8$)alkyl, ($C_2$–$C_8$) alkenyl, ($C_2$–$C_8$)alkynyl or a 3- to 10-membered carbocyclic or heterocyclic group, each of which is optionally substituted with from 1 to 5 substituents independently selected from hydroxy, halogen, amino, cyano, nitro, ($C_1$–$C_6$)alkyl and halo($C_1$–$C_6$)alkyl. n is independently chosen at each occurrence from 0, 1 or 2. Preferred $R_C$ groups include phenyl, pyridyl, thiazolyl, oxazolyl, thiadiazolyl, oxadiazolyl, pyrazolyl, isoxazolyl, piperazinyl, pyrimidinyl, pyridazinyl, pyrazinyl, pyranyl, thiophenyl, furanyl, pyrrolyl, imidazolyl, pyrrolidinyl, piperidinyl, piperazinyl and morpholinyl, each of which is substituted with from 0 to 2 substituents independently selected from hydroxy, halogen, amino, cyano, nitro, ($C_1$–$C_6$)alkyl, halo($C_1$–$C_6$) alkyl, ($C_1$–$C_6$)alkoxy and halo($C_1$–$C_6$) alkoxy.

Two substituents of $R_C$ may be linked to form a cyclic substituent. For example, two alkoxy substituents may join to form a five- or six-membered heterocyclic ring (i.e., a dioxalane or dioxane ring). One such $R_A$ group has the structure:

U (within the formula T—$R_C$—U—M) is a bond, —O—, —C(=O)—, —OC(=O)—, —C(=O)O—, —O—C(=O) O—, —S(O)$_n$—, —$CHR_D$—, —$NR_D$—, —C(=O) $NHR_D$—, —$NHR_D$C(=O)—, —$NR_D$S(O)$_n$— or —S(O)$_n$ $NR_D$—; preferably a bond, —O—, —C(=O)—, —OC (=O)—, —C(=O)O—, —S(O)$_n$—, —$CHR_D$— or —$NR_D$— and more preferably a bond, —C(=O)—, —$CHR_D$— or —$NR_D$—. $R_D$ is independently selected at each occurrence from hydrogen, ($C_1$–$C_8$)alkyl, ($C_3$–$C_8$) cycloalkyl, ($C_3$–$C_8$)cycloalkyl($C_1$–$C_8$)alkyl and ($C_1$–$C_8$) alkyl($C_3$–$C_8$)cycloalkyl (preferably each $R_D$ is independently hydrogen, ($C_1$–$C_6$)alkyl or ($C_5$–$C_7$)cycloalkyl). M is: hydrogen; or ($C_1$–$C_8$)alkyl, ($C_2$–$C_8$)alkenyl, ($C_2$–$C_8$)alkynyl or a 3- to 10-membered carbocyclic or heterocyclic group, each of which is optionally substituted with from 1 to 5 substituents independently selected from hydroxy, halogen, amino, cyano, nitro, ($C_1$–$C_8$)alkyl, halo($C_1$–$C_8$)alkyl, ($C_1$–$C_8$)alkoxy, —NH($C_1$–$C_8$)alkyl, —N(($C_1$–$C_8$)alkyl)$_2$, —NHC(=O)($C_1$–$C_8$)alkyl, —N($C_1$–$C_8$)alkylC(=O) (alkyl), —NHS(O)$_s$($C_1$–$C_8$)alkyl, —S(O)$_s$($C_1$–$C_8$)alkyl, —S(O)$_s$NH($C_1$–$C_8$)alkyl and —S(O)$_s$N(($C_1$–$C_8$)alkyl)$_2$, wherein s is 0, 1 or 2. Preferred M groups are (i) hydrogen; and (ii) ($C_1$–$C_6$)alkyl, ($C_2$–$C_6$)alkenyl, ($C_2$–$C_6$) alkynyl and 3- to 10-membered carbocyclic or heterocyclic groups, each of which is optionally substituted with from 1 to 5 substituents independently selected from hydroxy, halogen, amino, cyano, nitro, ($C_1$–$C_6$)alkyl, halo($C_1$–$C_6$)alkyl, ($C_1$–$C_6$) alkoxy, halo($C_1$–$C_6$) alkoxy NH($C_1$–$C_6$)alkyl and N($C_1$–$C_6$) alkyl)$_2$.

Preferred $R_2$ and $R_3$ groups are: (i) hydrogen and halogen; and (ii) $(C_1–C_6)$alkyl, $(C_5–C_7)$cycloalkyl, $(C_1–C_6)$alkenyl, $(C_1–C_6)$alkynyl, $(C_5–C_7)$ cycloalkyl$(C_1–C_6)$ alkyl, $(C_5–C_7)$ heterocycloalkyl, $(C_6–C_7)$heterocycloalkyl$(C_1–C_6)$alkyl and 3- to 10-membered carbocyclic and heterocyclic groups, each of which is optionally substituted with from 1 to 5 substituents independently selected from hydroxy, halogen, amino, cyano, nitro, $(C_1–C_6)$alkyl, halo$(C_1–C_6)$alkyl, $(C_1–C_6)$alkoxy, —NH$(C_1–C_6)$alkyl, —N$((C_1–C_6)$alkyl$)_2$, NHC(=O)$(C_1–C_6)$alkyl, —N$(C_1–C_6)$alkylC(=O)(alkyl), —NHS(O)$_s(C_1–C_6)$alkyl, —S(O)$_s(C_1–C_6)$alkyl, —S(O)$_s$NH$(C_1–C_6)$alkyl, —S(O)$_s$N$((C_1–C_6)$alkyl$)_2$ (wherein s is 0, 1 or 2) and 3- to 10-membered carbocyclic and heterocyclic groups. Representative examples of substituted and unsubstituted carbocyclic and heterocyclic groups include benzhydryl, phenyl, pyridyl (e.g., 4-pyridyl or 3-pyridyl), thiazolyl, oxazolyl, thiadiazolyl, triazolyl, oxadiazolyl, pyrazolyl, isoxazolyl, piperazinyl, pyrimidinyl, pyridazinyl, pyrazinyl, pyranyl, thiophenyl, furanyl, pyrrolyl, imidazolyl, pyrrolidinyl, piperidinyl, piperazinyl and morpholinyl, each of which is substituted with from 0 to 2 substituents independently selected from hydroxy, halogen, amino, cyano, nitro, $(C_1–C_6)$ alkyl, halo$(C_1–C_6)$alkyl, $(C_1–C_6)$alkoxy and halo$(C_1–C_6)$alkoxy. Substituted groups include, for example, 2-alkyl-4-pyridyl and 2-alkyl-3-pyridyl. Particularly preferred $R_2$ and $R_3$ groups are selected from hydrogen, halogen, cyano and T—$R_C$, wherein T is a bond, —O—, —C(=O)—, —OC(=O)—, —C(=O)O— or —S(0)$_2$— and $R_C$ is $(C_1–C_6)$alkyl or a 5- or 6-membered carbocyclic or heterocyclic ring, each of which is optionally substituted with form 1 to 3 substituents independently selected from hydroxyl, halogen, cyano, $(C_1–C_6)$ alkyl and halo$(C_1–C_6)$ alkyl. Such $R_2$ and $R_3$ groups include, for example, benzoyl, phenoxy, benzyloxy and substituted derivatives thereof.

Preferably, $R_2$ and $R_3$ are independently selected at each occurrence from: (i) trifluoromethoxy, trifluoromethyl, trifluorosulfonyl, hydrogen, halogen, hydroxy, nitro, cyano, amino, haloalkyl and —COOH; and (ii) benzoyl, benzhydryl, phenoxy, benzyloxy, phenyl, pyridyl, thiazolyl, oxazolyl, thiadiazolyl, oxadiazolyl, pyrazolyl, isoxazolyl, piperazinyl, pyrimidinyl, pyridazinyl, pyrazinyl, pyranyl, thiophenyl, furanyl, pyrrolyl, imidazolyl, pyrrolidinyl, piperidinyl, piperazinyl and morpholinyl, each of which is substituted with from 0 to 2 substituents independently selected from hydroxy, halogen, amino, cyano, nitro, $(C_1–C_6)$alkyl, halo$(C_1–C_6)$alkyl, $(C_1–C_6)$alkoxy and halo $(C_1–C_6)$alkoxy. More preferably, $R_2$ and $R_3$ are independently selected from: (i) hydrogen, halogen and cyano; and (ii) $(C_1–C_6)$alkyl, $(C_3–C_7)$ cycloalkyl, halo$(C_1–C_6)$alkyl, $(C_1–C_6)$ alkoxy, halo$(C_1–C_6)$alkoxy, $(C_1–C_6)$alkanoyl, $(C_1–C_6)$alkoxycarbonyl, $(C_1–C_6)$ alkylaminocarbonyl, $(C_1–C_6)$alkylsulfonyl, oxadiazolyl, oxazolyl, isoxazolyl, thiazolyl, thiophenyl, triazolyl, pyrimidinyl, pyridinyl, pyrazinyl, phenyl, benzyl, phenoxy, benzyloxy and benzoyl, wherein each is optionally substituted with 1 to 3 substituents selected from halogen and $(C_1–C_6)$alkyl. Within certain particularly preferred embodiments, at least one of $R_2$ and $R_3$ is selected from hydrogen, hydroxy, halogen, $(C_1–C_6)$ alkyl, halo$(C_1–C_6)$alkyl, $(C_1–C_6)$alkoxy and halo$(C_1–C_6)$ alkoxy.

Within certain preferred embodiments, $R_1$ is independently selected at each occurrence from hydrogen, hydroxy, halogen, $(C_1–C_6)$alkyl, halo$(C_1–C_6)$alkyl, $(C_1–C_6)$alkoxy and halo$(C_1–C_6)$alkoxy; either one of $R_2$ or $R_3$ is selected from hydrogen, hydroxy, halogen, $(C_1–C_6)$alkyl, halo $(C_1–C_6)$alkyl, $(C_1–C_6)$alkoxy and halo$(C_1–C_6)$ alkoxy; and the other of $R_2$ or $R_3$ is selected from hydroxy, halogen, cyano, and $(C_1–C_6)$alkyl, $(C_5–C_7)$cycloalkyl, halo$(C_1–C_6)$ alkyl, $(C_1–C_6)$alkoxy, halo$(C_1–C_6)$alkoxy, $(C_1–C_6)$alkanoyl, $(C_1–C_6)$alkanoyloxy, $(C_1–C_6)$alkoxycarbonyl, $(C_1–C_6)$ alkylaminocarbonyl, $(C_1–C_6)$ carbamate, $(C_1–C_6)$ alkylsulfonyl, oxadiazolyl, oxazolyl, isoxazolyl, thiazolyl, thiophenyl, triazolyl, pyrimidinyl, pyridinyl, pyrazinyl, phenyl, benzyl, phenoxy, benzyloxy and benzoyl, wherein each is optionally substituted with from 1 to 3 substituents independently selected from hydroxy, halogen, $(C_1–C_6)$ alkyl, halo$(C_1–C_6)$alkyl, $(C_1–C_6)$ alkoxy and halo$(C_1–C_6)$ alkoxy.

It will be apparent that combinations of $R_1$, $R_2$ and $R_3$ substituents are permissible only if such combinations result in stable compounds. As noted above, a stable compound or stable structure is meant to imply a compound that is sufficiently robust to survive isolation, characterization and testing for biological activity. Representative compounds of Formula I include, but are not limited to, (1) 1'-(6-trifluoromethyl-3-H-imidazo[4,5-b]pyridine-2-yl)-spiro[isobenzofuran-1,4'-piperidin]-3-one; (2) 1'-(7-chloro-1H-benzimidazol-2-yl)-spiro[isobenzofuran-1,4'-piperidin]-3-one; (3) 1'-(1H-benzimidazol-2-yl)-spiro[isobenzofuran-1,4'-piperidin]-3-one; (4) 1'-(5-n-propylsulfonyl-1H-benzimidazol-2-yl)-spiro[isobenzofuran-1,4'-piperidin]-3-one; (5) 1'-(5-cyano-1H-benzimidazol-2-yl)-spiro[isobenzofuran-1,4'-piperidin]-3-one; (6) 1'-(5-acetyl-1H-benzimidazol-2-yl)-spiro[isobenzofuran-1,4'-piperidin]-3-one; (7) 1'-(5-carboxy-1H-benzimidazol-2-yl)-spiro[isobenzofuran-1,4'-piperidin]-3-one, methyl ester; (8) 1'-(5'pyrazin-2-yl-1H-benzimidazol-2-yl)-spiro[isobenzofuran-1,4'-piperidin]-3-one; (9) 1'-(5'pyridin-3-yl-1H-benzimidazol-2-yl)-spiro[isobenzofuran-1,4'-piperidin]-3-one; (10) 1'-(5-trifluoromethoxy-1H-benzimidazol-2-yl)-spiro [isobenzofuran-1,4'-piperidin]-3-one; (11) 1'-(5-methyl-1H-benzimidazol-2-yl)-spiro[isobenzofuran-1,4'-piperidin]-3-one; (12) 1'-5benzoyl-1H-benzimidazol-2-yl)-spiro[isobenzofuran-1,4'-piperidin]-3-one; (13) 1'-(5-methoxy-1H-benzimidazol-2-yl)-spiro[isobenzofuran-1,4'-piperidin]-3-one; (14) 1'-(5-chloro-1H-benzimidazol-2-yl)-spiro[isobenzofuran-1,4'-piperidin]-3-one; (15) 6-bromo-7-chloro-2-(spiro[isobenzofuran-1,4'-piperidin]-3-one-3H-imidazo[4,5-b]pyridine; (16) 1'-(5-fluoro-1H-benzimidazol-2-yl)-spiro[isobenzofuran-1,4'-piperidin]-3-one; (17) 1'-(5-methyl-1H-benzimidazol-2-yl)-spiro[isobenzofran-1,4'-piperidin]-3-one; (18) 1'-(5-methylsulfonyl-1H-benzimidazol-2-yl)-spiro[isobenzofuran-1,4'-piperidin]-3-one; (19) 1'-(5-oxazol-2-yl-1H-benzimidazol-2-yl)-spiro[isobenzoflran-1,4'-piperidin]-3-one; (20) 1'-(5,6-difluoro-1H-benzimidazol-2-yl)-spiro[isobenzofuran-1,4'-piperidin]-3-one; (21) 1'-(5-phenyl-1H-imidazo[4,5-b]pyrazin-2-yl)-spiro[isobenzofuran-1,4'-piperidin]-3-one; (22) 1'-(5-trifluoromethyl-1H-benzimidazol-2-yl)-spiro[isobenzofuran-1,4'-piperidin]-3-one; (23) 1'-(5,7-dichloro-1H-benzimidazol-2-yl)-spiro[isobenzofuran-1,4'-piperidin]-3-one; (24) 1'-(5,6-dimethoxy-1H-benzimidazol-2-yl)-spiro[isobenzofuran-1,4'-piperidin]-3-one; (25) 1'-(5-trifluoromethylsulfonyl-1H -benzimidazol-2-yl)-spiro[isobenzofuran-1,4'-piperidin]-3-one; (26) 1'-(5-(3,5-dimethyl-isoxazol-4-yl)-1H-benzimidazol-2-yl)-spiro[isobenzofuran-1,4'-piperidin]-3-one; (27)1'-(5-ethoxy-1H-benzimidazol-2-yl)-spiro[isobenzofuran-1,4'-piperidin]-3-one; and (28) 5-chloro-2-(spiro[isobenzofuran-1,4'-piperidin]-3-one-3H-imidazo[4,5-b]pyridine; which are represented by the following structures:

(1)
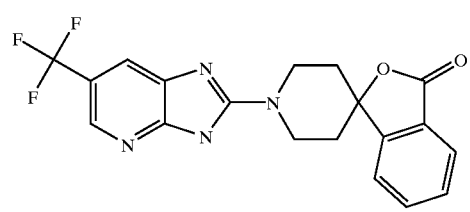
(2)
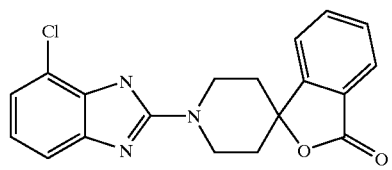
(3)
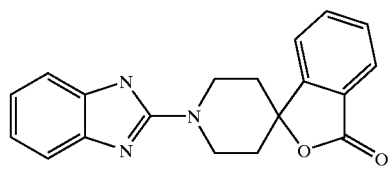
(4)
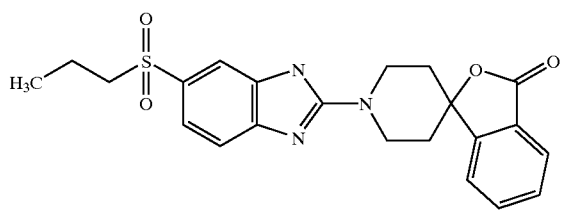
(5)
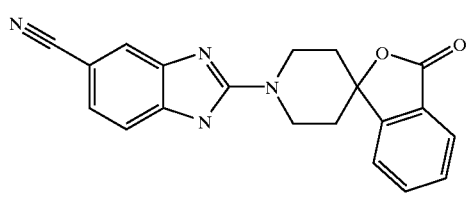
(6)
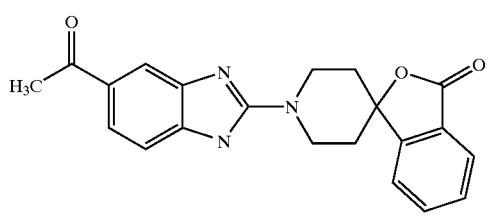
(7)
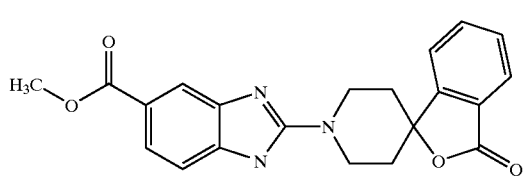
(8)
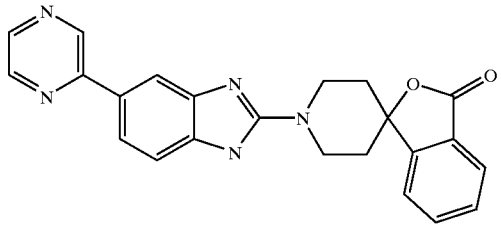
(9)
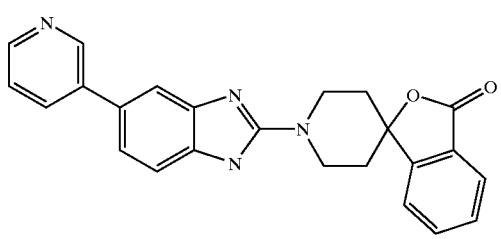
(10)
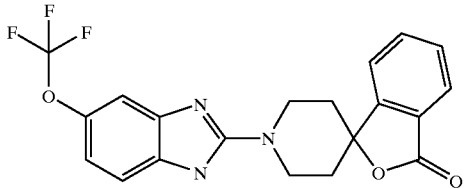
(11)
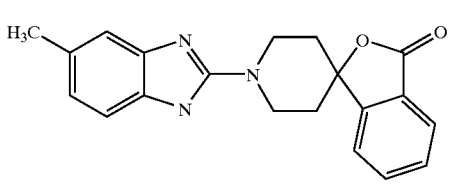
(12)
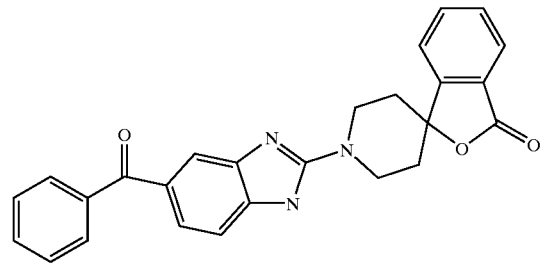
(13)
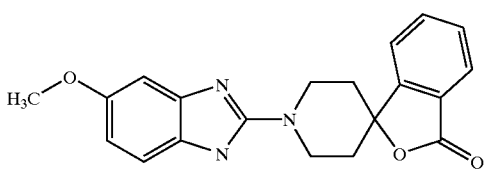
(14)
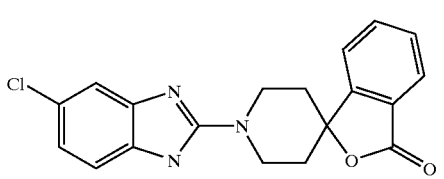

(15) 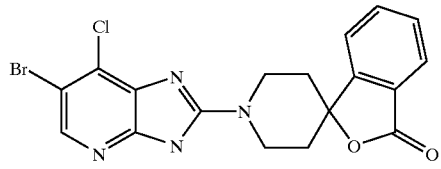
(16) 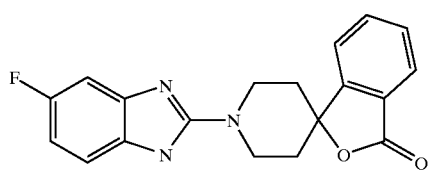
(17) 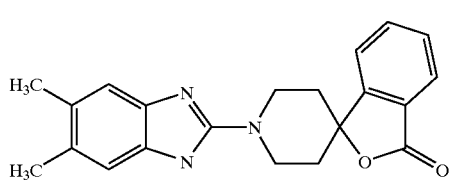
(18) 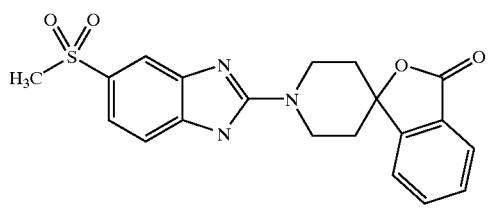
(19) 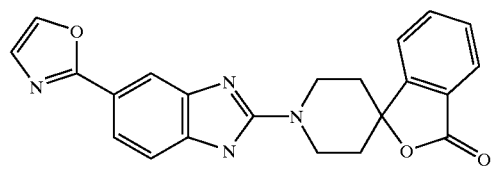
(20) 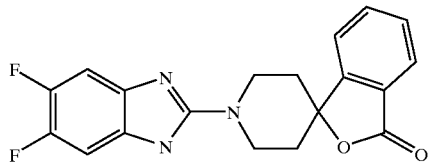
(21) 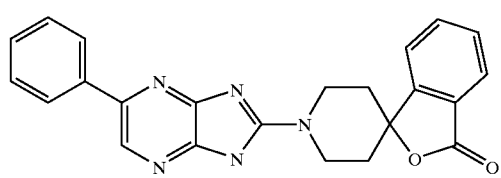
(22) 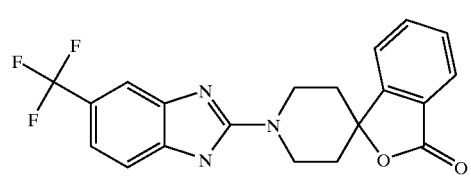
(23) 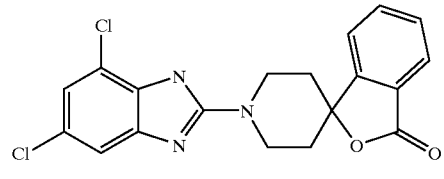
(24) 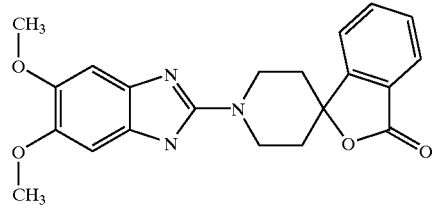
(25) 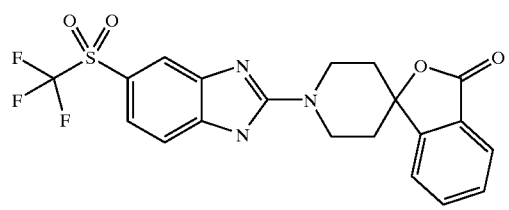
(26) 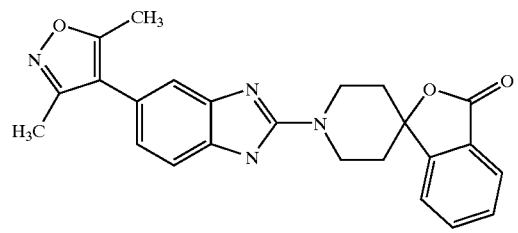
(27) 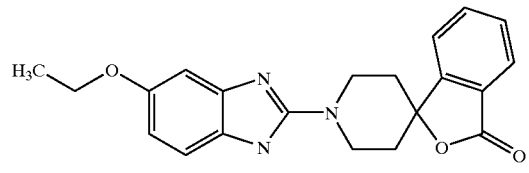
(28) 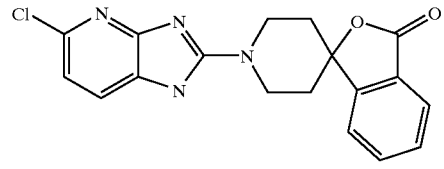

Representative compounds of Formula II include, but are not limited to, 1'-(6-iodo-1H-quinazolin-4-on-2-yl)spiro[isobenzofuran-1,4'piperidin]-3-one, which has structure 29:

(29)

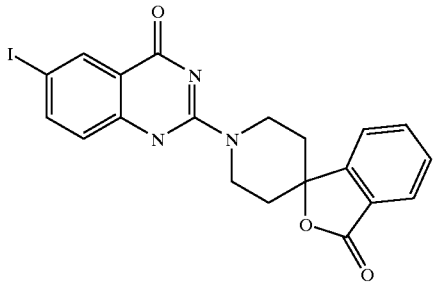

Within Formula III and Formula IV, positions designated W, V, Y and Z are as described above; J is a bond or (C$_1$–C$_6$)alkyl; and R$_G$ is (C$_1$–C$_8$)alkyl, (C$_2$–C$_8$) alkenyl, (C$_2$–C$_8$)alkynyl or a 3- to 10-membered carbocyclic or heterocyclic group, each of which is optionally substituted with from 1 to 5 substituents independently selected from hydrogen, halogen, hydroxy, amino, nitro, cyano, —C(=O)NH$_2$ and —COOH and groups of the formula T—R$_c$—U—M. Within the formula T—R$_c$—U—M, T, R$_c$ and U are as described above. M is (i) hydrogen; or (ii) (C$_1$–C$_8$)alkyl, (C$_2$–C$_8$)alkenyl, (C$_2$–C$_8$)alkynyl, (C$_3$–C$_8$)cycloalkyl (C$_1$–C$_8$)alkyl or a 3- to 10-membered carbocyclic or heterocyclic group, each of which is optionally substituted with from 1 to 9 substituents independently selected from hydroxy, halogen, amino, cyano, nitro, (C$_1$–C$_8$)alkyl, (C$_3$–C$_8$)cycloalkyl, halo(C$_1$–C$_8$)alkyl, (C$_1$–C$_8$)alkoxy, —NH(C$_1$–C$_8$)alkyl, —N(C$_1$–C$_8$)alkyl)$_2$, —NHC(=O)(C$_1$–C$_8$)alkyl, —N(C$_1$–C$_8$)alkylC(=O)(alkyl), —NHS(O)$_s$(C$_1$–C$_8$)alkyl, —S(O)$_s$(C$_1$–C$_8$)alkyl, —S(O)$_s$NH(C$_1$–C$_8$) alkyl and —S(O)$_s$N(C$_1$–C$_8$)alkyl)$_2$, wherein s is 0, 1 or 2. R$_G$ is preferably a 5- or 6-membered carbocyclic ring such as cyclohexyl or phenyl, or a heterocyclic ring such as thiadiazolyl, optionally substituted with from 1 to 5 substituents independently selected from hydroxy, halogen, amino, cyano, nitro, (C$_1$–C$_8$)alkyl, halo(C$_1$–C$_8$)alkyl, (C$_1$–C$_8$)alkoxy, —COOH, —NH(C$_1$–C$_8$)alkyl, —N(C$_1$–C$_8$)alkyl)$_2$, —NHC(=O)(C$_1$–C$_8$)alkyl, —N(C$_1$–C$_8$)alkylC(=O)(alkyl), —NHS(O)$_s$(C$_1$–C$_8$)alkyl, —S(O)$_s$(C$_1$–C$_8$) alkyl, —S(O)$_s$NH(C$_1$–C$_8$)alkyl and —S(O)$_s$N(C$_1$–C$_8$) alkyl)$_2$, wherein s is 0, 1 or 2. Preferred substituents for R$_G$ include (C$_1$–C$_6$)alkyl, halo(C$_1$–C$_6$)alkyl, (C$_1$–C$_6$)alkoxy, halo(C$_1$–C$_6$)alkoxy, —COOH, halogen, —SO$_2$—alkyl, (C$_1$–C$_6$)alkanoyl and cyano.

Within certain embodiments of Formula III, R$_G$ is:

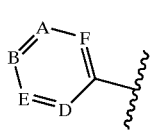

wherein A, B, E, D and F are independently N or CR$_2$; and R$_2$ is independently selected at each occurrence from: hydrogen, halogen, hydroxy, amino, nitro, cyano, —C(=O)NH$_2$ and —COOH; and (ii) groups of the formula T—R$_c$—U—M, as described above. Within certain embodiments, D and F are both CR$_2$, wherein R$_2$ is independently selected at each occurrence from hydrogen, halogen, (C$_1$–C$_6$)alkyl, halo(C$_1$–C$_6$)alkyl and (C$_1$–C$_6$) alkoxy, and A, B and E are all CR$_2$, wherein R$_2$ is independently selected from: (i) hydrogen, halogen and cyano; and (ii) (C$_1$–C$_6$)alkyl, (C$_3$–C$_7$)cycloalkyl, halo(C$_1$–C$_6$) alkyl, (C$_1$–C$_6$)alkoxy, halo (C$_1$–C$_6$)alkoxy, (C$_1$–C$_6$)alkanoyl, (C$_1$–C$_6$)alkoxycarbonyl, (C$_1$–C$_6$) alkylaminocarbonyl, (C$_1$–C$_6$)alkylsulfonyl, oxadiazolyl, oxazolyl, isoxazolyl, thiazolyl, thiophenyl, triazolyl, pyrimidinyl, pyridinyl, pyrazinyl, phenyl and benzoyl, wherein each is optionally substituted with 1 to 3 substituents selected from halogen and (C$_1$–C$_6$) alkyl. Within certain preferred embodiments, A, B, E, D and F are independently CR$_2$; T is a bond, —O—, —C(=O)—, —OC(=O)—, —C(=O)O—, —S(O)$_n$— or —NR$_D$—; n is 0 or 1; U is a bond, —O—, —C(=O)—, —OC(=O)—, —C(=O)O—, —S(O)$_n$—, —CHR$_D$— or —NR$_D$—; and M is: (i) hydrogen or (ii) (C$_1$–C$_8$)alkyl, (C$_2$–C$_8$)alkenyl, (C$_2$–C$_8$)alkynyl or a 3- to 10-membered carbocyclic or heterocyclic group, each of which is optionally substituted with from 1 to 5 substituents independently selected from hydroxy, halogen, amino, cyano, nitro, (C$_1$–C$_8$) alkyl, halo (C$_1$–C$_8$)alkyl, (C$_1$–C$_8$)alkoxy, —NH(C$_1$–C$_8$)alkyl and —N(C$_1$–C$_8$)alkyl)$_2$.

Within certain embodiments, J is a bond, and R$_G$ is a 5- or 6-membered carbocyclic or heterocyclic ring, optionally substituted with 1 or 2 substituents independently selected from hydrogen, halogen, hydroxy, nitro, cyano, amino, (C$_1$–C$_6$) alkyl, (C$_1$–C$_6$)alkoxy, halo(C$_1$–C$_6$)alkyl and halo (C$_1$–C$_6$)alkoxy.

Representative compounds of Formula III include, but are not limited to, 1'-(4-t-butyl-phenylcarbamoyl)-spiroisobenzofuran-1,4'-piperidine; 1'-(4-isopropyl-phenylcarbamoyl)-spiroisobenzofuran-1,4'-piperidine; and 1'-(4-trifluoromethyl-phenylcarbamoyl)-spiroisobenzofuran-1,4'-piperidine; which are represented by structures 30–32:

(30)

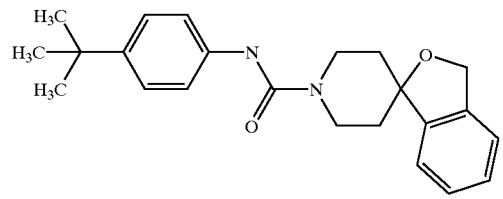

(31)

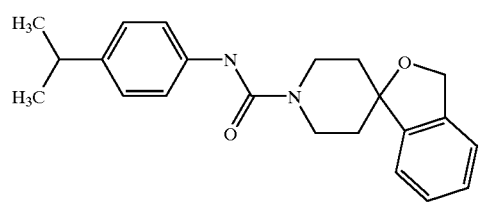

(32)

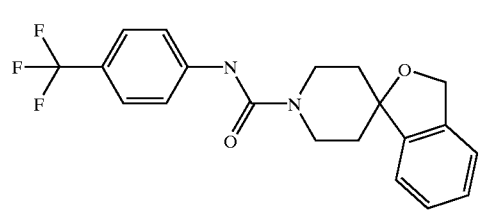

Within Formula IV, positions V, W, Y, Z, J and R$_G$ are as described above, with the proviso that if R$_G$, M or both are aromatic, then J is (C$_1$–C$_6$)alkyl. Within certain such embodiments, R$_G$ is a 5- or 6-membered carbocyclic or heterocyclic group such as optionally substituted cyclohexyl.

Representative compounds of Formula IV include, but are not limited to, 1'-(4'-carboxycyclohexylmethyl-carbamoyl)-spiro[isobenzofuran-1,4'-piperidine]-3-one; 1'-(1,4-dioxaspiro[4,5]dec-8-yl-carbamoyl)-spiro[isobenzofuran-1,4'-piperidine]-3-one; 1'-(3-phenylethyl-carbamoyl)-spiro[isobenzofuran-1,4'-piperidine]-3-one; 1'-(cyclohexyl-carbamoyl)-spiro[isobenzofuran-1,4'-piperidine]-3-one; and 1'-(4-bromo-3-phenylethyl-carbamoyl)-spiro[isobenzofuran-1,4'-piperidine]-3-one; which are represented by structures

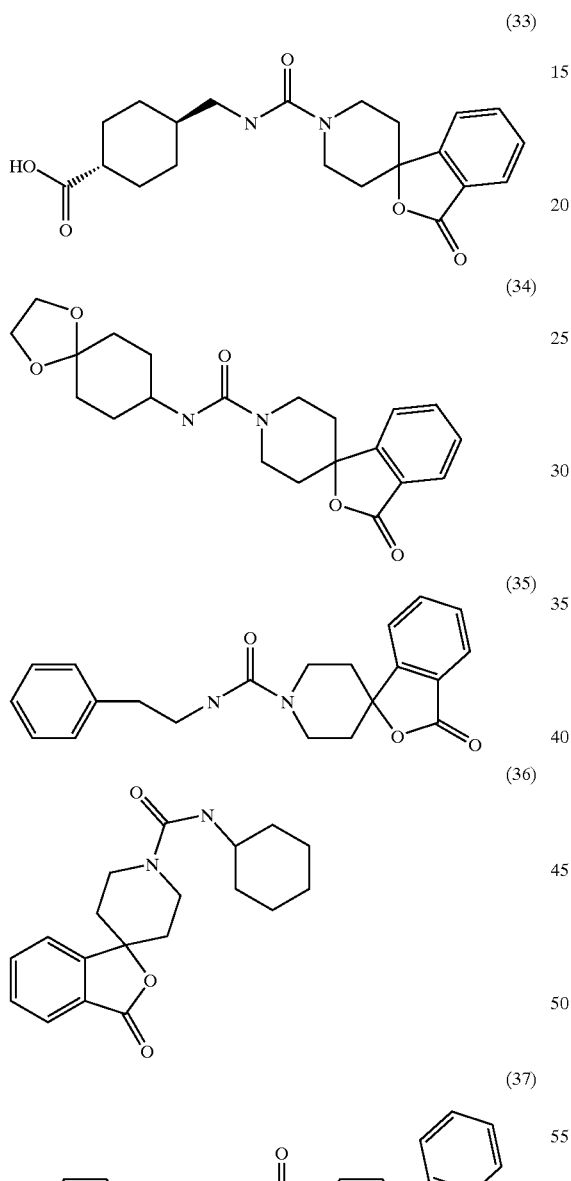

Within certain preferred embodiments, compounds provided herein satisfy one of Formulas Ia, IIa, IIIa or IVa, wherein each variable position is defined as described above.

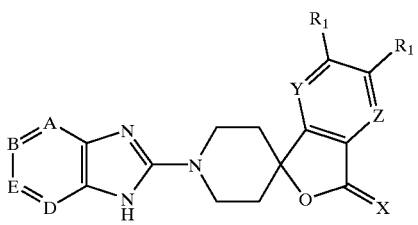

Formula Ia

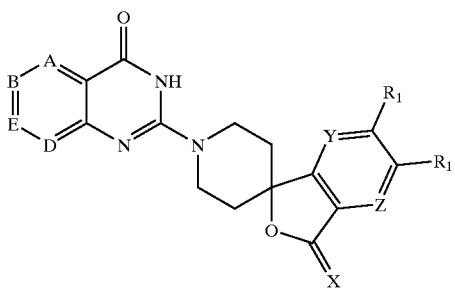

Formula IIa

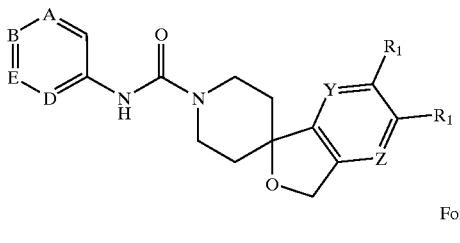

Formula IIIa

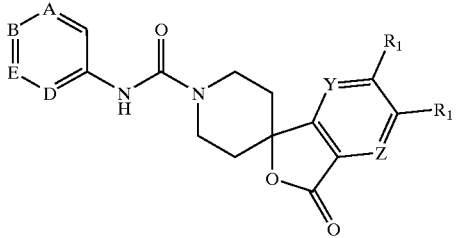

Formula IVa

Within certain particularly preferred embodiments, A, D, Y and Z of Formulas Ia, IIa, IIIa and IVa are all $CR_1$, B is $CR_2$ and E is $CR_3$; more preferably Y and Z are both CH, and A and D are $CR_1$, wherein $R_1$ is independently selected at each occurrence from hydrogen, halogen, methyl, and ethyl.

It will be apparent to those of ordinary skill in the art that the compounds specifically recited above are only representative examples of compounds provided herein, and are not intended to limit the scope of the present invention. Further, as noted above, all compounds of the present invention may be present as a free base or as a pharmaceutically acceptable acid addition salt or prodrug.

Substituted spiro[isobenzofuran-1,4'-piperidin]-3-ones and 3H-spiroisobenzofuran-1,4'-piperidines provided herein detectably alter (modulate) NPY binding to NPY5 receptor, as determined using standard in vitro NPY5 receptor ligand binding assays and/or signal transduction assays. References herein to an "NPY5 receptor ligand binding assay" are intended to refer to the protocol provided in Example 676. Briefly, a competition assay may be performed in which an NPY5 receptor preparation is incubated with labeled (e.g., $^{125}I$)NPY and unlabeled test compound. Within the assays provided herein, the NPY5 receptor used is preferably a mammalian NPY5 receptor, more preferably a human or monkey NPY5 receptor. The receptor may be recombinantly expressed or naturally expressed, and may comprise a native sequence or a modified sequence (e.g., truncated and/or fused to a non-native N-terminal sequence). The NPY5 receptor preparation may be, for example, a membrane preparation from Sƒ9 cells or Bowes Melanoma cells that recombinantly express human NPY5 receptor or a human chimeric NPY5/NPY1 receptor.

Incubation with a compound that detectably modulates NPY binding to NPY5 receptor will result in a decrease or increase in the amount of label bound to the NPY5 receptor preparation, relative to the amount of label bound in the absence of the compound. Preferably, such a compound will exhibit a $K_i$ at an NPY5 receptor of less than 1 micromolar, more preferably less than 500 nM, 100 nM, 20 nM or 10 nM, within an assay performed as described in Example 676. Generally preferred compounds are NPY5 receptor antagonists, and decrease NPY5 receptor activity (as measured by calcium mobilization, as described in Example 677) by at least 20%, preferably by at least 50%, and most preferably by at least 80%. For certain uses, preferred compounds also decrease food intake and weight gain in one or more animal models, such as food deprivation models (as described, for example, in published PCT application PCT/US00/26887) and the bovine pancreatic polypeptide antagonism model, as described in Example 678.

If desired, compounds provided herein may be evaluated for certain pharmacological properties including, but not limited to, oral bioavailability, serum protein binding and in vitro and in vivo half-life. In addition, penetration of the blood brain barrier may be desirable for compounds used to treat CNS disorders, while low brain levels of compounds used to treat peripheral disorders may be preferred. Routine assays that are well known in the art may be used to assess these properties, and identify superior compounds for a particular use. For example, assays used to predict bioavailability include transport across human intestinal cell monolayers, including Caco-2 cell monolayers. Penetration of the blood brain barrier of a compound in humans may be predicted from the brain levels of the compound in laboratory animals given the compound intravenously. Serum protein binding may be predicted from albumin binding assays. Compound half-life is inversely proportional to the frequency of dosage of a compound, and may be predicted from assays of microsomal half-life. In view of the present disclosure, a person of ordinary skill in the art could use such routine techniques to select a compound that displays optimal properties for a particular purpose.

As noted above, NPY5 receptor modulators provided herein may comprise, in addition to an active compound of any one of Formulas I–IV, one or more additional associated moieties. Such moieties may be linked directly (i.e., via a bond) or by way of a linker, may be noncovalently linked or may be combined with the compound. Such additional moieties may be used, for example, to facilitate delivery, targeting or detection of the compound. For example, compounds provided herein may sufficiently target a desired site in vivo; however, it may be beneficial for certain applications to include an additional targeting moiety to facilitate targeting to one or more specific tissues. Preferred targeting moieties include those that target to brain regions associated with NPY5 activity.

For certain embodiments, it may be beneficial to also, or alternatively, associate a drug with a modulator. As used herein, the term "drug" refers to any bioactive agent intended for administration to a mammal to prevent or treat a disease or other undesirable condition. Drugs include hormones, growth factors, proteins, peptides and other compounds. For example, modulators for treatment of eating disorders, particularly obesity and bulimia nervosa, may comprise an agent such as sibutramine, dexenfluramine, leptin, a growth hormone secretagogue, a melanocortin agonist, a beta-3 agonist, a 5HT-2 agonist, an orexin antagonist, a melanin concentrating hormone antagonist, a galanin antagonist, a CCK agonist, a GLP-1 agonist, a corticotropin-releasing hormone agonist or a NPYi antagonist. Moieties that facilitate detection include radionuclides, luminescent groups, fluorescent groups and enzymes, all of which may be associated with a compound via standard methods.

For detection purposes, as discussed in more detail below, compounds provided herein may be isotopically-labeled or radiolabeled. Such compounds are identical to those recited above, but for the fact that one or more atoms are replaced by an atom having an atomic mass or mass number different from the atomic mass or mass number usually found in nature. Examples of isotopes that can be incorporated into compounds provided herein include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$ and $^{36}Cl$. In addition, substitution with heavy isotopes such as deuterium (i.e., $^2H$) can afford certain therapeutic advantages resulting from greater metabolic stability (e.g., increased in vivo half-life or reduced dosage requirements) and, hence, may be preferred in some circumstances.

Other moieties that may be associated with an active compound include carriers. Such substances may modulate bioavailability or stability of the compound. Representative carriers include, for example, molecules such as albumin, polylysine, polyamidoamines, peptides, proteins, polystyrene, polyacrylamide, lipids, ceramide and biotin, solid support materials such as beads and microparticles comprising, for example, polylactate polyglycolate, poly (lactide-co-glycolide), polyacrylate, latex, starch, cellulose or dextran.

Preparation Of NPY5 Receptor Modulators

Substituted spiro[isobenzofuran-1,4'-piperidin]-3-ones and 3H-spiro[isobenzofuran-1,4'-piperidines may generally be prepared using standard synthetic methods, which are well known to those of ordinary skill in the art of organic synthesis. Representative methods are described below, and within Examples 1–674. Such methods may be combined with other known synthetic methods and variations thereon (e.g., modification of starting materials) that will be apparent to those of ordinary skill in the art, to generate all compounds provided herein.

By way of example, a synthetic route similar to those shown in any one of Schemes 1–7 (below) may be used. Within certain of these schemes, a base, inert solvent and/or organometallic catalyst may be used. Bases, in schemes, 1, 4 and 7, include, but are not limited to, alkali metal hydrides (preferably sodium hydride), alkali metal alkoxides (1–6 carbons) (preferably sodium methoxide, sodium ethoxide, or sodium tert-butoxide), alkaline earth metal hydrides, alkali metal dialkylamides (preferably lithium diisopropylamide), alkali metal carbonates, alkali metal bicarbonates, alkali metal bis-(trialkylsilyl)amides (preferably lithium or sodium (trimethylsilyl)amide), trialkylamines (preferably N,N-diisopropyl-N-ethyl amine or triethylamine), arylamines (preferably 4-dimethyl aniline) and heteroaromatic amines (preferably pyridine. Within Schemes 2, 3, 5 and 6, suitable bases include, for example, alkali metal alkoxides (1–6 carbons) (preferably sodium methoxide, sodium ethoxide, or sodium tert-butoxide), alkali metal carbonates (preferably sodium carbonate) or bicarbonates, alkali metal hydroxides, alkali metal phosphates and trialkylamines (preferably N,N-di-isopropyl-N-ethyl amine or triethylamine).

Inert solvents that may be used within schemes 1, 4 and 7 include, but are not limited to, alkyl alcohols (1–8 carbons; preferably methanol, ethanol, or tert-butanol), lower alkanenitriles (1–6 carbons; preferably acetonitrile), dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene) and haloalkanes (1–10 carbons and 1–10 halogens) (preferably dichloromethane). Within schemes 2, 3, 5 and 6, suitable inert solvents include, but are not limited to, lower alkanenitriles (1–6 carbons; preferably acetonitrile), water, dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide) and aromatic hydrocarbons (preferably benzene or toluene).

Organometallic catalysts that may be used in schemes 2, 3, 5 and 6 include, for example, palladium phosphine complexes (such as $Pd(PPh_3)_4$), palladium halides or alkanoates such as $PdCl_2(PPh_3)_2$ or $Pd(OAc)_2$) and nickel complexes (such as $NiCl_2(PPh_3)_2$).

SCHEME 1

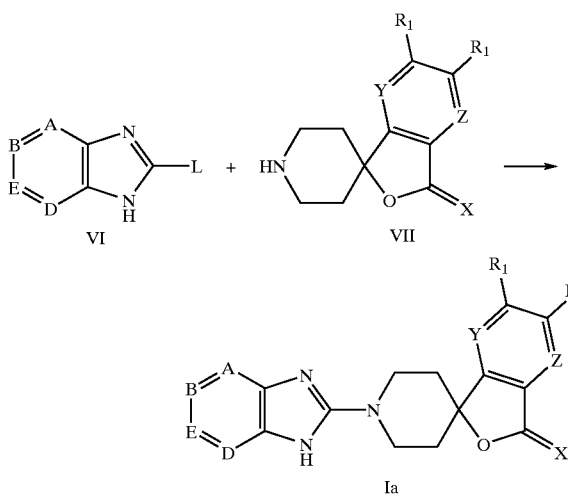

As illustrated in Scheme 1, compounds of Formula Ia can be prepared from intermediate compounds of formula VI, where L is a leaving group, such as a halogen (preferably chloro or bromo), alkane sulfonyloxy, aryl sulfonyloxy or haloalkane sulfonyloxy, and A, B, E and D are defined above. Compounds of formula VI react with a spiro [isobenzofuran-1,4'-piperidin]-3-one or a 3H-spiro [isobenzofuran-1,4'-piperidine of formula VII (Parham et al. (1976) J. Org. Chem. 41:2628–2633), where X, Z and $R_1$ are defined as above, in the presence or absence of a base in the presence or absence of an inert solvent, at reaction temperatures ranging from −78° C. to 250° C. to generate compounds of Formula Ia). Preferred reaction temperatures range from 0° C. to 140° C.

SCHEME 2

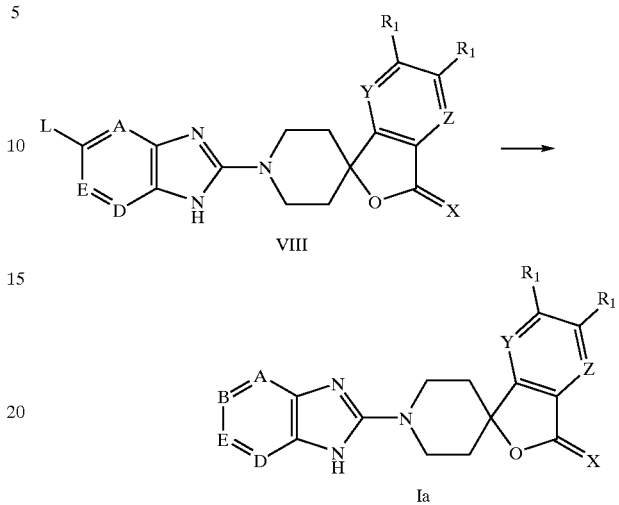

Alternatively, as illustrated in Scheme 2, compounds of Formula Ia, where B is $CR_2$ and $R_2$ is defined above, can be obtained starting from an intermediate of formula VIII, where B is C—L, and L is a halogen (preferably bromo or iodo), or haloalkane sulfonyloxy (preferably trifluoromethylsulfonyloxy), and A, E and D are as defined above. Compounds of formula VIII react with a compound of formula $R_2M$ (where M is alkali metal, ZnCl, ZnBr, MgBr, MgCl, MgI, $CeCl_2$, $CeBr_2$, copper halides, $B(OH)_2$, $B(O\text{-lower alkyl})_2$, or $Sn(\text{lower alkyl})_3$), in the presence or absence of an organometallic catalyst in the presence or absence of a base in an inert solvent, at temperatures ranging from −100° C. to 200° C. to give compounds of Formula Ia. Those skilled in the art will recognize that the reagents $R_2M$ may be generated in situ. Other substitution patterns on the aryl ring can be obtained under the same protocol, if A, E, or D are C—L, as defined above.

SCHEME 3

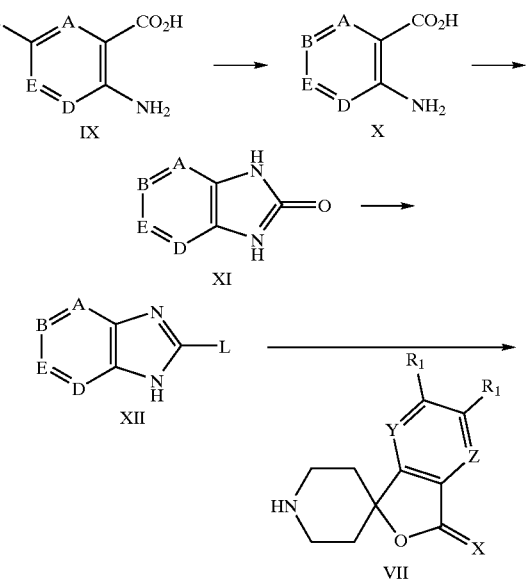

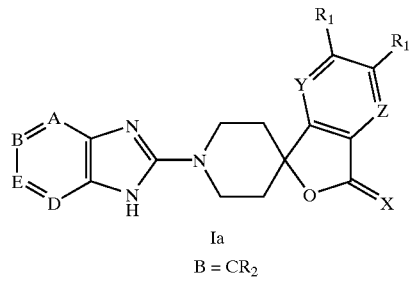

Ia
B = CR₂

Alternatively, as illustrated in Scheme 3, compounds of Formula Ia, where B is CR₂ as defined above, can be obtained starting from intermediates of formula IX, where L is a halogen (preferably bromo or iodo), or haloalkane sulfonyloxy (preferably trifluoromethylsulfonyloxy), and A, E and D are defined above. Compounds of formula IX react with a compound of formula R₂M (where M is alkali metal, ZnCl, ZnBr, MgBr, MgCl, MgI, CeCl₂, CeBr₂, copper halides, B(OH)₂, B(O-lower alkyl)₂, or Sn(lower alkyl)₃), in the presence or absence of an organometallic catalyst in the presence or absence of a base in an inert solvent, at temperatures ranging from −100° C. to 200° C. to give compounds of formula X, where B is CR₂. Those skilled in the art will recognize that the reagents R₂M may be generated in situ. Other substitution patterns on the aryl ring can be obtained under the same protocol, if A, E, or D are C—L, as defined above.

Compounds of formula X can be treated with diphenylphosphoryl azide in dioxane in the presence of triethylamine to produce compounds of formula XI. Compounds of formula XI can then be activated with a chlorinating agent, such as phosphorus oxychloride, in the presence of trialkylammonium chloride, preferably trimethylammonium chloride, in the presence or absence of solvent, to produce compounds of formula XII. Compounds of formula XII react with a spiro [isobenzofuran-1,4'-piperidin]-3-one or a 3H-spiro[isobenzofuran-1,4'-piperidine of formula VII under conditions similar to those described for compounds of formula VI in Scheme I, to produce compounds of Formula Ia.

SCHEME 4

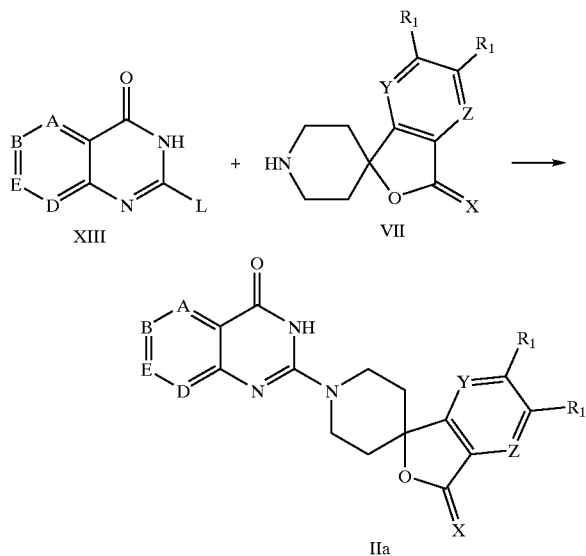

As illustrated in Scheme 4, compounds of Formula Ia can be prepared from intermediate compounds of formula XIII, where L is a leaving group, such as a halogen (preferably chloro or bromo), alkane sulfonyloxy, aryl sulfonyloxy or haloalkane sulfonyloxy, and A, B, E and D are as defined above. Compounds of formula XIII react with a spiro [isobenzofuran-1,4'-piperidin]-3-one or a 3H-spiro [isobenzofuran-1,4'-piperidine of formula VII, where X, Z and R are defined as above, in the presence or absence of a base in the presence or absence of an inert solvent, at reaction temperatures ranging from −78° C. to 250° C. to generate compounds of Formula Ia. Preferred reaction temperatures range from 0° C. to 140° C.

SCHEME 5

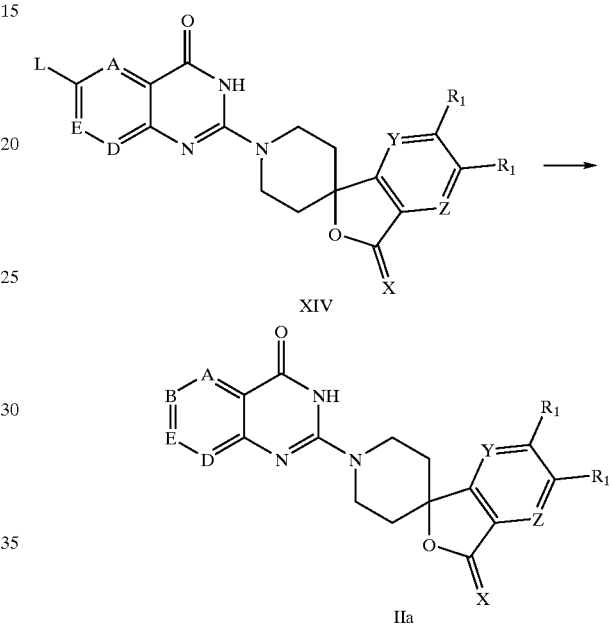

Alternatively, as illustrated in Scheme 5, compounds of Formula IIa, where B is CR₂ as defined above, can be obtained starting from an intermediate of formula XIV, where B is C—L, and L is a halogen (preferably bromo or iodo), or haloalkane sulfonyloxy (preferably trifluoromethylsulfonyloxy), and A, E and D are defined above. Compounds of formula XIV react with a compound of formula R₂M (where M is alkali metal, ZnCl, ZnBr, MgBr, MgCl, MgI, CeCl₂, CeBr₂, copper halides, B(OH)₂, B(O-lower alkyl)₂, or Sn(lower alkyl)₃), in the presence or absence of an organometallic catalyst in the presence or absence of a base in an inert solvent, at temperatures ranging from −100° C. to 200° C. to give compounds of Formula IIa. Those skilled in the art will recognize that the reagents R₂M may be generated in situ. Other substitution patterns on the aryl ring can be obtained under the same protocol, if A, E, or D are C—L, as defined above.

SCHEME 6

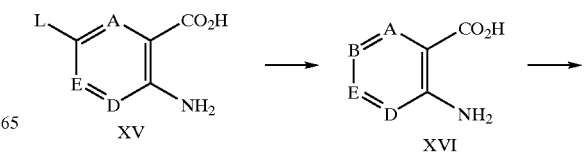

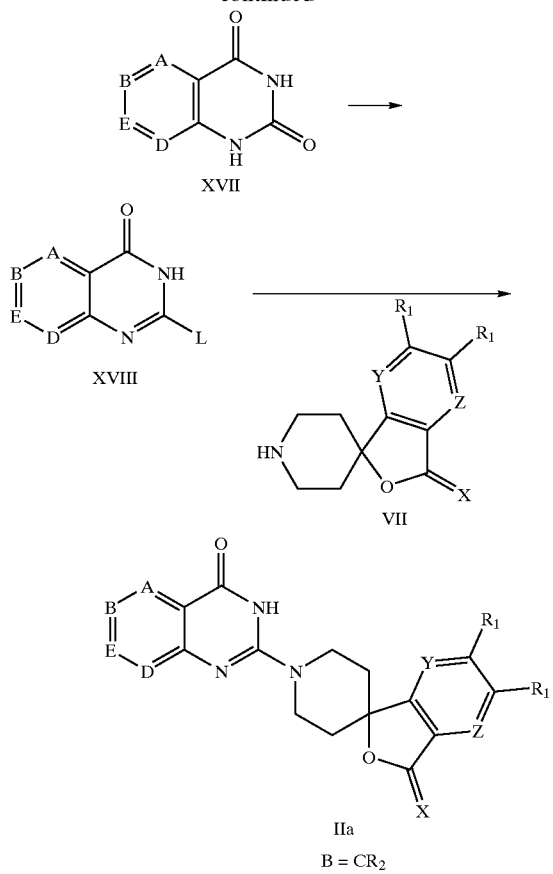

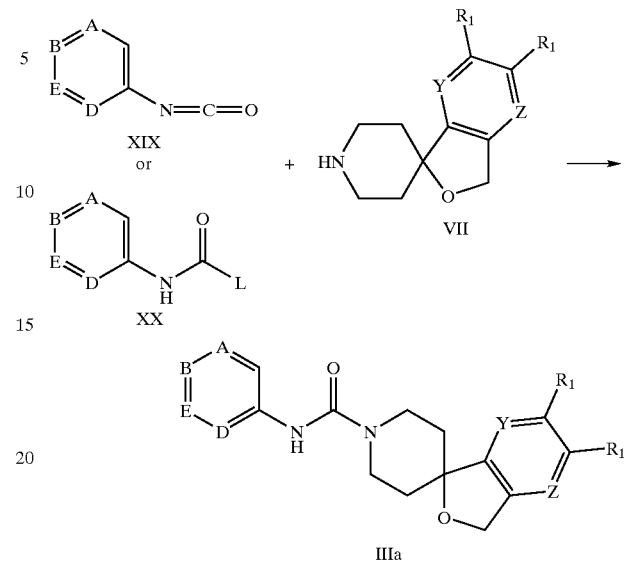

SCHEME 7

Alternatively, as illustrated in Scheme 6, compounds of Formula IIa, where B is CR$_2$ as defined above, can be obtained starting from intermediates of formula XV, where L is a halogen (preferably bromo or iodo), or halo alkane sulfonyloxy (preferably trifluoromethylsulfonyloxy), and A, E and D are defined above. Compounds of formula XV react with a compound of formula R$_2$M (where M is an alkali metal, ZnCl, ZnBr, MgBr, MgCl, MgI, CeCl$_2$, CeBr$_2$, a copper halide, B(OH)$_2$, B(O-lower alkyl)$_2$, or Sn(lower alkyl)$_3$), in the presence or absence of an organometallic catalyst in the presence or absence of a base in an inert solvent, at temperatures ranging from −100° C. to 200° C. to give compounds of formula XVI, where B is CR$_2$. Those skilled in the art will recognize that the reagents R$_2$M may be generated in situ. Other substitution patterns on the aryl ring can be obtained under the same protocol, if A, E or D are C—L, as defined above.

Compounds of formula XVI can be treated with potassium cyanate in acetic acid, followed by sodium hydroxide treatment, to produce compounds of formula XVII. Compounds of formula XVII can then be activated with a chlorinating agent, such as phosphorus oxychloride, in the presence of trialkylammonium chloride, preferably trimethylammonium chloride, in the presence or absence of solvent, to produce compounds of formula XVIII. Compounds of formula XVIII react with a spiro[isobenzofuran-1,4'-piperidin]-3-one or a 3H-spiro[isobenzofuran-1,4'-piperidine of formula VII under conditions similar to those described for compounds of formula XIII in Scheme 4, to produce compounds of Formula IIa.

As illustrated in Scheme 7, compounds of Formula IIIa can be prepared from isocyanates of formula XIX, or from activated compounds of formula XX where L is a leaving group, such as a halogen (preferably chloro or bromo), 4-nitrophenoxy, pentachlorophenoxy, and A, B, E and D are defined above. Compounds of formula XIX or XX react with a spiro[isobenzofuran-1,4'-piperidin]-3-one or a 3H-spiro[isobenzofuran-1,4'-piperidine of formula VII (where Y, Z and R$_1$ are defined as above), in the presence or absence of a base in the presence or absence of an inert solvent, at reaction temperatures ranging from −78° C. to 250° C. to generate compounds of Formula IIIa. Preferred reaction temperatures range from 0° C. to 140° C.

Compounds of Formula IV may be prepared using the schemes for the preparation of Formula IIIa, by altering the starting materials accordingly. Such variations will be apparent to those of ordinary skill in the art. In addition, those of ordinary skill in the art will recognize that the starting materials may be varied and additional steps employed to produce further compounds encompassed by the present invention.

In certain situations, the compounds of this invention may contain one or more asymmetric carbon atoms, so that the compounds can exist in different stereoisomeric forms. These compounds can be, for example, racemates or optically active forms. As noted above, all stereoisomers are encompassed by the present invention. Nonetheless, it may be desirable to obtain single enantiomers (i.e., optically active forms). Standard methods for preparing single enantiomers include asymmetric synthesis and resolution of the racemates. Resolution of the racemates can be accomplished, for example, by conventional methods such as crystallization in the presence of a resolving agent, or chromatography using, for example a chiral HPLC column.

As noted above, the present invention encompasses pharmaceutically acceptable salts of the compounds described herein. As used herein, a "pharmaceutically acceptable salt" is an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is 0–4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein, including those listed by *Remington's Pharmaceutical Sciences,* 17th ed., Mack Publishing Company, Easton, Pa, p. 1418 (1985). Accordingly, the present disclosure should be construed to include all pharmaceutically acceptable salts of the compounds specifically recited.

A wide variety of synthetic procedures are available for the preparation of pharmaceutically acceptable salts. In general, a pharmaceutically acceptable salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred.

The present invention also encompasses prodrugs of the compounds of Formulas I–III, which may be modified (either in routine manipulation or in vivo) to generate an active agent encompassed by Formulas I–III. Such prodrugs may be prepared by modifying functional groups present in the compounds in such a way that the modifications are cleaved to the parent compounds. Prodrugs include compounds wherein hydroxy, amine or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups within the compounds provided herein. Preferred prodrugs include acylated derivatives. Those of ordinary skill in the art will recognize various synthetic methods that may be employed to prepare prodrugs of the compounds provided herein.

Additional moieties may be associated with a compound using any suitable procedure. Covalent linkage may generally be achieved using suitable functional groups (e.g., hydroxy, carboxy, sulfhydryl or amino groups) on the compound and the moiety to be attached. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other. The use of bifunctional, multifunctional and/or cleavable linkers may also be desirable for certain applications. Such linkers are well known in the art. Compounds associated with carriers may be covalently linked or, preferably, such association does not involve covalent interaction and is achieved by mixing.

Compounds may be radiolabeled by carrying out their synthesis using precursors comprising at least one atom that is a radioisotope (i.e., an isotopically labeled reagent is substituted for a non-isotopically labeled reagent). Numerous radioisotopes are readily available, including isotopes of hydrogen, carbon, nitrogen, oxygen, phosphorous, sulfur, iodine, fluorine and chlorine, such as $^{14}C$, $^{3}H$, $^{35}S$ or $^{125}I$. Synthesis of radiolabeled compounds may be conveniently performed by a radioisotope supplier specializing in custom synthesis of radiolabeled probe compounds, such as Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif. Tritium labeled compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations may also be performed as a custom radiolabeling by any of the suppliers listed above using the compound as substrate. m addition, certain precursors may be subjected to tritium-halogen exchange with tritium gas, tritium gas reduction of unsaturated bonds, or reduction using sodium borotritide, as appropriate.

Pharmaceutical Compositions

The present invention also provides pharmaceutical compositions comprising NPY5 receptor modulators, together with at least one physiologically acceptable carrier or excipient. Such compositions may comprise, for example, water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. Preferred pharmaceutical compositions are formulated for oral delivery to humans or other animals (e.g., companion animals such as dogs).

If desired, other active ingredients may also be included. For example, compositions intended for the treatment of eating disorders, particularly obesity and bulimia nervosa, may further comprise an agent such as sibutramine, dexenfluramine, leptin, a growth hormone secretagogue, a melanocortin agonist, a beta-3 agonist, a 5HT-2 agonist, an orexin antagonist, a melanin concentrating hormone antagonist, a galanin antagonist, a CCK agonist, a GLP-1 agonist and/or a corticotropin-releasing hormone agonist or a $NPY_1$ antagonist.

Pharmaceutical compositions may be formulated for any appropriate manner of administration, including for example, topical, oral, nasal, rectal or parenteral administration. The term parenteral as used herein includes subcutaneous injections, intradermal, intravascular (e.g., intravenous), intramuscular, spinal, intracranial, intrathecal, intraperitoneal injection or like injection or infusion techniques. In certain embodiments, compositions in a form suitable for oral use are preferred. Such forms include, for example, tablets, troches, lozenges, aqueous or oily suspensions, dispersible powders or granules, emulsion, hard or soft capsules, or syrups or elixirs. Within yet other embodiments, compositions of the present invention may be formulated as a lyophilizate.

Compositions intended for oral use may further contain one or more components such as sweetening agents, flavoring agents, coloring agents and preserving agents in order to provide appealing and palatable preparations. Tablets contain the active ingredient(s) in admixture with physiologically acceptable excipients that are suitable for the manufacture of tablets. Such excipients include, for example, inert diluents (e.g., calcium carbonate, sodium carbonate, lactose, calcium phosphate or sodium phosphate), granulating and disintegrating agents (e.g., corn starch or alginic acid), binding agents (e.g., starch, gelatin or acacia) and lubricating agents (e.g., magnesium stearate, stearic acid or talc). The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules in which the active ingredient is mixed with an inert solid diluent (e.g., calcium carbonate, calcium phosphate or kaolin), or as soft gelatin capsules wherein the active ingredient is mixed with water or an oil medium (e.g., peanut oil, liquid paraffin or olive oil).

Aqueous suspensions contain the active materials in admixture with excipients suitable for the manufacture of aqueous suspensions. Such excipients are suspending agents (e.g., sodium carboxymethylcellulose, methylcellulose, hydropropylmethylcellulose, sodium alginate, polyvinylpyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitan monooleate, or condensation products of ethylene oxide with partial esters derived from fatty acids and hexitol anhydrides such as polyethylene sorbitan monooleate). Aqueous suspensions may also contain one or more preservatives, for example ethyl, or n-propyl p-hydroxybenzoate, one or more coloring agents, one or more flavoring agents, and/or one or more sweetening agents, such as sucrose or saccharin.

Oily suspensions may be formulated by suspending the active ingredients in a vegetable oil (e.g., arachis oil, olive oil, sesame oil or coconut oil), or in a mineral oil such as liquid paraffin. The oily suspensions may also contain a thickening agent such as beeswax, hard paraffin or cetyl alcohol. Sweetening agents, such as those set forth above, and/or flavoring agents may be added to provide palatable oral preparations. Such suspensions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and/or one or more preservatives. Suitable dispersing or wetting agents and suspending agents are exemplified by those already mentioned above. Additional excipients, such as sweetening, flavoring and/or coloring agents, may also be present.

Pharmaceutical compositions may also be in the form of oil-in-water emulsions. The oily phase may be a vegetable oil (e.g., olive oil or arachis oil), or a mineral oil (e.g., liquid paraffin) or mixtures thereof. Suitable emulsifying agents may be naturally-occurring gums (e.g., gum acacia or gum tragacanth), naturally-occurring phosphatides (e.g., soy bean, lecithin and esters or partial esters derived from fatty acids and hexitol), anhydrides (e.g., sorbitan monoleate) and condensation products of partial esters derived from fatty acids and hexitol with ethylene oxide (e.g., polyoxyethylene sorbitan monoleate). The emulsions may also contain sweetening and/or flavoring agents.

Syrups and elixirs may be formulated with sweetening agents, such as glycerol, propylene glycol, sorbitol or sucrose. Such formulations may also comprise one or more demulcents, preservatives, flavoring agents and/or coloring agents.

A pharmaceutical composition may be prepared as a sterile injectible aqueous or oleaginous suspension. The modulator, depending on the vehicle and concentration used, can either be suspended or dissolved in the vehicle. Such a composition may be formulated according to the known art using suitable dispersing, wetting agents and/or suspending agents, such as those mentioned above. Among the acceptable vehicles and solvents that may be employed are water, 1,3-butanediol, Ringer's solution and isotonic sodium chloride solution. In addition, sterile, fixed oils may be used as a solvent or suspending medium. For this purpose any bland fixed oil may be employed, including synthetic mono- or diglycerides. In addition, fatty acids such as oleic acid find use in the preparation of injectable compositions, and adjuvants such as local anesthetics, preservatives and/or buffering agents can also be dissolved in the vehicle.

Modulators may also be prepared in the form of suppositories (e.g., for rectal administration). Such compositions can be prepared by mixing the drug with a suitable non-irritating excipient that is solid at ordinary temperatures but liquid at the rectal temperature and will therefore melt in the rectum to release the drug. Suitable excipients include, for example, cocoa butter and polyethylene glycols.

For administration to non-human animals, the composition may also be added to animal feed or drinking water. It may be convenient to formulate animal feed and drinking water compositions so that the animal takes in an appropriate quantity of the composition along with its diet. It may also be convenient to present the composition as a premix for addition to feed or drinking water.

Pharmaceutical compositions may be formulated as sustained release formulations (i.e., a formulation such as a capsule that effects a slow release of modulator following administration). Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of modulator release. The amount of modulator contained within a sustained release formulation depends upon the site of implantation, the rate and expected duration of release and the nature of the condition to be treated or prevented.

Modulators are generally present within a pharmaceutical composition in a therapeutically effective amount. A therapeutically effective amount is an amount that results in a discernible patient benefit, such as increased healing of a disease or disorder associated with pathogenic NPY5 receptor activation, as described herein. A preferred concentration is one sufficient to inhibit the binding of ligand (i.e., NPY and/or PYY) to NPY5 receptor in vitro. Compositions providing dosage levels ranging from about 0.1 mg to about 140 mg per kilogram of body weight per day are preferred (about 0.5 mg to about 7 g per human patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. It will be understood, however, that the optimal dose for any particular patient will depend upon a variety of factors, including the activity of the specific compound employed; the age, body weight, general health, sex and diet of the patient; the time and route of administration; the rate of excretion; any simultaneous treatment, such as a drug combination; and the type and severity of the particular disease undergoing treatment. Optimal dosages may be established using routine testing, and procedures that are well known in the art.

Pharmaceutical compositions may be packaged for treating disorders responsive to NPY5 receptor modulation (e.g., treatment of eating disorders such as obesity or bulimia, psychiatric disorders, cardiovascular disorders such as hypertension or diabetes). Packaged pharmaceutical compositions generally include a container holding a therapeutically effective amount of at least one NPY5 receptor modulator as described herein and instructions (e.g., labeling) indicating that the contained composition is to be used for treating a disorder associated with NPY5 receptor activation in the patient.

Methods of Use

Within certain aspects, the present invention provides methods for inhibiting the development of a disease or disorder associated with NPY5 receptor activation. In other words, therapeutic methods provided herein may be used to treat an existing disease or disorder, or may be used to prevent or delay the onset of such a disease in a patient who is free of a detectable disease or disorder that is associated with NPY5 receptor activation. As used herein, a disease or disorder is "associated with NPY5 receptor activation" if it is characterized by inappropriate stimulation of NPY5 receptor, regardless of the actual amount of NPY present locally. Such conditions include, for example, eating disorders (such as obesity, anorexia, bulimia and metabolic disorders), diseases related to the central nervous system (such as psychiatric disorders), diseases related to abnormal hormone release (such as diabetes) and cardiovascular disorders. Diseases related to the central nervous system include cerebral infarction, neurodegeneration, epilepsy, stroke and conditions related to stroke, cerebral vasospasm and hemorrhage, depression, anxiety, schizophrenia and dementia, as well as conditions related to pain or nociception. Diseases related to abnormal hormone release include conditions associated with abnormal release of luteinizing hormone, growth hormone, insulin and prolactin. Cardiovascular disorders include any disorders or diseases pertaining to the heart, blood vessels or the renal system, such as hypertension, vasospasm, heart failure, shock, cardiac hypertrophy increased blood pressure, angina, myocardial infarction, sudden cardiac death, arrhythmia, peripheral vascular disease, and abnormal renal conditions such as impaired flow of fluid, abnormal mass transport or renal failure. Other diseases and disorders associated with NPY5 receptor activation include conditions related to increased sympathetic nerve activity (e.g., during or after coronary artery surgery, and operations and surgery in the gastrointestinal tract); diseases related to abnormal gastrointestinal motility and secretion (such as different forms of ileus, urinary incontinence and Crohn's disease); diseases related to sexual dysfunction and reproductive disorders; conditions or disorders associated with inflammation; and respiratory diseases, such as asthma and conditions related to asthma and bronchoconstriction. The above conditions may be diagnosed and monitored using criteria that have been established in the art. Patients may include humans, domesticated companion animals (pets, such as dogs) and livestock animals, with dosages and treatment regimes as described above.

Frequency of dosage may vary depending on the compound used and the particular disease to be treated or prevented. In general, for treatment of most disorders, a dosage regimen of 4 times daily or less is preferred. For the treatment of eating disorders, including obesity, a dosage regimen of 1 or 2 times daily is particularly preferred. For the treatment of impotence a single dose that rapidly reaches effective concentrations is desirable. It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

Within separate aspects, the present invention provides a variety of in vitro uses for the compounds provided herein. For example, such compounds may be used as probes for the detection and localization of NPY5 receptors, in samples such as tissue sections, as positive controls in assays for receptor activity, as standards and reagents for determining the ability of a candidate agent to bind to NPY5 receptor, or as radiotracers for positron emission tomography (PET) imaging or for single photon emission computerized tomography (SPECT). Such assays can be used to characterize NPY5 receptors in living subjects.

Within methods for determining the presence or absence of NPY5 receptor in a sample, a sample may be incubated with a compound as provided herein under conditions that permit binding of the compound to NPY5 receptor. The amount of compound bound to NPY5 receptor in the sample is then detected. For example, a compound may be labeled using any of a variety of well known techniques (e.g., radiolabeled with a radionuclide such as tritium, as described herein), and incubated with the sample (which may be, for example, a preparation of cultured cells, a tissue preparation or a fraction thereof). A suitable incubation time may generally be determined by assaying the level of binding that occurs over a period of time. Following incubation, unbound compound is removed, and bound compound detected using any method for the label employed (e.g., autoradiography or scintillation counting for radiolabeled compounds; spectroscopic methods may be used to detect dyes, luminescent groups and fluorescent groups). Detection assays, including receptor autoradiography (receptor mapping) of NPY5 receptors in cultured cells or tissue samples may be performed as described by Kuhar in sections 8.1.1 to 8.1.9 of Current Protocols in Pharmacology (1998) John Wiley & Sons, New York.

Modulators provided herein may also be used within a variety of well known cell culture and cell separation methods. For example, modulators may be linked to the interior surface of a tissue culture plate or other cell culture support, for use in immobilizing NPY5-expressing cells for screens, assays and growth in culture. Such linkage may be performed by any suitable technique, such as the methods described above, as well as other standard techniques. Modulators may also be used to facilitate cell identification and sorting in vitro, permitting the selection of cells expressing NPY5. Preferably, the modulator(s) for use in such methods are labeled as described herein. Within one preferred embodiment, a modulator linked to a fluorescent marker, such as fluorescein, is contacted with the cells, which are then analyzed by fluorescence activated cell sorting (FACS).

Within other aspects, methods are provided for modulating binding of an NPY5 receptor ligand (such as NPY or PYY) to NPY5 receptor in vitro or in vivo, comprising contacting a sufficient amount of NPY5 receptor with a modulator provided herein, under conditions suitable for binding of NPY5 to the receptor. Preferably, within such methods, NPY and/or PYY binding to receptor is inhibited by the modulator. The NPY5 receptor may be present in solution, in a cultured or isolated cell preparation or within a patient. In general, the amount of compound contacted with the receptor in vivo should be sufficient to modulate NPY binding to NPY5 receptor in vitro within, for example, a ligand binding assay as described in Example 676. $NPY_5$ receptors used to determine in vitro binding may be obtained from a variety of sources, for example from preparations of rat brain or from cells expressing cloned human $NPY_5$ receptors.

Also provided herein are methods for modulating the signal-transducing activity of NPY5 receptor, by contacting an NPY5 receptor, either in vivo or in vitro, with a sufficient amount of an NPY5 receptor modulator as described above, under conditions suitable for binding of NPY to NPY5 receptor. The NPY5 receptor may be present in solution, in a cultured or isolated cell preparation or within a patient. In general, the amount of a modulator that is sufficient to alter the signal-transducing activity of NPY5 receptor may be determined via a NPY5 receptor signal transduction assay, such as the assay described in Example 677.

The following Examples are offered by way of illustration and not by way of limitation. Unless otherwise specified all reagents and solvent are of standard commercial grade and are used without further purification.

EXAMPLES

Example 1

1'-(5-Pyridin-3-Y1-1h-Benzimidazol-2-Y1)-Spiro [Isobenzofuran-1,4'-Piperidin]-3-One This Example illustrates the preparation of the representative compound 1'-(5-pyridin-3-yl-1H-benzimidazol-2-yl)-spiro[isobenzofuran-1,4'-piperidin]-3-one.

A. 2-chloro-5-iodo-1H-benzimidazole

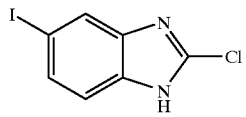

Heat a solution of 5-iodo-1,3-dihydro-benzimidazol-2-one (6.50 g, 25.0 mmol; Feitelson et al. (1952) J. Chem. Soc. 2389) and tetramethylammonium chloride (1.37 g, 12.5 mmol) to 100° C. in $POCl_3$ (10 mL) for 18 hours. After cooling, remove the excess $POCl_3$ in vacuo, and triturate the residue in ice-water (200 mL). After stirring for 30 minutes, filter the precipitate to obtain 2-chloro-5-iodo-1H-benzimidazole as a gray solid.

B. 1'-(5-iodo-1H-benzimidazol-2-yl)-spiroisobenzofuran-1,4'-piperidin-3-one

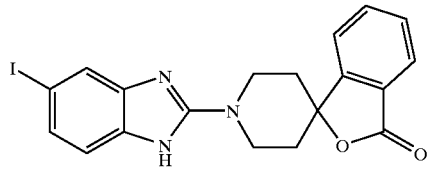

Heat a solution of 2 chloro-5-iodo-1H-benzimidazole (3.0 g, 10.7 mmol) and spiro[isobenzofuran-1,4'-piperidin]-3-one (2.63 g, 12.9 mmol) in dry NMP (15 mL) at 100° C. for 14 hours. Pour the cooled mixture into water (50 mL) and extract twice with EtOAc (50 mL). Wash the combined extracts with brine (30 mL), dry, and evaporate in vacuo. Purify by flash column chromatography (50% EtOAc-hexane) to obtain 1'-(5-iodo-1H-benzimidazol-2-yl)-spiro [isobenzofuran-1,4'-piperidin]-3-one as a beige solid.

C. 1'-(5-Pyridin-3-yl-1G-benzimidazol-2-yl)-spiroisobenzofuran-1,44'-piperidin-3-one

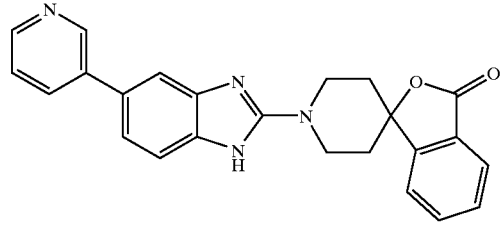

Add tetrakistriphenylphosphine palladium(0)(0.1 g, 0.01 mmol) to 1'-(5-iodo-1H-benzimidazol-2-yl)-spiro [isobenzofuran -1,4'-piperidin]-3-one (0.10 g, 0.22 mmol) in ethylene glycol dimethyl ether (2 mL). To this solution, add pyridine-3-boronic acid (0.06 g, 0.45 mmol) and aqueous sodium carbonate (1M, 1 mL) and heat the reaction at 80° C. for 2 hours. Extract the product with EtOAc (20 mL). Wash the combined extracts with brine (20 mL), dry over sodium sulfate, and concentrate in vacuo. Purify by flash column chromatography (5% $MeOH$—$CH_2Cl_2$) to obtain 1'-(5-pyridin-3-yl-1H-benzimidazol-2-yl)-spiro [isobenzofuran-1,4'-piperidin]-3-one as a white solid.

Example 2

1'-(5-Oxazol-2-Y1-1h-Benzimidazol-2-Y1)-Spiro [Isobenzofuran-1,4'-Piperidin]-3-One Hydrochloride This Example illustrates the preparation of the representative compound 1'-(5-oxazol-2-yl-1H-benzimidazol-2-yl)-spiro[isobenzofuran-1,4'-piperidin]-3-one.

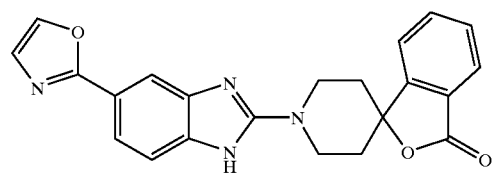

Add a solution of oxazole (0.5 mL, 7.24 mmol) in deoxygenated THF (50 mL) at −78° C. to 1.6 M n-butyllithium in hexane (5 mL, 7.96 mmol). After stirring for 30 minutes, add 1M zinc chloride in $Et_2O$ (22 mL, 21.7 mmol) and warm the reaction mixture to 0° C. for 2 hours. To the reaction mixture, add first a solution of 1'-(5-iodo-1H-benzimidazol-2-yl)-spiro[isobenzofuran-1,4'-piperidin]-3-one (3.2 g, 7.18 mmol), then the palladium catalyst which is prepared by treating a suspension of (Ph$_3$P)$_2$PdCl$_2$ (0.25 g, 0.36 mmol) in deoxygenated THF (50 mL) with 1.6 M n-butyllithium in hexane (0.45 mL, 0.72 mmol). Reflux the reaction mixture for 20 hours. After cooling to ambient temperature, dilute the mixture with EtOAc (50 mL), and wash with water (50 mL) and saturated aqueous NaCl (50 mL). Dry the organic portion over Na$_2$SO$_4$, filter and concentrate. Purify by flash column chromatography (5% MeOH—CH$_2$Cl$_2$) to obtain 1'-(5-oxazol-2-yl-1H-benzimidazol-2-yl)-spiro[isobenzofuran-1,4'-piperidin]-3-one as a white solid.

Example 3

1'-(5-Cyano-1h-Benzimidazol-2-Y1)-Spiro [Isobenzofuran-1,4'-Piperidin]-3-One

This Example illustrates the preparation of the representative compound 1'-(5-cyano-1H-benzimidazol-2-yl)-spiro [isobenzofuran-1,4'-piperidin]-3-one.

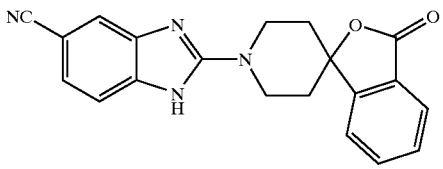

Add zinc cyanide (0.016 g, 0.13 mmol) and tetrakistriphenylphosphine palladium(0) (0.018 g, 0.02 mmol) to a solution of 1'-(5-iodo-1H-benzimidazol-2-yl)-spiro [isobenzofuran-1,4'-piperidin]-3-one (0.1 g, 0.22 mmol) in NMP (2 mL). Heat the reaction mixture at 130° C. for 19 hours. After cooling to ambient temperature, dilute the mixture with EtOAc (20 mL), and wash with water (20 mL) and saturated aqueous NaCl (20 mL). Dry the organic portion over Na$_2$SO$_4$, filter and concentrate. Purify by preparative TLC (80% EtOAc-hexane) to obtain 1'-(5-cyano-1H-benzimidazol-2-yl)-spiro[isobenzofuran-1,4'-piperidin]-3-one as a white solid.

Example 4

1'-(5-Acetyl-1h-Benzimidazol-2-Y1)-Spiro [Isobenzofuran-1,4'-Piperidin]-3-One

This Example illustrates the preparation of the representative compound 1'-(5-Acetyl-1H-benzimidazol-2-yl)-spiro [isobenzofuran-1,4'-piperidin]-3-one.

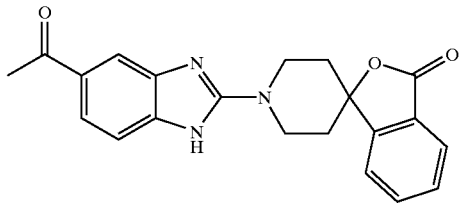

Add 1-ethoxyvinyltri-N-butyltin (0.49 g, 1.35 mmol) and bis (triphenyl-phosphine) palladium (II) chloride (0.05 g) to a solution of 1'-(5-iodo-1H-benzimidazol-2-yl)-spiro [isobenzofuran-1,4'-piperidin]-3-one (0.12 g, 0.27 mmol) in dioxane (5 mL). Reflux the reaction mixture for 12 hours. After cooling to ambient temperature, concentrate the reaction mixture in vacuo, and add to a solution of 10% HCl (2 mL) in THF (5 mL). After stirring for 30 minutes, dilute the solution with EtOAc (30 mL), and wash with saturated NaHCO$_3$ (30 mL) and saturated aqueous NaCl (30 mL). Dry the organic portion over Na$_2$SO$_4$, filter and concentrate. Purify by preparative TLC (10% MeOH—CH$_2$Cl$_2$) to obtain 1'-(5-acetyl-1H-benzimidazol-2-yl)-spiro[isobenzofuran-1,4'-piperidin]-3-one as a yellow solid.

Example 5

1'-(5-Trifluoromethyl-1h-Benzimidazol-2-Y1)-Spiro [isobenzofuran-1,4'-Piperidin]-3-One Hydrochloride This Example illustrates the preparation of the representative compound 1'-(5-trifluoromethyl-1H-benzimidazol-2-yl)-spiro[isobenzofuran-1,4'-piperidin]-3-one hydrochloride.

A. 2-chloro-5-trifluoromethyl-1H-benzimidazole

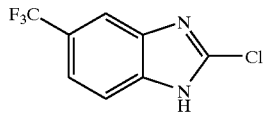

Reflux 5-trifluoromethyl-1,3-dihydro-benzimidazol-2-one (17 g; Meanwell et al. (1995) J. Org. Chem. 60(6) :1565–1582) for 14 hours in POCl$_3$ (200 mL). Evaporate the solvent in vacuo, then carefully neutralize with saturated NaHCO$_3$, and extract with EtOAc. Dry over Na$_2$SO$_4$, concentrate under vacuum, and purify by flash chromatography (1 :1 hexanes/EtOAc) to obtain 2-chloro-5-trifluoromethyl-1H-benzimidazole.

B. 1'-(5-trifluoromethyl-1H-benzimidazol-2-yl)-spiro [isobenzofuran-1,4'-piperidin]-3-one hydrochloride

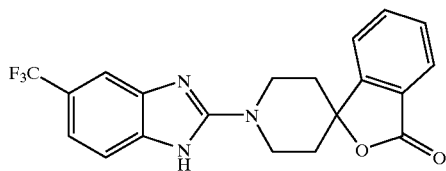

Stir 2-chloro-5-trifluoromethyl-1H-benzimidazole (7 g) and spiro[isobenzofuran-1,4'-piperidin]-3-one (12.9 g) in dimethylacetamide (75 mL) at 120° C. for 14 hours. Cool the mixture and partition between EtOAc and half-saturated NaHCO$_3$, wash several times with water, dry and concentrate in vacuo. Crystallize in EtOAc/EtOH to obtain a white solid. Purify the mother liquor by chromatography (1:1 hexanes/EtOAc) to obtain additional solid. Dissolve the combined solids in EtOAc and treat with saturated EtOAc/HCl. Collect 1'-(5-trifluoromethyl-1H-b enzimidazol-2-yl)-spiro [isobenzofuran-1,4'-piperidin]-3-one hydrochloride.

Example 6

1'-(5-Trifluoromethylsulfonyl-1h-Benzimidazol-2-Y1)-Spiro[Isobenzofuran-1,4'-Piperidin]-3-One Hydrochloride This Example illustrates the preparation of the representative compound 1'-(5-trifluoromethylsulfonyl-1H-benzimidazol-2-yl)-spiro[isobenzofuran-1,4'-piperidin]-3-one hydrochloride.

A. N-(4-Trifluoromethylsulfonyl-phenyl)-acetamide

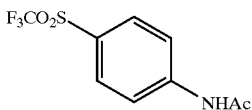

Reflux 4-trifluoromethylsulfonyl-phenylamine (5 g) and Ac$_2$O (2.2 mL) for 1.5 hours in HOAc (20 mL). Evaporate the solvent in vacuo, then crystallize the residue in EtOAc/EtOH to obtain N-(4-trifluoromethylsulfonyl-phenyl)-acetamide.

B. N-(2-Nitro-4-trifluoromethylsulfonyl-phenyl)-acetamide

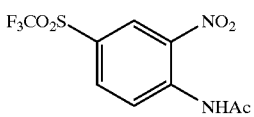

Cautiously add N-(4-trifluoromethylsulfonyl-phenyl)-acetamide (5 g) to an ice-water cooled fuming HNO$_3$ (30 mL) and stir for 6 hours at ambient temperature. Pour the mixture onto ice-water (500 mL) and collect the precipitate. Purify by flash chromatography (1:1 hexanes/EtOAc) to obtain N-(2-nitro-4-trifluoromethylsulfonyl-phenyl)-acetamide.

C. 2-Nitro-4-trifluoromethylsulfonyl-phenylamine

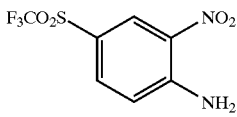

Reflux N-(2-nitro-4-trifluoromethylsulfonyl-phenyl)-acetamide (600 mg) for 40 minutes in concentrated HCl (15 mL) and water (5 mL). Cool the mixture to room temperature and collect the precipitate obtain 2-nitro-4-trifluoromethylsulfonyl-phenylamine.

D. 4-Trifluoromethylsulfonyl-benzene-1,2-diamine

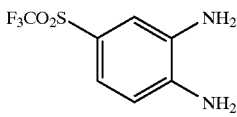

Dissolve 2-nitro-4-trifluoromethylsulfonyl-phenylamine (530 mg) in EtOH (50 mL) and hydrogenate over Pd/C (10%) for 6 hours. Filter the mixture and concentrate the filtrate in vacuo to obtain 4-trifluoromethylsulfonyl-benzene-1,2-diamine.

E. 5-Trifluoromethylsulfonyl-1,3-dihydro-benzimidazol-2-one

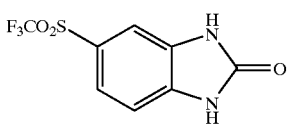

Reflux 4-trifluoromethylsulfonyl-benzene-1,2-diamine (420 mg) and CDI (284 mg) for 16 hours in CH$_3$CN (30 mL). Evaporate the solvent in vacuo. Purify by flash chromatography (1:1 hexanes/EtOAc) to obtain 5-trifluoromethylsulfonyl-1,3-dihydro-benzimidazol-2-one.

F. 2-Chloro-5-trifluoromethylsulfonyl-1H-benzimidazole

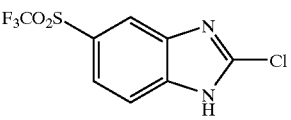

Reflux 5-trifluoromethylsulfonyl-1,3-dihydro-benzimidazol-2-one (380 mg) for 8 hours in POCl$_3$ (10 mL). Evaporate the solvent in vacuo, then carefully neutralize with saturated NaHCO$_3$, and extract with EtOAc. Dry over Na$_2$SO$_4$, concentrate under vacuum, and purify by flash chromatography (1:1 hexanes/EtOAc) to obtain 2-chloro-5-trifluoromethylsulfonyl-1H-benzimidazole.

G. 1'-(5-trifluoromethylsulfonyl-1H-benzimidazol-2-yl)-spiro[isobenzofuran-1,4'-piperidin]-3-one

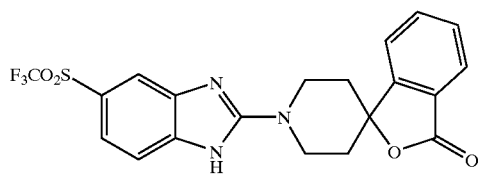

Stir 2-chloro-5-trifluoromethylsulfonyl-1H-benzimidazole (185 mg) and spiro[isobenzofuran-1,4'-piperidin]-3-one (263 mg) in dimethylacetamide (6 mL) at 195° C. for 1 hour. Cool the mixture and partition between EtOAc and half-saturated NaHCO$_3$, wash several times with water, dry and concentrate in vacuo. Purify the residue by chromatography (1:1 hexanes/EtOAc) to obtain 1'-(5-trifluoromethylsulfonyl-1H-benzimidazol-2-yl)-spiro[isobenzofuran-1,4'-piperidin]-3-one.

Example 7

1'-(5-(3-Methoxyphenyl)-1h-Benzimidazol-2-Y1)-Spiro[Isobenzofuran-1,4'-Piperidin]-3-One This Example illustrates the preparation of the representative compound 1'-(5-(3-methoxyphenyl)-1H-benzimidazol-2-yl)-spiro[isobenzofuran-1,4'-piperidin]-3-one.

A. 5-(3-methoxyphenyl)-2-aminobenzoic acid

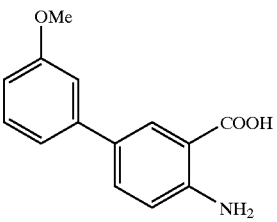

To a solution of 5-iodo-2-aminobenzoic acid (2.6g; 10 mmol) in ethylene glycol dimethyl ether (DME, 20 mL) add tetrakis(triphenylphosphine)palladium(0) (150 mg) under argon. After the catalyst dissolved completely, add successively 3-methoxybenzeneboronic acid (1.65 g; 11 mmol) and sodium carbonate (1M in water, 30 mL). Heat the mixture at 80° C. for 1 hour. Cool the reaction mixture then wash with 50% EtOAc in hexane. Filter the aqueous layer through a short pad of celite to remove palladium black and carefully pour the filtrate into cold 3N hydrochloric acid (25 mL) under stirring. Collect the precipitate by filtration and air-dry to obtain 5-(3-methoxyphenyl)-2-aminobenzoic acid as a white solid.

B. 5-(3-Methoxyphenyl)benzimidazolidin-2-one

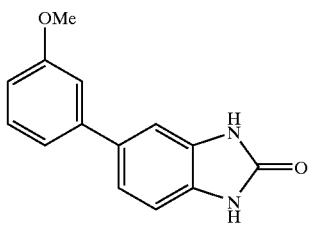

To a suspension of 5-(3-methoxyphenyl)-2-aminobenzoic acid (2.0g) in 1,4-dioxane (20 mL) add N-methylpyrolidinone (NMP, 5 mL) and triethylamine (1.4 mL), followed by diphenyl phosphoric azide (DPPA, 2.5 g). After stirring at ambient temperature for 30 minutes, heat the mixture to 100° C. for 2 hours, until gas evolution fully subsided. Cool the mixture to ambient temperature and concentrate in vacuo. Dissolve the residue in MeOH and leave to stand for 18 hours. Filter the precipitate and air dry to obtain 5-(3-methoxyphenyl)benzimidazolidin-2-one as a pale yellow solid.

C. 2-Chloro-5-(3-methoxyphenvl)benzimidazole

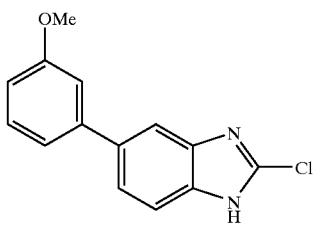

Heat a mixture of 5-(3-methoxyphenyl)benzimidazolidin-2-one (1.4 g) and tetramethylammonium chloride (ca. 2 g) in phosphorous oxychloride at 100° C. for 8 hours. After cooling, concentrate the mixture in vacuo, triturate with water, and neutralize with ammonium hydroxide. Collect the precipitate and air-dry to obtain 2-chloro-5-(3-methoxyphenyl)benzimidazole.

D. 1'-(5-(3-methoxyphenyl)-1H-benzimidazol-2-yl)-spiro[isobenzofuran]-1,4'-piperidin-3-one

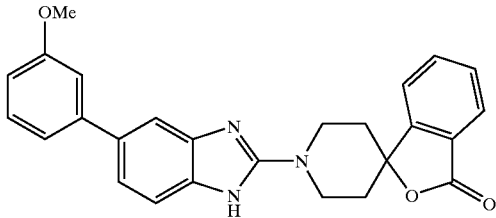

Stir 2-chloro-5-(3-methoxyphenyl)benzimidazole (185 mg) and spiro[isobenzofuran-1,4'-piperidin]-3-one (263 mg) in dimethylacetamide (6 mL) at 195° C. for 1 hour. Cool the mixture and partition between EtOAc and half-saturated NaHCO₃, wash several times with water, dry and concentrate in vacuo. Purify the residue by chromatography (1:1 hexanes/EtOAc) to obtain 1'-(5-(3-methoxyphenyl)-1H-benzimidazol-2-yl)-spiro[isobenzofuran-1,4'-piperidin]-3-one.

Example 8

1'-(5-Phenyl-1h-Imidazo[4,5-B]Pyrazin-2-Y1)-Spiro[Isobenzofuran-1,4'-Piperidin]-3-One This Example illustrate the preparation of the representative compound 1'-(5-Phenyl-1H-imidazo[4,5-b]pyrazin-2-yl)-spiro[isobenzofuran-1,4'-piperidin]-3-one.

A. 2-Amino-5-phenyl-nicotinic Acid Hydrazide

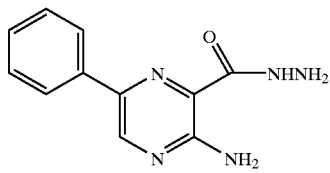

Reflux 3-amino-6-phenyl-pyrazine-2-carboxylic acid methyl ester (1.0 g; Thompson (1988) J. Org. Chem. 53:2052) in hydrazine monohydrate (10 mL) for 2 hours. Cool to room temperature and collect 2-amino-5-phenyl-nicotinic acid hydrazide as a white solid.

B. 5-Phenyl-1,3-dihydro-imidazo[4,5-b]pyrazin-2-one

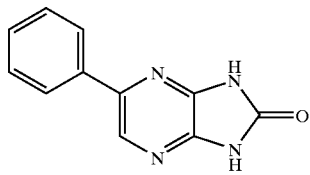

Cool a mixture of 2-amino-5-phenyl-nicotinic acid hydrazide (229 mg, 1.0 mmol) in 2N HCl (5 mL) to 10° C., and add sodium nitrite (138 mg, 2.0 mmol). Let stir at 60° C. for 20 minutes, then cool to room temperature. Basify the mixture with 1M NaOH (10 mL), and collect 5-phenyl-1,3-dihydro-imidazo[4,5-b]pyrazin-2-one as a white solid.

C. 2-Chloro-5-phenyl-1H-imidazo[4,5-b]pyrazine

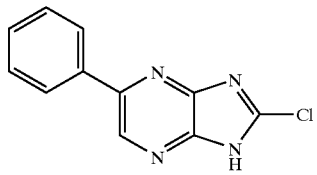

Reflux a solution of 5-phenyl-1,3-dihydro-imidazo[4,5-b]pyrazin-2-one (200 mg) in phosphorus oxychloride (10 mL) for 18 hours. After cooling, remove the excess POCl₃ in vacuo, and triturate the residue in ice-water (200 mL). After stirring for 30 minutes, filter the precipitate to obtain 2-chloro-5-phenyl-1H-imidazo[4,5-b]pyrazine as a gray solid.

D. 1'-(5-Phenyl-1H-imidazo[4,5-b]pyrazin-2-yl)-spiro[isobenzofuran-1,4'-piperidin]-3-one

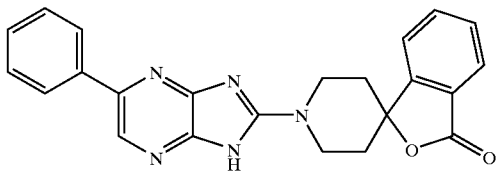

Stir 2-chloro-5-phenyl-1H-imidazo[4,5-b]pyrazine (231 mg, 1 mmol) and spiro[isobenzofuran-1,4'-piperidin]-3-one (406 mg, 2 mmol) in dimethylacetamide (5 mL) at 120° C. for 14 hours. Cool the mixture and partition between EtOAc and half-saturated NaHCO₃, wash several times with water, dry and concentrate in vacuo. Purify by chromatography (1:1 hexanes/EtOAc) to obtain 1'-(5-Phenyl-1H-imidazo[4,5-b]pyrazin-2-yl)-spiro[isobenzofuran-1,4'-piperidin]-3-one as a tan solid.

Example 9

1'-(6-Trifluoromethyl-3-H-Imidazo[4,5-B]Pyridine-2-Y1)-Spiro[Isobenzofuran-1,4'-Piperidin]-3-One This Example illustrates the preparation of the representative compound 1'-(6-trifluoromethyl-3-H-imidazo[4,5-b]pyridine-2-yl)-spiro[isobenzofuran-1,4'-piperidin]-3-one.

A. 5-Trifluoromethyl-pyridine-2,3 Diamine

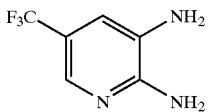

Add 10% Pd/C (0.5 g) to a solution of 3 nitro-5-(trifluoromethyl) pyridin-2-amine (1.0 g, 4.83 mmol) in ethanol (10 mL). Hydrogenate the mixture at a pressure of 50 psi for 5 hours. Filter the mixture through celite, evaporate to dryness under reduced pressure to obtain 5-trifluoromethyl-pyridine-2,3 diamine.

B. 6-Trifluoromethyl-1,3-dihydro-imidazo[4,5-b]pyridin-2-one

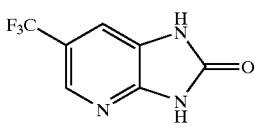

Add 1,1'-carbonyldiimidazole (1.0 g, 6.17 mmol) to a solution of 5-trifluoromethyl-pyridine-2,3 diamine (0.90 g, 5.08 mmol) in CH₂Cl₂ (10 mL) and stir at room temperature for 18 hours. Heat the solution to reflux for 2 hours and filter the precipitate to obtain 6-trifluoromethyl-1,3-dihydro-imidazo[4,5-b]pyridin-2-one.

C. 2-Chloro-6-trifluoromethyl-3-H-imidazo[4,5-b]pyridine

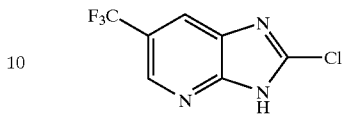

Heat a solution of 6-trifluoromethyl-1,3-dihydro-imidazo[4,5-b]pyridin-2-one. (0.6 g, 2.95 mmol) and tetramethylammonium chloride (0.3 g) to 110° C. in phosphorus oxychloride (10 mL) for 10 hours. After cooling, remove the excess POCl₃ in vacuo, and then neutralize with saturated NaHCO₃, extract with EtOAc. Dry over Na₂SO₄, concentrate under vacuum to obtain 2-chloro-6-trifluoromethyl-3-H-imidazo[4,5-b]pyridine.

D. 1'-(6-trifluoromethyl-3-H-imidazo[4,5-b]pyridine-2-yl)-spiro [isobenzofuran-1,4'-piperidin-3-one

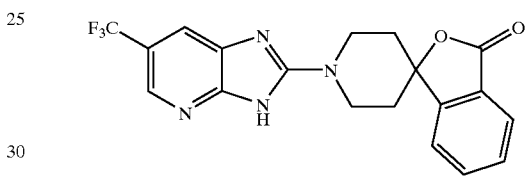

Heat a solution of 2-chloro-6-trifluoromethyl-3-H-imidazo[4,5-b]pyridine (0.1 g, 0.45 mmol) and spiro[isobenzofuran-1,4'-piperidin]-3-one (0.2 g, 0.90 mmol) in dry NMP (5 mL) at 100° C. for 10 hours. Pour the cooled mixture into water (20 mL) and extract twice with EtOAc (20 mL). Wash the combined extracts with brine (20 mL), dry, and evaporate in vacuo. Purify by preparative TLC (4% MeOH-CH₂Cl₂) to obtain 1'-(6-trifluoromethyl-3-H-imidazo[4,5-b]pyridine-2-yl)-spiro[isobenzofuran-1,4'-piperidin]-3-one as a yellow solid.

Example 10

6-Bromo-2-(Spiro[Isobenzofuran-1,4'-Piperidin]-3-One)-3h-Imidazo[4,5-B]Pyridine Hydrochloride This Example illustrate the preparation of the representative compound 6-Bromo-2-(spiro[isobenzofuran-1,4'-piperidin]-3-one)-3H-imidazo[4,5-b]pyridine hydrochloride.

A. 6-Bromo-2-chloro-3H-imidazo[4,5-b]pyridine

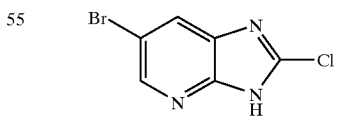

Reflux 6-bromo-1,3-dihydro-imidazo[4,5-b]pyridin-2-one (5 g) for 14 h in POCl₃ (50 mL). Evaporate the solvent in vacuo, then carefully neutralize with saturated NaHCO₃, and extract with EtOAc. Dry over Na₂SO₄, concentrate under vacuum, and purify by flash chromatography (1 :1 hexanes/EtOAc) to obtain 6-bromo-2-chloro-3H-imidazo[4,5-b]pyridine.

B. 6-Bromo-2-(spiro)isobenzofuran-1,4'piperidin-3-one-3H-imidazo[4,5-b]pyridine

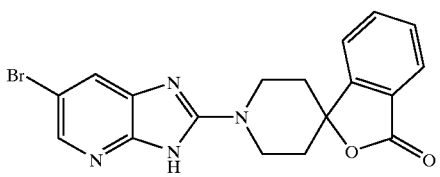

Stir 2-chloro-5-trifluoromethyl-1H-benzimidazole (3 g) and spiro[isobenzofuran-1,4'-piperidin]-3-one (5.8 g) in dimethylacetamide (75 mL) at 120° C. for 14 hours. Cool the mixture and partition between EtOAc and half-saturated NaHCO₃, wash several times with water, dry and concentrate in vacuo. Crystallize in EtOAc/EtOH to obtain a white solid. Dissolve the solid in EtOAc and treat with saturated EtOAc/HCl. Collect 6-bromo-2-(spiro[isobenzofuran-1,4'piperidin]-3-one-3H-imidazo[4,5-b]pyridine hydrochloride.

Example 11

1'-(5-Chloro-3h-Imidazo[4,5-B]Pyridine-2-Y1)-Spiro[Isobenzofuran-1,4'-Piperidin]-3-One This Example illustrates the preparation of the representative compound 1'-(5-chloro-3H-imidazo[4,5-b]pyridine-2-yl)-spiro[isobenzofuran-1,4'-piperidin]-3-one.

A. 6-chloro-3-nitropyridin-2-yl-amine

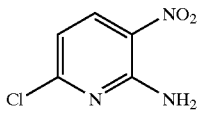

Add sodium carbonate (14 g, 130 mmol) and 2M NH3 in EtOH (20 mL) to a solution of 2,6-dichloro-3-nitropyridine (10 g, 51.8 mmol) in ethanol (115 mL). Heat the mixture at 70° C. for 5 hours. After cooling, remove the excess ethanol in vacuo, and triturate the residue in water. After stirring for 15 minutes, filter the precipitate to obtain 6-chloro-3-nitropyridin-2-yl-amine.

B. 6-Chloro-pyridine-2,3-diamine

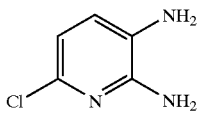

Add zinc (4.0 g) to a solution of 6-chloro-3-nitropyridin-2-yl-amine (1.0 g, 5.76 mmol) in acetic acid (1.5 mL) and methanol (40 mL). Stir the resulting mixture is at room temperature for 18 hours, and filter through a pad of celite. Evaporate the filtrate to dryness under reduced pressure. Treat the resulting residue with 1N aqueous NaOH and extract with EtOAc. Wash the EtOAc extract with water and saturated aqueous NaCl. Separate the organic layer, dry over Na₂SO₄, filter and concentrate. Purify by flash column chromatography (50% EtOAc-hexane) to obtain 6-chloro-pyridine-2,3-diamine.

C. 5-Chloro-1,3-dihydro-imidazole[4,5-b]pyridin-2-one

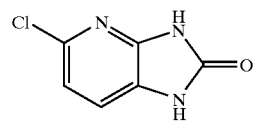

Add 1,1'-carbonyldiimidazole (0.1 g, 0.70 mmol) to a solution of 6-chloro-pyridine-2,3-diamine (0.1 g, 0.70 mmol) in CH₃CN (3 mL) and heat at 60° C. for 18 hours. Cool to ambient temperature and filter the precipitate to obtain 5-chloro-1,3-dihydro-imidazole[4,5-b]pyridin-2-one.

D. 2,5-Dichloro-3H-imidazo[4,5-b]pyridine

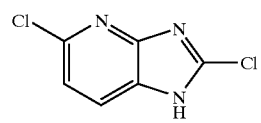

Heat a solution of 5-chloro-1,3-dihydro-imidazole[4,5-b]pyridin-2-one. (0.07 g, 0.42 mmol) and tetramethylammonium chloride (0.1 g) is to 115° C. in phosphorus oxychloride (10 mL) for 10 hours. After cooling, remove the excess POCl₃ in vacuo, and then neutralize with saturated NaHCO₃, and extract with EtOAc. Dry over Na₂SO₄, concentrate under vacuum to obtain 2,5-dichloro-3H-imidazo[4,5-b]pyridine.

E. 1'-(5-chloro-3H-imidazo[4,5-b]pyridine-2-yl)-spiro[isobenzofuran-1,4'-piperidin]-3-one

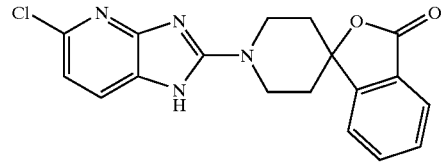

Heat a solution of 2,5-dichloro-3H-imidazo[4,5-b]pyridine (0.07 g, 0.37 mmol) and spiro[isobenzofiiran-1,4'-piperidin]-3-one (0.15 g, 0.74 mmol) in dry NMP (3 mL) at 100° C. for 14 hours. Pour the cooled mixture into water (10 mL) and extract twice with EtOAc (10 mL). Wash the combined extracts with brine (10 mL), dry, and evaporate in vacuo. Purify by preparative TLC (5% MeOH-CH₂Cl₂) to obtain 1'-(5-chloro-3H-imidazo[4,5-b]pyridine-2-yl)-spiro[isobenzofuran-1,4'-piperidin]-3-one as a white solid.

Example 12

1'-(6-Iodo-1h-Quinazolin-4-On-2-Y1)-Spiro[Isobenzofuran-1,4'-Piperidin]1-3-One This Example illustrates the preparation of the representative compound 1'-(6-iodo-1H-quinazolin-4-on-2-yl)-spiro[isobenzofuran-1,4'-piperidin]-3-one.

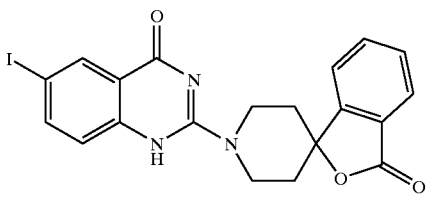

Stir 2-chloro-6-iodo-1H-quinazolin-4-one (75 mg) and spiro[isobenzofuran-1,4'-piperidin]-3-one (100 mg) in NMP (2 mL) at 110° C. for 6 h. Cool the mixture and pour in ice-water (20 mL). After stirring for 5 min, filter the precipitate and wash with MeOH to obtain 1'-(6-iodo-1H-quinazolin-4-on-2-yl)-spiro [isobenzofiran-1,4'-piperidin]-3-one.

Example 13

1'-(4-Trifluoromethyl-Phenylcarbamoyl)-Spiroisobenzofuran-1,4'-Piperidine

This Example illustrare the preparation of the representative compound 1'-(4-Trifluoromethyl-phenylcarbamoyl)-spiroisobenzofuran-1,4'-piperidine.

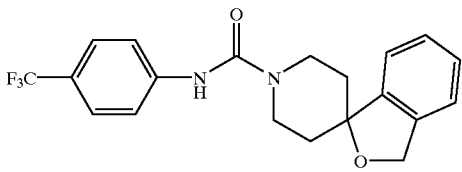

Stir a mixture of trifluoro-p-tolyl isocyanate (1.87 g, 10.0 mmol) and spiroisobenzofuran-1,4'-piperidine (1.89 g, 10 mmol) in toluene. After 2 h, collect 1'-(4-trifluoromethyl-phenylcarbamoyl)-spiroisobenzofuran-1,4'-piperidine as a colorless solid.

Example 14

1'-(5-Trifluoromethyl-Pyridin-2-Y1-Carbamoyl)-Spiroisobenzofuran-1,4'-Piperidine This Example illustrates the preparation of the representative compound 1'-(5-Trifluoromethyl-pyridin-2-yl-carbamoyl)-spiroisobenzofuran-1,4'-piperidine.

A. Trifluoromethyl-pyridin-2-yl)-carbamic Acid Phenyl Ester

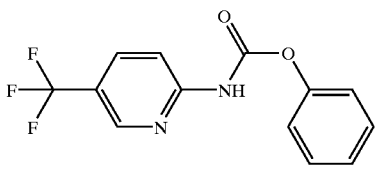

Dissolve 2-amino-5-trifluoromethylpyridine (162 mg, 1.0 mmole) in pyridine (2.0 mL) under nitrogen at room temperature. Add drop wise phenyl chloroformate (0.125 mL, 1.0 mmole) to the reaction mixture at room temperature. Stir the mixture for 24 hours and new spot is noticed in TLC (30% EtOAc/hexane). Evaporate the reaction mixture under vacuo and purify the crude by flash column chromatography on a silica gel using CHCl₃ to afford (5-Trifluoromethyl-pyridin-2-yl)-carbamic acid phenyl ester as a white solid.

B. 1'-(5-Trifluoromethyl-pyridin-2-yl-carbamoyl)spiroisobenzofuran-1,4'-piperidine

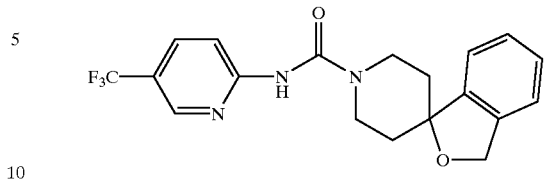

Dissolve (5-Trifluoromethyl-pyridin-2-yl)-carbamic acid phenyl ester (420 mg, 1.49 mmol), spiroisobenzofuran-1,4'-piperidine (282 mg, 1.49 mmol) and triethylamine (415 µL, 2.98 mmol) in dry CHCl₃ and reflux overnight under a nitrogen atmosphere. Cool the solution, dilute with CH₂Cl₂ and wash sequentially with 10% NaOH (3X) and brine (1X). Dry the solution (Na₂SO₄) and concentrate under reduced pressure. Stir the resulting solid with ether until a free-flowing powder is obtained, collect in a sintered glass funnel and wash with ether followed by hexanes to obtain 1'-(5-trifluoromethyl-pyridin-2-yl-carbamoyl)spiroisobenzofuran-1,4'-piperidine as an off-white solid.

Example 15

1'-(1,4-Dioxa-Spiro[4.5]Dec-8-Y1-Carbamoyl)-SpirorIsobenzofuran-1,4'-Piperidin-3-One This Example illustrates the preparation of the representative compound 1'-(1,4-dioxa-spiro[4.5]dec-8-yl-carbamoyl)-spiro[isobenzofuran-1,4'-piperidin]-3-one.

A. (1,4-dioxa-spiro[4.51]dec-8-yl)-carbamoyl Chloride

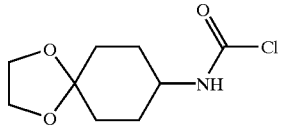

Dissolve 1,4-dioxaspiro[4.5]decan-8-amine (785 mg, 0.005 mol; see Liebigs (1990) Ann. Chem. 8:781–7) in CH₂Cl₂ and then add H₂O (20 mL) followed by saturated NaHCO₃ solution (50 mL). Add a toluene solution of phosgene (20% solution, 5 mL) to the reaction mixture and stir at room temperature for 1 hour. Dry the CH₂Cl₂ layer (Na₂SO₄) and concentrate under reduced pressure. Dissolve the resulting oil in dry toluene to produce a stock solution (~0.2 M) of (1,4-dioxa-spiro[4.5]dec-8-yl)-carbamoyl chloride.

B. 1'-(1,4-dioxa-spiro[4.51]dec-8-yl-carbamoyl-spiro[isobenzofuran-1,4'-piperidin]-3-one

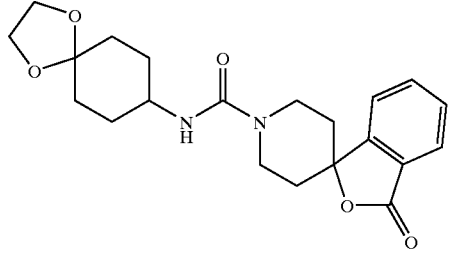

Add spiro[isobenzofuran-1,4'-piperidin]-3-one (100 mg, 0.49 mmol) to 1 mL of the stock solution of (1,4-dioxa-spiro[4.5]dec-8-yl)-carbamoyl chloride (~0.2 M in toluene)

and heat to 60° C. for 16 hours. Cool the solution, dilute with EtOAc and wash with brine. Dry the solution ($Na_2SO_4$) and concentrate under reduced pressure. Purify the crude product using preparative plate chromatography and triturate the resulting material with ether to obtain 1'-(1,4-dioxa-spiro [4.5]dec-8-yl-carbamoyl)-spiro[isobenzofuran-1,4'-piperidin]-3-one as a white solid.

Example 16

1'-(Trans-4-Carboxy-Cyclohexylmethyl)Carbamoyl-Spiro[Isobenzofuran-1,4'piperidin]-3-One This Example illustrate the preparation of the representative compound 1'-(trans-4-Carboxy-cyclohexylmethyl) carbamoyl-spiro [isobenzofuran-1,4'piperidin]-3-one.

A. 1'-(trans-4-Ethoxycarbonyl-cyclohexylmethyl) carbamoyl-spiro [isobenzofuran-1,4'piperidin]3-one

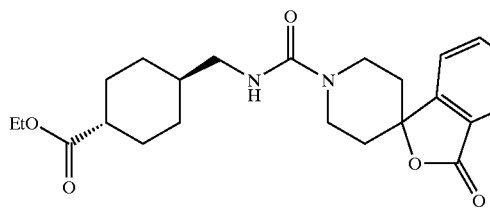

Add spiro[isobenzofuran-1,4'-piperidin]-3-one (100 mg, 0.49 mmol) to 1 mL of a ~0.2 M stock solution of 1'-(trans-4-ethoxycarbonyl-cyclohexylmethyl) carbamoyl chloride (prepared from trans-4-aminomethyl-cyclohexanecarboxylic acid ethyl ester using the same procedure given in Example 15 step A) and heat to 60° C. for 16 hours. Cool the solution, dilute with EtOAc and wash with brine. Dry the solution ($Na_2SO_4$) and concentrate under reduced pressure. Purify the crude product using preparative plate chromatography and triturate the resulting material with ether to obtain 1'-(trans-4-ethoxycarbonyl-cyclohexylmethyl)carbamoyl-spiro[isobenzofuran-1,4'piperidin]-3-one as a white solid.

B. 1'-(trans-4-Carboxy-cyclohexylmethyl carbamoyl-spiro [isobenzofuran-1,4'piperidin]-3-one

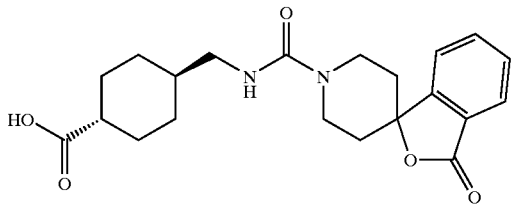

Dissolve 1'-(trans-4-ethoxycarbonyl-cyclohexylmethyl) carbamoyl-spiro[isobenzofuran-1,4'piperidin]-3-one (21 mg, 0.05 mmol) in THF (2 mL) and add an equal volume of water. Add LiOH•$H_2O$ (11 mg, 0.26 mmol) to this mixture and heat at 60° C. for 3 hours with stirring. Evaporate the THF under reduced pressure, dilute the residue with water and acidify with 3N HCL. Extract the aqueous mixture with EtOAc, wash with brine, dry ($Na_2SO_4$) and concentrate under reduced pressure to obtain 1'-(trans-4-carboxy-cyclohexylmethyl)carbamoyl-spiro[isobenzofuran-1,4'piperidin]-3-one as a white solid.

Example 17

1'-(6-Piperidyl-Pyridin-3-Y1-Carbamoyl)-Spiroisobenzoftiran-1,4'-Piperidine

This Example illustrates the preparation of the representative compound 1'-(6-piperidyl-pyridin-3-yl-carbamoyl)-spiroisobenzofuran-1,4'-piperidine.

A. (3,4,5,6-Tetrahydro-2H-[1,2']bipyridinyl-5'-yl)-carbamic Acid Phenyl Ester

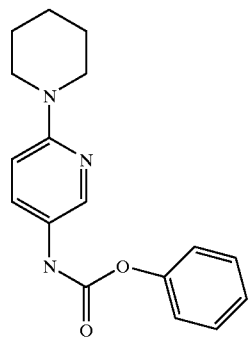

3,4,5,6-Tetrahydro-2H-[1,2']bipyridinyl-5'-ylamine (1.01 g, 5.7 mmol) and pyridine (12 ml) are stirred in dry $CH_2Cl_2$. Phenylchloroformate (1.3 g, 8.5 mmol) is added to this mixture and stirred for 24 h at room temperature. Water and a solution of 1:1 EtOAc/hexanes is added and the organic layer is separated. The organic layer is washed with 1N HCl three times and with brine once. The organic layer is dried over $Na_2SO_4$, filter, and evaporated in vacuo. Purify by flash column chromatography (0–10% EtOAc/$CH_2Cl_2$) to obtain (3,4,5,6-tetrahydro-2H-[1,2']bipyridinyl-5'-yl)-carbamic acid phenyl ester. Mass spec.: M–1=280 ($AP^-$).

B. 1'(6-piperidyl-pyridin-3-yl-carbamoyl)-spiroisobenzofiran-1,4'-piperidine

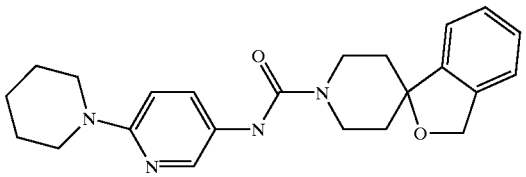

A solution of spiroisobenzofuran-1,4'-piperidine (0.047 g, 0.25 mmol), (3,4,5,6-tetrahydro-2H-[1,2']bipyridinyl-5'-yl)-carbamic acid phenyl ester (0.056 g, 0.19 mmol), and triethylamine (0.052 g, 0.51 mmol) is heated in 1 ml of dry chloroform to 61° C. for 1.5 h. 2 ml of saturated $NaHCO_3$ is added to the cooled reaction mixture and the mixture extracted 2 times with $CH_2Cl_2$. The organic layers are combined, dried over $Na_2SO_4$, and evaporated in vacuo. Purify by flash column chromatography (3–5% methanol/ $CH_2Cl_2$) to obtain 1'-(6-piperidyl-pyridin-3-yl-carbamoyl)-spiroisobenzofuran-1,4'-piperidine. Mass spec.: M+1=393 ($AP^+$).

Example 18

1'-(6-Methoxy-Pyridin-3-Y1-Carbamoyl)-Spiroisobenzofuran-1,4'-Piperidine

This Example illustrates the preparation of the representative compound 1'-(6-methoxy-pyridin-3-yl-carbamoyl)-spiroisobenzofuran-1,4'-piperidine.

A. (6-Methoxy-pyridin-3-yl)-carbamic Acid Phenyl Ester

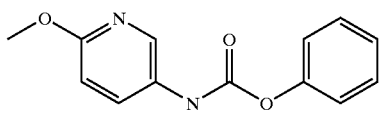

6-Methoxy-pyridin-3-ylamine (1.0 g, 8.06 mmol) and pyridine (18 ml) are stirred in dry $CH_2Cl_2$. To this mixture phenylchloroformate (1.9 g, 12.0 mmol) is added and stirred for 24 hours at room temperature. Water and a solution of 1:1 EtOAc/hexanes is added to the mixture and the organic layer is separated. The organic layer is washed with 1N HCl three times and with brine once. The organic layer is dried over $Na_2SO_4$, filtered, and evaporated in vacuo. Purify by flash column chromatography (0–10% EtOAc/$CH_2Cl_2$) to obtain (6-methoxy-pyridin-3-yl)-carbamic acid phenyl ester. Mass spec.: m+1=245 ($AP^+$)

B. 1'-(6-methoxy-pridin-3-yl-carbamoyl)-spiroisobenzofuran-1,4'-piperidine

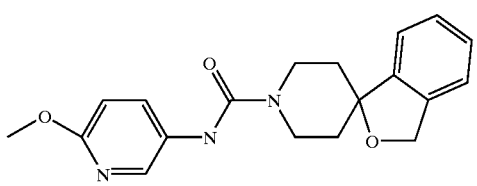

A solution of spiroisobenzofuran-1,4'-piperidine (0.047 g, 0.25 mmol), (6-methoxy-pyridin-3-yl)-carbamic acid phenyl ester (0.046 g, 0.19 mmol), and triethylamine (0.052 g, 0.51 mmol) in 1 ml of dry chloroform is heated to 61° C. for 1.5 hours. 2 ml of saturated $NaHCO_3$ is added to the cooled reaction mixture and the mixture is extracted 2 times with $CH_2Cl_2$. The organic layers are combined, dried over $Na_2SO_4$, and evaporated in vacuo. Purify by flash column chromatography (3–5% methanol/$CH_2Cl_2$) to obtain 1'-(6-methoxy-pyridin-3-yl-carbamoyl)-spiroisobenzofuran-1,4'-piperidine. Mass spec.: M+1=340 ($AP^+$).

Example 19

1'-(5-Methyl-Pyridin-2-Y1-Carbamoyl)-Spiroisobenzofuran-14'-Piperidine

This Example illustrates the preparation of the representative compound 1'-(5-methyl-pyridin-2-yl-carbamoyl)-spiroisobenzofuran-1,4'-piperidine.

A. (5-Methyl-pyridin-2-yl)-carbamic Acid Phenyl Ester

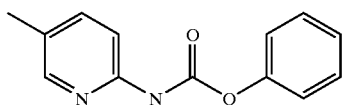

To a stirring mixture of 5-methyl-pyridin-2-ylamine (1.0 g, 9.25 mmol) and pyridine (20 ml) in dry $CH_2Cl_2$ add phenylchloroformate (2.2 g, 13.9 mmol) and stir for 24 hours at room temperature. Add water and a solution of 1:1 EtOAc/hexanes and separate the organic layer. Wash the organic layer with 1N HCl three times and with brine once. Dry the organic layer over $Na_2SO_4$, filter, and evaporate in vacuo. Purify by flash column chromatography (0–10% EtOAc/$CH_2Cl_2$) to obtain (5-methyl-pyridin-2-yl)-carbamic acid phenyl ester. Mass spec.: M+1=229 ($AP^+$).

B. 1'-(5-methyl-pyridin-2-yl-carbamoyl)-spiroisobenzofuran-1,4'-piperidine

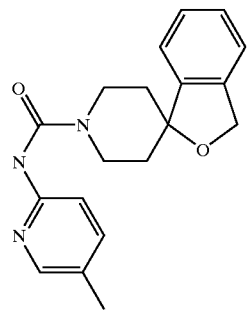

Heat a solution of spiroisobenzofuran-1,4'-piperidine (0.047 g, 0.25 mmol), (5-methyl-pyridin-2-yl)-carbamic acid phenyl ester (0.042 g, 0.19 mmol), and triethylamine (0.052 g, 0.51 mmol) in 1 ml of dry chloroform to 61° C. for 1.5 hours. Add 2 ml of saturated $NaHCO_3$ to the cooled reaction mixture and extract 2 times with $CH_2Cl_2$. Combine the organics, dry over $Na_2SO_4$, and evaporate in vacuo. Purify by flash column chromatography (3–5% methanol/$CH_2Cl_2$) to obtain 1'-(5-methyl-pyridin-2-yl-carbamoyl)-spiroisobenzofuran-1,4'-piperidine. Mass spec.: M+1=324 ($AP^+$).

Example 20

1'-(6-pyrrolidin-pyridin-3-yl-carbamoyl)-spiroisobenzofuran-1,4'-piperidine This Example illustrates the preparation of the representative compound 1'-(6-pyrrolidin-pyridin-3-yl-carbamoyl)-spiroisobenzofuran-1,4'-piperidine.

A. 5-Nitro-2-pyrrolidin-1-yl-pyridine

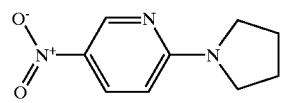

To a stirring mixture of 2-chloro-5-nitropyridine (5.0 g, 31.5 mmol), potassium carbonate (7.0 g, 50.4 mmol), in 65 ml of DMF add pyrrolidine (6.7 g, 95 mmol) and stir at room temperature for 72 h. Dilute reaction mixture with 100 ml EtOAc and wash 2 times with 100 ml saturated $NaHCO_3$, and 2 times with 100 ml of brine. Dry organics over $Na_2SO_4$, and evaporate in vacuo to obtain 5-nitro-2-pyrrolidin-1-yl-pyridine. Mass spec.: m+1=194 ($AP^+$).

B. 6-Pyrrolidin-1-yl-pyridin-3-ylamine

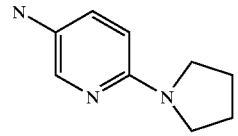

Combine 5-nitro-2-pyrrolidin-1-yl-pyridine (5.6 g, 29 mmol), palladium hydroxide (1.96 g, 35 wt. %), ammonium formate (9.1 g, 145 mmol), 1N HCl/$Et_2O$ (41 ml), in methanol (289 ml) and stir. Heat reaction mixture to reflux for 1 hour. Cool reaction mixture and add carbon to decolorize. Filter the solution through celite, add 50 ml of saturated $NaHCO_3$, and evaporate in vacuo to remove the methanol and ether. Extract the residue 3 times into $CH_2Cl_2$ from saturated $NaHCO_3$, dry over $Na_2SO_4$, and evaporate in vacuo to obtain 6-pyrrolidin-1-yl-pyridin-3-ylamine. Mass spec.: M+1=164 (AP$^+$).

C. 1'-(6-pyrrolidin-pyridin-3-yl-carbamoyl)-spiroisobenzofuran-1,4'-piperidine

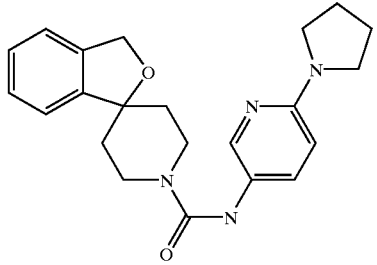

To a stirring solution of spiroisobenzofuran-1,4'-piperidine (0.130 g, 0.688 mmol), 7 ml of $CH_2Cl_2$, and N,N-diisopropylethylamime (0.14 ml, 0.825 mmol) at 0° C., add triphosgene (0.1123 g, 0.3784 mmol). Warm solution to room temperature over 2 hours and add 6-pyrrolidin-1-yl-pyridin-3-ylamine (0.1123 g, 0.688 mmol). Stir at room temperature for 72 hours. Wash reaction mixture with water, dry over $Na_2SO_4$, and evaporate in vacuo. Purify by flash column chromatography (5% methanol/$CH_2Cl_2$) to obtain 1'-(6-pyrrolidin-pyridin-3-yl-carbamoyl)-spiroisobenzofuran-1,4'-piperidine. Mass spec.: M+1=379 (AP$^+$).

Example 21

1'-(5-(3,5-Dimethyl-Isoxazol-4-Y1)-1H-Benzimidazol-2-Y1)-Spiro[Isobenzofuran-1,4'-Piperidin]-3-One This Example illustrates the preparation of the representative compound 1'-(5-(3,5-dimethyl-isoxazol-4-yl)-1H-benzimidazol-2-yl)-spiro[isobenzofuiran-1,4'-piperidin]-3-one.

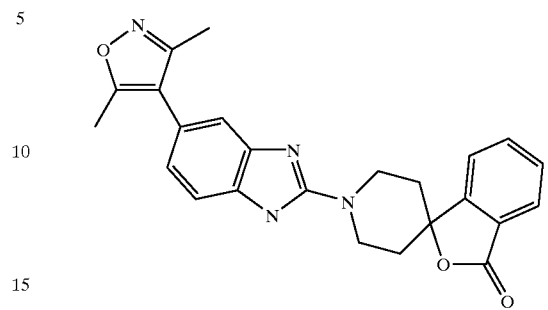

Follow procedure C. in Example 1 using tetrakistriphenylphosphine palladium (0.04 g, 0.034 mmol), 1'-(5-iodo-1H-benzimidazol-2-yl)-spiro[isobenzofuran-1,4'-piperidin]-3-one (0.05 g, 0.112 mmol), 3,5-dimethylisoxazole-4-boronic acid (0.03 g, 0.229 mmol), aqueous sodium carbonate (1M, 0.5 ml), and ethylene glycol dimethyl ether (5 ml). Heat reaction mixture at 80° C. for 24 hours. Purify on J. T. Baker silica gel prep plate (5×20 cm) using 10% methanol/$CH_2Cl_2$ to obtain 1'-(5-(3,5-dimethyl-isoxazole)-1H-benzimidazol-2-yl)-spiro[isobenzofuran-1,4'-piperidin]-3-one. Mass spec.: M+1=415 (AP$^+$).

The preparation of the compounds provided herein by the above-mentioned methods is illustrated further by the following examples, delineated in Tables 1–4, which are not to be construed as limiting the invention in scope or spirit to the specific procedures and compounds described in them. Commonly used abbreviations are: Ph is phenyl, Me is methyl, Et is ethyl, nPr or Pr is n-propyl, iPr is isopropyl, tBu is tert-butyl, cPent is cyclopentyl, cHex is cyclohexyl, EX means example.

TABLE 1

| EX | A | B | C | D | X | Y | Z | R$_1$ |
|---|---|---|---|---|---|---|---|---|
| 22 | C—H | C-[1,2,4]oxadiazol-3-yl | C—H | C—H | O | C—H | C—H | H |
| 23 | C—H | C-[1,2,4]oxadiazol-3-yl | C—H | C—H | CH$_2$ | C—H | C—H | H |
| 24 | C—H | C-[1,2,4]oxadiazol-5-yl | C—H | C—H | O | C—H | C—H | H |
| 25 | C—H | C-[1,2,4]oxadiazol-5-yl | C—H | C—H | CH$_2$ | C—H | C—H | H |
| 26 | C—H | C-[1,3,4]oxadiazol-2-yl | C—H | C—H | O | C—H | C—H | H |
| 27 | C—H | C-[1,3,4]oxadiazol-2-yl | C—H | C—H | CH$_2$ | C—H | C—H | H |
| 28 | C—H | C-2-Me-oxazol-4-yl | C—H | C—H | O | C—H | C—H | H |
| 29 | C—H | C-2-Me-oxazol-4-yl | C—H | C—H | CH$_2$ | C—H | C—H | H |
| 30 | C—H | C-2-Me-oxazol-5-yl | C—H | C—H | O | C—H | C—H | H |
| 31 | C—H | C-2-Me-oxazol-5-yl | C—H | C—H | CH$_2$ | C—H | C—H | H |
| 32 | C—H | C-2-Me-pyrimidin-4-yl | C—H | C—H | O | C—H | C—H | H |
| 33 | C—H | C-2-Me-pyrimidin-4-yl | C—H | C—H | CH$_2$ | C—H | C—H | H |
| 34 | C—H | C-2-Me-pyrimidin-5-yl | C—H | C—H | O | C—H | C—H | H |
| 35 | C—H | C-2-Me-pyrimidin-5-yl | C—H | C—H | CH$_2$ | C—H | C—H | H |
| 36 | C—H | C-2-Me-thiazol-5-yl | C—H | C—H | O | C—H | C—H | H |

TABLE 1-continued

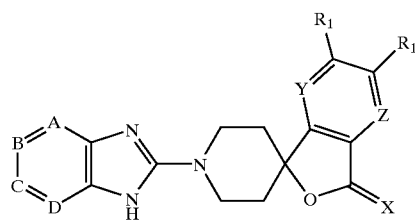

| EX | A | B | C | D | X | Y | Z | R₁ |
|---|---|---|---|---|---|---|---|---|
| 37 | C—H | C-2-Me-thiazol-5-yl | C—H | C—H | CH₂ | C—H | C—H | H |
| 38 | C—H | C-3-Me-[1,2,4]oxadiazol-5-yl | C—H | C—H | O | C—H | C—H | H |
| 39 | C—H | C-3-Me-[1,2,4]oxadiazol-5-yl | C—H | C—H | CH₂ | C—H | C—H | H |
| 40 | C—H | C-3-Me-isoxazol-5-yl | C—H | C—H | O | C—H | C—H | H |
| 41 | C—H | C-3-Me-isoxazol-5-yl | C—H | C—H | CH₂ | C—H | C—H | H |
| 42 | C—H | C-4-Me-oxazol-2-yl | C—H | C—H | O | C—H | C—H | H |
| 43 | C—H | C-4-Me-oxazol-2-yl | C—H | C—H | CH₂ | C—H | C—H | H |
| 44 | C—H | C-4-Me-thiazol-2-yl | C—H | C—H | O | C—H | C—H | H |
| 45 | C—H | C-4-Me-thiazol-2-yl | C—H | C—H | CH₂ | C—H | C—H | H |
| 46 | C—H | C-5-Me-[1,2,4]oxadiazol-3-yl | C—H | C—H | O | C—H | C—H | H |
| 47 | C—H | C-5-Me-[1,2,4]oxadiazol-3-yl | C—H | C—H | CH₂ | C—H | C—H | H |
| 48 | C—H | C-5-Me-[1,3,4]oxadiazol-2-yl | C—H | C—H | O | C—H | C—H | H |
| 49 | C—H | C-5-Me-[1,3,4]oxadiazol-2-yl | C—H | C—H | CH₂ | C—H | C—H | H |
| 50 | C—H | C-5-Me-isoxazol-3-yl | C—H | C—H | O | C—H | C—H | H |
| 51 | C—H | C-5-Me-isoxazol-3-yl | C—H | C—H | CH₂ | C—H | C—H | H |
| 52 | C—H | C-5-Me-pyrazin-2-yl | C—H | C—H | O | C—H | C—H | H |
| 53 | C—H | C-5-Me-pyrazin-2-yl | C—H | C—H | CH₂ | C—H | C—H | H |
| 54 | C—H | C-6-Me-pyrazin-2-yl | C—H | C—H | O | C—H | C—H | H |
| 55 | C—H | C-6-Me-pyrazin-2-yl | C—H | C—H | CH₂ | C—H | C—H | H |
| 56 | C—H | C—Br | C—H | C—H | O | C—H | C—H | H |
| 57 | C—H | C—Br | C—H | C—H | CH₂ | C—H | C—H | H |
| 58 | C—Cl | C—Br | C—H | C—H | O | C—H | C—H | H |
| 59 | C—Cl | C—Br | C—H | C—H | CH₂ | C—H | C—H | H |
| 60 | C—H | C—C=O—Et | C—H | C—H | O | C—H | C—H | H |
| 61 | C—H | C—C=O—Et | C—H | C—H | CH₂ | C—H | C—H | H |
| 62 | C—H | C—C=O-iPr | C—H | C—H | O | C—H | C—H | H |
| 63 | C—H | C—C=O-iPr | C—H | C—H | CH₂ | C—H | C—H | H |
| 64 | C—H | C—C=O—Me | C—H | C—H | O | C—H | C—H | H |
| 65 | C—H | C—C=O—Me | C—H | C—H | CH₂ | C—H | C—H | H |
| 66 | C—H | C—C=O-nPr | C—H | C—H | O | C—H | C—H | H |
| 67 | C—H | C—C=O-nPr | C—H | C—H | CH₂ | C—H | C—H | H |
| 68 | C—H | C—C=O—Ph | C—H | C—H | O | C—H | C—H | H |
| 69 | C—H | C—C=O—Ph | C—H | C—H | CH₂ | C—H | C—H | H |
| 70 | C—H | C—C=O-tBu | C—H | C—H | O | C—H | C—H | H |
| 71 | C—H | C—C=O-tBu | C—H | C—H | CH₂ | C—H | C—H | H |
| 72 | C—H | C—CF₃ | C—H | C—H | O | C—H | C—H | H |
| 73 | C—H | C—CF₃ | C—H | C—H | CH₂ | C—H | C—H | H |
| 74 | C—H | C—CF₃ | C—F | C—H | O | C—H | C—H | H |
| 75 | C—H | C—CF₃ | C—F | C—H | CH₂ | C—H | C—H | H |
| 76 | C—H | C—CF₃ | C—H | N | O | C—H | C—H | H |
| 77 | C—H | C—CF₃ | C—H | N | CH₂ | C—H | C—H | H |
| 78 | N | C—CF₃ | C—H | N | O | C—H | C—H | H |
| 79 | N | C—CF₃ | C—H | N | CH₂ | C—H | C—H | H |
| 80 | C—H | C—CF₃ | N | C—H | O | C—H | C—H | H |
| 81 | C—H | C—CF₃ | N | C—H | CH₂ | C—H | C—H | H |
| 82 | N | C—CF₃ | N | C—H | O | C—H | C—H | H |
| 83 | N | C—CF₃ | N | C—H | CH₂ | C—H | C—H | H |
| 84 | C—H | C-cHex | C—H | C—H | O | C—H | C—H | H |
| 85 | C—H | C-cHex | C—H | C—H | CH₂ | C—H | C—H | H |
| 86 | C—H | C—Cl | C—H | C—H | O | C—H | C—H | H |
| 87 | C—H | C—Cl | C—H | C—H | CH₂ | C—H | C—H | H |
| 88 | C—H | C—Cl | C—H | C—Cl | O | C—H | C—H | H |
| 89 | C—H | C—Cl | C—H | C—Cl | CH₂ | C—H | C—H | H |
| 90 | C—H | C—Cl | C—H | N | O | C—H | C—H | H |
| 91 | C—H | C—Cl | C—H | N | CH₂ | C—H | C—H | H |
| 92 | N | C—Cl | C—H | N | O | C—H | C—H | H |
| 93 | N | C—Cl | C—H | N | CH₂ | C—H | C—H | H |
| 94 | C—H | C—CN | C—H | C—H | O | C—H | C—H | H |
| 95 | C—H | C—CN | C—H | C—H | CH₂ | C—H | C—H | H |
| 96 | C—H | C—CN | C—H | N | O | C—H | C—H | H |
| 97 | C—H | C—CN | C—H | N | CH₂ | C—H | C—H | H |
| 98 | N | C—CN | C—H | N | O | C—H | C—H | H |
| 99 | N | C—CN | C—H | N | CH₂ | C—H | C—H | H |
| 100 | C—H | C—CO₂Me | C—H | C—H | O | C—H | C—H | H |
| 102 | C—H | C—CO₂Me | C—H | C—H | CH₂ | C—H | C—H | H |

TABLE 1-continued

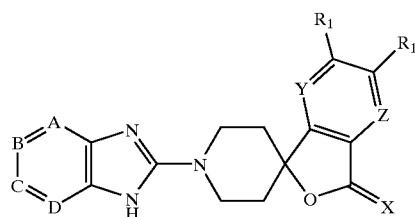

| EX | A | B | C | D | X | Y | Z | R₁ |
|---|---|---|---|---|---|---|---|---|
| 102 | C—H | C—CONEt₂ | C—H | C—H | O | C—H | C—H | H |
| 103 | C—H | C—CONEt₂ | C—H | C—H | CH₂ | C—H | C—H | H |
| 104 | C—H | C—CONHMe | C—H | C—H | O | C—H | C—H | H |
| 105 | C—H | C—CONHMe | C—H | C—H | CH₂ | C—H | C—H | H |
| 106 | C—H | C—CONMe₂ | C—H | C—H | O | C—H | C—H | H |
| 107 | C—H | C—CONMe₂ | C—H | C—H | CH₂ | C—H | C—H | H |
| 108 | C—H | C-cPent | C—H | C—H | O | C—H | C—H | H |
| 109 | C—H | C-cPent | C—H | C—H | CH₂ | C—H | C—H | H |
| 110 | C—H | C—Et | C—H | C—H | O | C—H | C—H | H |
| 111 | C—H | C—Et | C—H | C—H | CH₂ | C—H | C—H | H |
| 112 | C—H | C—F | C—H | C—H | O | C—H | C—H | H |
| 113 | C—H | C—F | C—H | C—H | CH₂ | C—H | C—H | H |
| 114 | C—H | C—F | C—F | C—H | O | C—H | C—H | H |
| 115 | C—H | C—F | C—F | C—H | CH₂ | C—H | C—H | H |
| 116 | C—H | C—F | C—H | N | O | C—H | C—H | H |
| 117 | C—H | C—F | C—H | N | CH₂ | C—H | C—H | H |
| 118 | C—CF₃ | C—H | C—H | C—H | O | C—H | C—H | H |
| 119 | C—CF₃ | C—H | C—H | C—H | CH₂ | C—H | C—H | H |
| 120 | C—Cl | C—H | C—H | C—H | O | C—H | C—H | H |
| 121 | C—Cl | C—H | C—H | C—H | CH₂ | C—H | C—H | H |
| 122 | C—H | C—H | C—H | C—H | O | C—H | C—H | H |
| 123 | C—H | C—H | C—H | C—H | CH₂ | C—H | C—H | H |
| 124 | C—Cl | C—H | C—H | C—Cl | O | C—H | C—H | H |
| 125 | C—Cl | C—H | C—H | C—Cl | CH₂ | C—H | C—H | H |
| 126 | C—H | C-iPr | C—H | C—H | O | C—H | C—H | H |
| 127 | C—H | C-iPr | C—H | C—H | CH₂ | C—H | C—H | H |
| 128 | C—H | C-isoxazol-3-yl | C—H | C—H | O | C—H | C—H | H |
| 129 | C—H | C-isoxazol-3-yl | C—H | C—H | CH₂ | C—H | C—H | H |
| 130 | C—H | C-isoxazol-5-yl | C—H | C—H | O | C—H | C—H | H |
| 131 | C—H | C-isoxazol-5-yl | C—H | C—H | CH₂ | C—H | C—H | H |
| 132 | C—H | C—Me | C—Me | C—H | O | C—H | C—H | H |
| 133 | C—H | C—Me | C—Me | C—H | CH₂ | C—H | C—H | H |
| 134 | C—H | C—Me | C—H | C—H | O | C—H | C—H | H |
| 135 | C—H | C—Me | C—H | C—H | CH₂ | C—H | C—H | H |
| 136 | C—H | C—OCF₃ | C—H | C—H | O | C—H | C—H | H |
| 137 | C—H | C—OCF₃ | C—H | C—H | CH₂ | C—H | C—H | H |
| 138 | C—H | C—OCF₃ | C—H | N | O | C—H | C—H | H |
| 139 | C—H | C—OCF₃ | C—H | N | CH₂ | C—H | C—H | H |
| 140 | N | C—OCF₃ | C—H | N | O | C—H | C—H | H |
| 141 | N | C—OCF₃ | C—H | N | CH₂ | C—H | C—H | H |
| 142 | C—H | C—OCF₃ | N | C—H | O | C—H | C—H | H |
| 142 | C—H | C—OCF₃ | N | C—H | CH₂ | C—H | C—H | H |
| 144 | C—H | C—OCHF₂ | C—H | C—H | O | C—H | C—H | H |
| 145 | C—H | C—OCHF₂ | C—H | C—H | CH₂ | C—H | C—H | H |
| 146 | C—H | C—OEt | C—H | C—H | O | C—H | C—H | H |
| 147 | C—H | C—OEt | C—H | C—H | CH₂ | C—H | C—H | H |
| 148 | C—H | C—OEt | C—F | C—H | O | C—H | C—H | H |
| 149 | C—H | C—OEt | C—F | C—H | CH₂ | C—H | C—H | H |
| 150 | C—H | C—OEt | C—H | N | O | C—H | C—H | H |
| 151 | C—H | C—OEt | C—H | N | CH₂ | C—H | C—H | H |
| 152 | N | C—OEt | C—H | N | O | C—H | C—H | H |
| 153 | N | C—OEt | C—H | N | CH₂ | C—H | C—H | H |
| 154 | C—H | C—OEt | N | C—H | O | C—H | C—H | H |
| 155 | C—H | C—OEt | N | C—H | CH₂ | C—H | C—H | H |
| 156 | C—H | C—OMe | C—H | C—H | O | C—H | C—H | H |
| 157 | C—H | C—OMe | C—H | C—H | CH₂ | C—H | C—H | H |
| 158 | C—H | C—OMe | C—OMe | C—H | O | C—H | C—H | H |
| 159 | C—H | C—OMe | C—OMe | C—H | CH₂ | C—H | C—H | H |
| 160 | C—H | C-oxazol-2-yl | C—H | C—H | O | C—H | C—H | H |
| 161 | C—H | C-oxazol-2-yl | C—H | C—H | CH₂ | C—H | C—H | H |
| 162 | C—H | C-oxazol-2-yl | C—H | N | O | C—H | C—H | H |
| 163 | C—H | C-oxazol-2-yl | C—H | N | CH₂ | C—H | C—H | H |
| 164 | N | C-oxazol-2-yl | C—H | N | O | C—H | C—H | H |
| 165 | N | C-oxazol-2-yl | C—H | N | CH₂ | C—H | C—H | H |
| 166 | C—H | C-oxazol-2-yl | N | C—H | O | C—H | C—H | H |

TABLE 1-continued

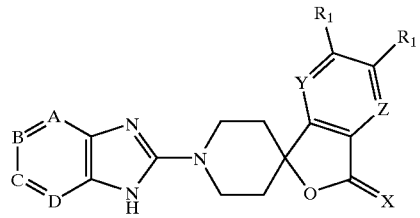

| EX | A | B | C | D | X | Y | Z | R$_1$ |
|---|---|---|---|---|---|---|---|---|
| 167 | C—H | C-oxazol-2-yl | N | C—H | CH$_2$ | C—H | C—H | H |
| 168 | N | C-oxazol-2-yl | N | C—H | O | C—H | C—H | H |
| 169 | N | C-oxazol-2-yl | N | C—H | CH$_2$ | C—H | C—H | H |
| 170 | C—H | C-oxazol-4-yl | C—H | C—H | O | C—H | C—H | H |
| 171 | C—H | C-oxazol-4-yl | C—H | C—H | CH$_2$ | C—H | C—H | H |
| 172 | C—H | C-oxazol-5-yl | C—H | C—H | O | C—H | C—H | H |
| 173 | C—H | C-oxazol-5-yl | C—H | C—H | CH$_2$ | C—H | C—H | H |
| 174 | C—H | C—Ph | C—H | C—H | O | C—H | C—H | H |
| 175 | C—H | C—Ph | C—H | C—H | CH$_2$ | C—H | C—H | H |
| 176 | C—H | C—Ph | C—H | N | O | C—H | C—H | H |
| 177 | C—H | C—Ph | C—H | N | CH$_2$ | C—H | C—H | H |
| 178 | C—H | C—Ph | N | C—H | O | C—H | C—H | H |
| 179 | C—H | C—Ph | N | C—H | CH$_2$ | C—H | C—H | H |
| 180 | N | C—Ph | C—H | N | O | C—H | C—H | H |
| 181 | N | C—Ph | C—H | N | CH$_2$ | C—H | C—H | H |
| 182 | N | C—Ph | N | C—H | O | C—H | C—H | H |
| 183 | N | C—Ph | N | C—H | CH$_2$ | C—H | C—H | H |
| 184 | C—H | C-(2-F—Ph) | C—H | C—H | O | C—H | C—H | H |
| 185 | C—H | C-(2-F—Ph) | C—H | C—H | CH$_2$ | C—H | C—H | H |
| 186 | C—H | C-(4-F—Ph) | C—H | C—H | O | C—H | C—H | H |
| 187 | C—H | C-(4-F—Ph) | C—H | C—H | CH$_2$ | C—H | C—H | H |
| 188 | C—H | C-(3-CN—Ph) | C—H | C—H | O | C—H | C—H | H |
| 189 | C—H | C-(3-CN—Ph) | C—H | C—H | CH$_2$ | C—H | C—H | H |
| 190 | C—H | C-(2-MeO—Ph) | C—H | C—H | O | C—H | C—H | H |
| 191 | C—H | C-(2-MeO—Ph) | C—H | C—H | CH$_2$ | C—H | C—H | H |
| 192 | C—H | C-(4-MeO—Ph) | C—H | C—H | O | C—H | C—H | H |
| 193 | C—H | C-(4-MeO—Ph) | C—H | C—H | CH$_2$ | C—H | C—H | H |
| 194 | C—H | C-pyrazin-2-yl | C—H | C—H | O | C—H | C—H | H |
| 195 | C—H | C-pyrazin-2-yl | C—H | C—H | CH$_2$ | C—H | C—H | H |
| 196 | C—H | C-pyridin-2-yl | C—H | C—H | O | C—H | C—H | H |
| 197 | C—H | C-pyridin-2-yl | C—H | C—H | CH$_2$ | C—H | C—H | H |
| 198 | C—H | C-pyridin-3-yl | C—H | C—H | O | C—H | C—H | H |
| 199 | C—H | C-pyridin-3-yl | C—H | C—H | CH$_2$ | C—H | C—H | H |
| 200 | C—H | C-pyridin-3-yl | C—H | N | O | C—H | C—H | H |
| 201 | C—H | C-pyridin-3-yl | C—H | N | CH$_2$ | C—H | C—H | H |
| 202 | N | C-pyridin-3-yl | C—H | N | O | C—H | C—H | H |
| 203 | C—H | C-pyridin-3-yl | N | C—H | O | C—H | C—H | H |
| 204 | C—H | C-pyridin-3-yl | N | C—H | CH$_2$ | C—H | C—H | H |
| 205 | N | C-pyridin-3-yl | C—H | N | CH$_2$ | C—H | C—H | H |
| 206 | C—H | C-pyridin-4-yl | C—H | C—H | O | C—H | C—H | H |
| 207 | C—H | C-pyridin-4-yl | C—H | C—H | CH$_2$ | C—H | C—H | H |
| 208 | C—H | C-pyrimidin-2-yl | C—H | C—H | O | C—H | C—H | H |
| 209 | C—H | C-pyrimidin-2-yl | C—H | C—H | CH$_2$ | C—H | C—H | H |
| 210 | C—H | C-pyrimidin-4-yl | C—H | C—H | O | C—H | C—H | H |
| 211 | C—H | C-pyrimidin-4-yl | C—H | C—H | CH$_2$ | C—H | C—H | H |
| 212 | C—H | C-pyrimidin-5-yl | C—H | C—H | O | C—H | C—H | H |
| 213 | C—H | C—pyrimidin-5-yl | C—H | C—H | CH$_2$ | C—H | C—H | H |
| 214 | C—H | C—SO$_2$CF$_3$ | C—H | C—H | O | C—H | C—H | H |
| 215 | C—H | C—SO$_2$CF$_3$ | C—H | C—H | CH$_2$ | C—H | C—H | H |
| 216 | C—H | C—SO$_2$Et | C—H | C—H | O | C—H | C—H | H |
| 217 | C—H | C—SO$_2$Et | C—H | C—H | CH$_2$ | C—H | C—H | H |
| 218 | C—H | C—SO$_2$iPr | C—H | C—H | O | C—H | C—H | H |
| 219 | C—H | C—SO$_2$iPr | C—H | C—H | CH$_2$ | C—H | C—H | H |
| 220 | C—H | C—SO$_2$Me | C—H | C—H | O | C—H | C—H | H |
| 221 | C—H | C—SO$_2$Me | C—H | C—H | CH$_2$ | C—H | C—H | H |
| 222 | C—H | C—SO$_2$Pr | C—H | C—H | O | C—H | C—H | H |
| 223 | C—H | C—SO$_2$Pr | C—H | C—H | CH$_2$ | C—H | C—H | H |
| 224 | C—H | C—SO$_2$Pr | C—H | N | O | C—H | C—H | H |
| 225 | C—H | C—SO$_2$Pr | C—H | N | CH$_2$ | C—H | C—H | H |
| 226 | C—H | C-tBu | C—H | C—H | O | C—H | C—H | H |
| 227 | C—H | C-tBu | C—H | C—H | CH$_2$ | C—H | C—H | H |
| 228 | C—H | C-thiazol-2-yl | C—H | C—H | O | C—H | C—H | H |
| 229 | C—H | C-thiazol-2-yl | C—H | C—H | CH$_2$ | C—H | C—H | H |
| 230 | C—H | C-thiazol-5-yl | C—H | C—H | O | C—H | C—H | H |
| 231 | C—H | C-thiazol-5-yl | C—H | C—H | CH$_2$ | C—H | C—H | H |

TABLE 1-continued

| EX | A | B | C | D | X | Y | Z | R₁ |
|---|---|---|---|---|---|---|---|---|
| 232 | C—H | C-thiophen-2-yl | C—H | C—H | O | C—H | C—H | H |
| 233 | C—H | C-thiophen-2-yl | C—H | C—H | CH₂ | C—H | C—H | H |
| 234 | C—H | C-thiophen-3-yl | C—H | C—H | O | C—H | C—H | H |
| 235 | C—H | C-thiophen-3-yl | C—H | C—H | CH₂ | C—H | C—H | H |
| 236 | C—H | C-triazol-2-yl | C—H | C—H | O | C—H | C—H | H |
| 237 | C—H | C-triazol-2-yl | C—H | C—H | CH₂ | C—H | C—H | H |
| 238 | C—H | C-(3,5-dimethyl-isoxazol-4-yl) | C—H | C—H | O | C—H | C—H | H |

TABLE 2

| Ex | A | B | C | D | X | Y | Z | R₁ |
|---|---|---|---|---|---|---|---|---|
| 239 | C—H | C-[1,2,4]oxadiazol-3-yl | C—H | C—H | O | C—H | C—H | H |
| 240 | C—H | C-[1,2,4]oxadiazol-3-yl | C—H | C—H | CH₂ | C—H | C—H | H |
| 241 | C—H | C-[1,2,4]oxadiazol-5-yl | C—H | C—H | O | C—H | C—H | H |
| 242 | C—H | C-[1,2,4]oxadiazol-5-yl | C—H | C—H | CH₂ | C—H | C—H | H |
| 243 | C—H | C-[1,3,4]oxadiazol-2-yl | C—H | C—H | O | C—H | C—H | H |
| 244 | C—H | C-[1,3,4]oxadiazol-2-yl | C—H | C—H | CH₂ | C—H | C—H | H |
| 245 | C—H | C-2-Me-oxazol-4-yl | C—H | C—H | O | C—H | C—H | H |
| 246 | C—H | C-2-Me-oxazol-4-yl | C—H | C—H | CH₂ | C—H | C—H | H |
| 247 | C—H | C-2-Me-oxazol-5-yl | C—H | C—H | O | C—H | C—H | H |
| 248 | C—H | C-2-Me-oxazol-5-yl | C—H | C—H | CH₂ | C—H | C—H | H |
| 249 | C—H | C-2-Me-pyrimidin-4-yl | C—H | C—H | O | C—H | C—H | H |
| 250 | C—H | C-2-Me-pyrimidin-4-yl | C—H | C—H | CH₂ | C—H | C—H | H |
| 251 | C—H | C-2-Me-pyrimidin-5-yl | C—H | C—H | O | C—H | C—H | H |
| 252 | C—H | C-2-Me-pyrimidin-5-yl | C—H | C—H | CH₂ | C—H | C—H | H |
| 253 | C—H | C-2-Me-thiazol-5-yl | C—H | C—H | O | C—H | C—H | H |
| 254 | C—H | C-2-Me-thiazol-5-yl | C—H | C—H | CH₂ | C—H | C—H | H |
| 255 | C—H | C-3-Me-[1,2,4]oxadiazol-5-yl | C—H | C—H | O | C—H | C—H | H |
| 256 | C—H | C-3-Me-[1,2,4]oxadiazol-5-yl | C—H | C—H | CH₂ | C—H | C—H | H |
| 257 | C—H | C-3-Me-isoxazol-5-yl | C—H | C—H | O | C—H | C—H | H |
| 258 | C—H | C-3-Me-isoxazol-5-yl | C—H | C—H | CH₂ | C—H | C—H | H |
| 259 | C—H | C-4-Me-oxazol-2-yl | C—H | C—H | O | C—H | C—H | H |
| 260 | C—H | C-4-Me-oxazol-2-yl | C—H | C—H | CH₂ | C—H | C—H | H |
| 261 | C—H | C-4-Me-thiazol-2-yl | C—H | C—H | O | C—H | C—H | H |
| 262 | C—H | C-4-Me-thiazol-2-yl | C—H | C—H | CH₂ | C—H | C—H | H |
| 263 | C—H | C-5-Me-[1,2,4]oxadiazol-3-yl | C—H | C—H | O | C—H | C—H | H |
| 264 | C—H | C-5-Me-[1,2,4]oxadiazol-3-yl | C—H | C—H | CH₂ | C—H | C—H | H |
| 265 | C—H | C-5-Me-[1,3,4]oxadiazol-2-yl | C—H | C—H | O | C—H | C—H | H |
| 266 | C—H | C-5-Me-[1,3,4]oxadiazol-2-yl | C—H | C—H | CH₂ | C—H | C—H | H |
| 267 | C—H | C-5-Me-isoxazol-3-yl | C—H | C—H | O | C—H | C—H | H |
| 268 | C—H | C-5-Me-isoxazol-3-yl | C—H | C—H | CH₂ | C—H | C—H | H |
| 269 | C—H | C-5-Me-pyrazin-2-yl | C—H | C—H | O | C—H | C—H | H |
| 270 | C—H | C-5-Me-pyrazin-2-yl | C—H | C—H | CH₂ | C—H | C—H | H |
| 271 | C—H | C-6-Me-pyrazin-2-yl | C—H | C—H | O | C—H | C—H | H |
| 272 | C—H | C-6-Me-pyrazin-2-yl | C—H | C—H | CH₂ | C—H | C—H | H |
| 273 | C—H | C—Br | C—H | C—H | O | C—H | C—H | H |
| 274 | C—H | C—Br | C—H | C—H | CH₂ | C—H | C—H | H |
| 275 | C—Cl | C—Br | C—H | C—H | O | C—H | C—H | H |
| 276 | C—Cl | C—Br | C—H | C—H | CH₂ | C—H | C—H | H |
| 277 | C—H | C—C=O—Et | C—H | C—H | O | C—H | C—H | H |

TABLE 2-continued

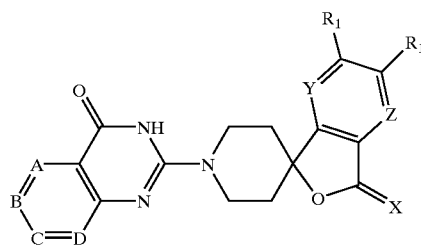

| Ex | A | B | C | D | X | Y | Z | R₁ |
|---|---|---|---|---|---|---|---|---|
| 278 | C—H | C—C=O—Et | C—H | C—H | CH₂ | C—H | C—H | H |
| 279 | C—H | C—C=O-iPr | C—H | C—H | O | C—H | C—H | H |
| 280 | C—H | C—C=O-iPr | C—H | C—H | CH₂ | C—H | C—H | H |
| 281 | C—H | C—C=O—Me | C—H | C—H | O | C—H | C—H | H |
| 282 | C—H | C—C=O—Me | C—H | C—H | CH₂ | C—H | C—H | H |
| 283 | C—H | C—C=O-nPr | C—H | C—H | O | C—H | C—H | H |
| 284 | C—H | C—C=O-nPr | C—H | C—H | CH₂ | C—H | C—H | H |
| 285 | C—H | C—C=O—Ph | C—H | C—H | O | C—H | C—H | H |
| 286 | C—H | C—C=O—Ph | C—H | C—H | CH₂ | C—H | C—H | H |
| 287 | C—H | C—C=O-tBu | C—H | C—H | O | C—H | C—H | H |
| 288 | C—H | C—C=O-tBu | C—H | C—H | CH₂ | C—H | C—H | H |
| 289 | C—H | C—CF₃ | C—H | C—H | O | C—H | C—H | H |
| 290 | C—H | C—CF₃ | C—H | C—H | CH₂ | C—H | C—H | H |
| 291 | C—H | C—CF₃ | C—F | C—H | O | C—H | C—H | H |
| 292 | C—H | C—CF₃ | C—F | C—H | CH₂ | C—H | C—H | H |
| 293 | C—H | C—CF₃ | C—H | N | O | C—H | C—H | H |
| 294 | C—H | C—CF₃ | C—H | N | CH₂ | C—H | C—H | H |
| 295 | N | C—CF₃ | C—H | N | O | C—H | C—H | H |
| 296 | N | C—CF₃ | C—H | N | CH₂ | C—H | C—H | H |
| 297 | C—H | C—CF₃ | N | C—H | O | C—H | C—H | H |
| 298 | C—H | C—CF₃ | N | C—H | CH₂ | C—H | C—H | H |
| 299 | N | C—CF₃ | N | C—H | O | C—H | C—H | H |
| 300 | N | C—CF₃ | N | C—H | CH₂ | C—H | C—H | H |
| 301 | C—H | C-cHex | C—H | C—H | O | C—H | C—H | H |
| 302 | C—H | C-cHex | C—H | C—H | CH₂ | C—H | C—H | H |
| 303 | C—H | C—Cl | C—H | C—H | O | C—H | C—H | H |
| 304 | C—H | C—Cl | C—H | C—H | CH₂ | C—H | C—H | H |
| 305 | C—H | C—Cl | C—H | C—Cl | O | C—H | C—H | H |
| 306 | C—H | C—Cl | C—H | C—Cl | CH₂ | C—H | C—H | H |
| 307 | C—H | C—Cl | C—H | N | O | C—H | C—H | H |
| 308 | C—H | C—Cl | C—H | N | CH₂ | C—H | C—H | H |
| 309 | N | C—Cl | C—H | N | O | C—H | C—H | H |
| 310 | N | C—Cl | C—H | N | CH₂ | C—H | C—H | H |
| 311 | C—H | C—CN | C—H | C—H | O | C—H | C—H | H |
| 312 | C—H | C—CN | C—H | C—H | CH₂ | C—H | C—H | H |
| 313 | C—H | C—CN | C—H | N | O | C—H | C—H | H |
| 314 | C—H | C—CN | C—H | N | CH₂ | C—H | C—H | H |
| 315 | N | C—CN | C—H | N | O | C—H | C—H | H |
| 316 | N | C—CN | C—H | N | CH₂ | C—H | C—H | H |
| 317 | C—H | C—CO₂Me | C—H | C—H | O | C—H | C—H | H |
| 318 | C—H | C—CO₂Me | C—H | C—H | CH₂ | C—H | C—H | H |
| 319 | C—H | C—CONEt₂ | C—H | C—H | O | C—H | C—H | H |
| 320 | C—H | C—CONEt₂ | C—H | C—H | CH₂ | C—H | C—H | H |
| 321 | C—H | C—CONHMe | C—H | C—H | O | C—H | C—H | H |
| 322 | C—H | C—CONHMe | C—H | C—H | CH₂ | C—H | C—H | H |
| 323 | C—H | C—CONMe₂ | C—H | C—H | O | C—H | C—H | H |
| 324 | C—H | C—CONMe₂ | C—H | C—H | CH₂ | C—H | C—H | H |
| 325 | C—H | C-cPent | C—H | C—H | O | C—H | C—H | H |
| 326 | C—H | C-cPent | C—H | C—H | CH₂ | C—H | C—H | H |
| 327 | C—H | C—Et | C—H | C—H | O | C—H | C—H | H |
| 328 | C—H | C—Et | C—H | C—H | CH₂ | C—H | C—H | H |
| 329 | C—H | C—F | C—H | C—H | O | C—H | C—H | H |
| 330 | C—H | C—F | C—H | C—H | CH₂ | C—H | C—H | H |
| 331 | C—H | C—F | C—F | C—H | O | C—H | C—H | H |
| 332 | C—H | C—F | C—F | C—H | CH₂ | C—H | C—H | H |
| 333 | C—H | C—F | C—H | N | O | C—H | C—H | H |
| 334 | C—H | C—F | C—H | N | CH₂ | C—H | C—H | H |
| 335 | C—CF₃ | C—H | C—H | C—H | O | C—H | C—H | H |
| 336 | C—CF₃ | C—H | C—H | C—H | CH₂ | C—H | C—H | H |
| 337 | C—Cl | C—H | C—H | C—H | O | C—H | C—H | H |
| 338 | C—Cl | C—H | C—H | C—H | CH₂ | C—H | C—H | H |
| 339 | C—H | C—H | C—H | C—H | O | C—H | C—H | H |
| 340 | C—H | C—H | C—H | C—H | CH₂ | C—H | C—H | H |
| 341 | C—Cl | C—H | C—H | C—Cl | O | C—H | C—H | H |

TABLE 2-continued

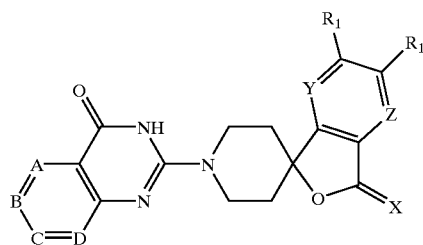

| Ex | A | B | C | D | X | Y | Z | R$_1$ |
|---|---|---|---|---|---|---|---|---|
| 342 | C—Cl | C—H | C—H | C—Cl | CH$_2$ | C—H | C—H | H |
| 343 | C—H | C-iPr | C—H | C—H | O | C—H | C—H | H |
| 344 | C—H | C-iPr | C—H | C—H | CH$_2$ | C—H | C—H | H |
| 345 | C—H | C-isoxazol-3-yl | C—H | C—H | O | C—H | C—H | H |
| 346 | C—H | C-isoxazol-3-yl | C—H | C—H | CH$_2$ | C—H | C—H | H |
| 347 | C—H | C-isoxazol-5-yl | C—H | C—H | O | C—H | C—H | H |
| 348 | C—H | C-isoxazol-5-yl | C—H | C—H | CH$_2$ | C—H | C—H | H |
| 349 | C—H | C—Me | C—Me | C—H | O | C—H | C—H | H |
| 350 | C—H | C—Me | C—Me | C—H | CH$_2$ | C—H | C—H | H |
| 351 | C—H | C—Me | C—H | C—H | O | C—H | C—H | H |
| 352 | C—H | C—Me | C—H | C—H | CH$_2$ | C—H | C—H | H |
| 353 | C—H | C—OCF$_3$ | C—H | C—H | O | C—H | C—H | H |
| 354 | C—H | C—OCF$_3$ | C—H | C—H | CH$_2$ | C—H | C—H | H |
| 355 | C—H | C—OCF$_3$ | C—H | N | O | C—H | C—H | H |
| 356 | C—H | C—OCF$_3$ | C—H | N | CH$_2$ | C—H | C—H | H |
| 357 | N | C—OCF$_3$ | C—H | N | O | C—H | C—H | H |
| 358 | N | C—OCF$_3$ | C—H | N | CH$_2$ | C—H | C—H | H |
| 359 | C—H | C—OCF$_3$ | N | C—H | O | C—H | C—H | H |
| 360 | C—H | C—OCF$_3$ | N | C—H | CH$_2$ | C—H | C—H | H |
| 361 | C—H | C—OCHF$_2$ | C—H | C—H | O | C—H | C—H | H |
| 362 | C—H | C—OCHF$_2$ | C—H | C—H | CH$_2$ | C—H | C—H | H |
| 363 | C—H | C—OEt | C—H | C—H | O | C—H | C—H | H |
| 364 | C—H | C—OEt | C—H | C—H | CH$_2$ | C—H | C—H | H |
| 365 | C—H | C—OEt | C—F | C—H | O | C—H | C—H | H |
| 366 | C—H | C—OEt | C—F | C—H | CH$_2$ | C—H | C—H | H |
| 367 | C—H | C—OEt | C—H | N | O | C—H | C—H | H |
| 368 | C—H | C—OEt | C—H | N | CH$_2$ | C—H | C—H | H |
| 369 | N | C—OEt | C—H | N | O | C—H | C—H | H |
| 370 | N | C—OEt | C—H | N | CH$_2$ | C—H | C—H | H |
| 371 | C—H | C—OEt | N | C—H | O | C—H | C—H | H |
| 372 | C—H | C—OEt | N | C—H | CH$_2$ | C—H | C—H | H |
| 373 | C—H | C—OMe | C—H | C—H | O | C—H | C—H | H |
| 374 | C—H | C—OMe | C—H | C—H | CH$_2$ | C—H | C—H | H |
| 375 | C—H | C—OMe | C—OMe | C—H | O | C—H | C—H | H |
| 376 | C—H | C—OMe | C—OMe | C—H | CH$_2$ | C—H | C—H | H |
| 377 | C—H | C-oxazol-2-yl | C—H | C—H | O | C—H | C—H | H |
| 378 | C—H | C-oxazol-2-yl | C—H | C—H | CH$_2$ | C—H | C—H | H |
| 379 | C—H | C-oxazol-2-yl | C—H | N | O | C—H | C—H | H |
| 380 | C—H | C-oxazol-2-yl | C—H | N | CH$_2$ | C—H | C—H | H |
| 381 | N | C-oxazol-2-yl | C—H | N | O | C—H | C—H | H |
| 382 | N | C-oxazol-2-yl | C—H | N | CH$_2$ | C—H | C—H | H |
| 383 | C—H | C-oxazol-2-yl | N | C—H | O | C—H | C—H | H |
| 384 | C—H | C-oxazol-2-yl | N | C—H | CH$_2$ | C—H | C—H | H |
| 385 | N | C-oxazol-2-yl | N | C—H | O | C—H | C—H | H |
| 386 | N | C-oxazol-2-yl | N | C—H | CH$_2$ | C—H | C—H | H |
| 387 | C—H | C-oxazol-4-yl | C—H | C—H | O | C—H | C—H | H |
| 388 | C—H | C-oxazol-4-yl | C—H | C—H | CH$_2$ | C—H | C—H | H |
| 389 | C—H | C-oxazol-5-yl | C—H | C—H | O | C—H | C—H | H |
| 390 | C—H | C-oxazol-5-yl | C—H | C—H | CH$_2$ | C—H | C—H | H |
| 391 | C—H | C—Ph | C—H | C—H | O | C—H | C—H | H |
| 392 | C—H | C—Ph | C—H | C—H | CH$_2$ | C—H | C—H | H |
| 393 | C—H | C—Ph | C—H | N | O | C—H | C—H | H |
| 394 | C—H | C—Ph | C—H | N | CH$_2$ | C—H | C—H | H |
| 395 | C—H | C—Ph | N | C—H | O | C—H | C—H | H |
| 396 | C—H | C—Ph | N | C—H | CH$_2$ | C—H | C—H | H |
| 397 | N | C—Ph | C—H | N | O | C—H | C—H | H |
| 398 | N | C—Ph | C—H | N | CH$_2$ | C—H | C—H | H |
| 399 | N | C—Ph | N | C—H | O | C—H | C—H | H |
| 400 | N | C—Ph | N | C—H | CH$_2$ | C—H | C—H | H |
| 401 | C—H | C-(2-F—Ph) | C—H | C—H | O | C—H | C—H | H |
| 402 | C—H | C-(2-F—Ph) | C—H | C—H | CH$_2$ | C—H | C—H | H |
| 403 | C—H | C-(4-F—Ph) | C—H | C—H | O | C—H | C—H | H |
| 404 | C—H | C-(4-F—Ph) | C—H | C—H | CH$_2$ | C—H | C—H | H |
| 405 | C—H | C-(3-CN—Ph) | C—H | C—H | O | C—H | C—H | H |

TABLE 2-continued

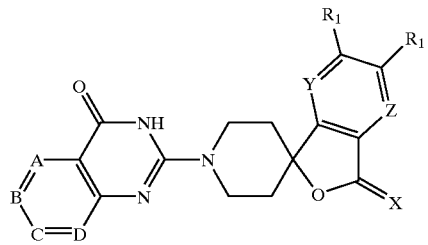

| Ex | A | B | C | D | X | Y | Z | R$_1$ |
|---|---|---|---|---|---|---|---|---|
| 406 | C—H | C-(3-CN—Ph) | C—H | C—H | CH$_2$ | C—H | C—H | H |
| 407 | C—H | C-(2-MeO—Ph) | C—H | C—H | O | C—H | C—H | H |
| 408 | C—H | C-(2-MeO—Ph) | C—H | C—H | CH$_2$ | C—H | C—H | H |
| 409 | C—H | C-(4-MeO—Ph) | C—H | C—H | O | C—H | C—H | H |
| 410 | C—H | C-(4-MeO—Ph) | C—H | C—H | CH$_2$ | C—H | C—H | H |
| 411 | C—H | C-pyrazin-2-yl | C—H | C—H | O | C—H | C—H | H |
| 412 | C—H | C-pyrazin-2-yl | C—H | C—H | CH$_2$ | C—H | C—H | H |
| 413 | C—H | C-pyridin-2-yl | C—H | C—H | O | C—H | C—H | H |
| 414 | C—H | C-pyridin-2-yl | C—H | C—H | CH$_2$ | C—H | C—H | H |
| 415 | C—H | C-pyridin-3-yl | C—H | C—H | O | C—H | C—H | H |
| 416 | C—H | C-pyridin-3-yl | C—H | C—H | CH$_2$ | C—H | C—H | H |
| 417 | C—H | C-pyridin-3-yl | C—H | N | O | C—H | C—H | H |
| 418 | C—H | C-pyridin-3-yl | C—H | N | CH$_2$ | C—H | C—H | H |
| 419 | N | C-pyridin-3-yl | C—H | N | O | C—H | C—H | H |
| 420 | C—H | C-pyridin-3-yl | N | C—H | O | C—H | C—H | H |
| 421 | C—H | C-pyridin-3-yl | N | C—H | CH$_2$ | C—H | C—H | H |
| 422 | N | C-pyridin-3-yl | C—H | N | CH$_2$ | C—H | C—H | H |
| 423 | C—H | C-pyridin-4-yl | C—H | C—H | O | C—H | C—H | H |
| 424 | C—H | C-pyridin-4-yl | C—H | C—H | CH$_2$ | C—H | C—H | H |
| 425 | C—H | C-pyrimidin-2-yl | C—H | C—H | O | C—H | C—H | H |
| 426 | C—H | C-pyrimidin-2-yl | C—H | C—H | CH$_2$ | C—H | C—H | H |
| 427 | C—H | C-pyrimidin-4-yl | C—H | C—H | O | C—H | C—H | H |
| 428 | C—H | C-pyrimidin-4-yl | C—H | C—H | CH$_2$ | C—H | C—H | H |
| 429 | C—H | C-pyrimidin-5-yl | C—H | C—H | O | C—H | C—H | H |
| 430 | C—H | C-pyrimidin-5-yl | C—H | C—H | CH$_2$ | C—H | C—H | H |
| 431 | C—H | C—SO$_2$CF$_3$ | C—H | C—H | O | C—H | C—H | H |
| 432 | C—H | C—SO$_2$CF$_3$ | C—H | C—H | CH$_2$ | C—H | C—H | H |
| 433 | C—H | C—SO$_2$Et | C—H | C—H | O | C—H | C—H | H |
| 434 | C—H | C—SO$_2$Et | C—H | C—H | CH$_2$ | C—H | C—H | H |
| 435 | C—H | C—SO$_2$iPr | C—H | C—H | O | C—H | C—H | H |
| 436 | C—H | C—SO$_2$iPr | C—H | C—H | CH$_2$ | C—H | C—H | H |
| 437 | C—H | C—SO$_2$Me | C—H | C—H | O | C—H | C—H | H |
| 438 | C—H | C—SO$_2$Me | C—H | C—H | CH$_2$ | C—H | C—H | H |
| 439 | C—H | C—SO$_2$Pr | C—H | C—H | O | C—H | C—H | H |
| 440 | C—H | C—SO$_2$Pr | C—H | C—H | CH$_2$ | C—H | C—H | H |
| 441 | C—H | C—SO$_2$Pr | C—H | N | O | C—H | C—H | H |
| 442 | C—H | C—SO$_2$Pr | C—H | N | CH$_2$ | C—H | C—H | H |
| 443 | C—H | C-tBu | C—H | C—H | O | C—H | C—H | H |
| 444 | C—H | C-tBu | C—H | C—H | CH$_2$ | C—H | C—H | H |
| 445 | C—H | C-thiazol-2-yl | C—H | C—H | O | C—H | C—H | H |
| 446 | C—H | C-thiazol-2-yl | C—H | C—H | CH$_2$ | C—H | C—H | H |
| 447 | C—H | C-thiazol-5-yl | C—H | C—H | O | C—H | C—H | H |
| 448 | C—H | C-thiazol-5-yl | C—H | C—H | CH$_2$ | C—H | C—H | H |
| 449 | C—H | C-thiophen-2-yl | C—H | C—H | O | C—H | C—H | H |
| 450 | C—H | C-thiophen-2-yl | C—H | C—H | CH$_2$ | C—H | C—H | H |
| 451 | C—H | C-thiophen-3-yl | C—H | C—H | O | C—H | C—H | H |
| 452 | C—H | C-thiophen-3-yl | C—H | C—H | CH$_2$ | C—H | C—H | H |
| 453 | C—H | C-triazol-2-yl | C—H | C—H | O | C—H | C—H | H |
| 454 | C—H | C-triazol-2-yl | C—H | C—H | CH$_2$ | C—H | C—H | H |

TABLE 3

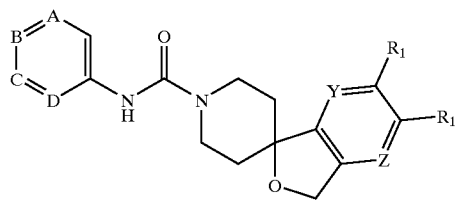

| Ex | A | B | C | D | Y | Z | R₁ |
|---|---|---|---|---|---|---|---|
| 455 | C—H | C-[1,2,4]oxadiazol-3-yl | C—H | C—H | C—H | C—H | H |
| 456 | C—H | C-[1,2,4]oxadiazol-5-yl | C—H | C—H | C—H | C—H | H |
| 457 | C—H | C-[1,3,4]oxadiazol-2-yl | C—H | C—H | C—H | C—H | H |
| 458 | C—H | C-2-Me-oxazol-4-yl | C—H | C—H | C—H | C—H | H |
| 459 | C—H | C-2-Me-oxazol-5-yl | C—H | C—H | C—H | C—H | H |
| 460 | C—H | C-2-Me-pyrimidin-4-yl | C—H | C—H | C—H | C—H | H |
| 461 | C—H | C-2-Me-pyrimidin-5-yl | C—H | C—H | C—H | C—H | H |
| 462 | C—H | C-2-Me-thiazol-5-yl | C—H | C—H | C—H | C—H | H |
| 463 | C—H | C-3-Me-[1,2,4]oxadiazol-5-yl | C—H | C—H | C—H | C—H | H |
| 464 | C—H | C-3-Me-isoxazol-5-yl | C—H | C—H | C—H | C—H | H |
| 465 | C—H | C-4-Me-oxazol-2-yl | C—H | C—H | C—H | C—H | H |
| 466 | C—H | C-4-Me-thiazol-2-yl | C—H | C—H | C—H | C—H | H |
| 467 | C—H | C-5-Me-[1,2,4]oxadiazol-3-yl | C—H | C—H | C—H | C—H | H |
| 468 | C—H | C-5-Me-[1,3,4]oxadiazol-2-yl | C—H | C—H | C—H | C—H | H |
| 469 | C—H | C-5-Me-isoxazol-3-yl | C—H | C—H | C—H | C—H | H |
| 470 | C—H | C-5-Me-pyrazin-2-yl | C—H | C—H | C—H | C—H | H |
| 471 | C—H | C-6-Me-pyrazin-2-yl | C—H | C—H | C—H | C—H | H |
| 472 | C—H | C—Br | C—H | C—H | C—H | C—H | H |
| 473 | C—Cl | C—Br | C—H | C—H | C—H | C—H | H |
| 474 | C—H | C—C=O—Et | C—H | C—H | C—H | C—H | H |
| 475 | C—H | C—C=O-iPr | C—H | C—H | C—H | C—H | H |
| 476 | C—H | C—C=O—Me | C—H | C—H | C—H | C—H | H |
| 477 | C—H | C—C=O-nPr | C—H | C—H | C—H | C—H | H |
| 478 | C—H | C—C=O—Ph | C—H | C—H | C—H | C—H | H |
| 479 | C—H | C—C=O-tBu | C—H | C—H | C—H | C—H | H |
| 480 | C—H | C—CF₃ | C—H | C—H | C—H | C—H | H |
| 481 | C—H | C—CF₃ | C—F | C—H | C—H | C—H | H |
| 482 | C—H | C—CF₃ | C—H | N | C—H | C—H | H |
| 483 | N | C—CF₃ | C—H | N | C—H | C—H | H |
| 484 | C—H | C—CF₃ | N | C—H | C—H | C—H | H |
| 485 | N | C—CF₃ | N | C—H | C—H | C—H | H |
| 486 | C—H | C-cHex | C—H | C—H | C—H | C—H | H |
| 487 | C—H | C—Cl | C—H | C—H | C—H | C—H | H |
| 488 | C—H | C—Cl | C—H | C—H | C—Cl | C—H | H |
| 489 | C—H | C—Cl | C—H | N | C—H | C—H | H |
| 490 | N | C—Cl | C—H | N | C—H | C—H | H |
| 491 | C—H | C—CN | C—H | C—H | C—H | C—H | H |
| 492 | C—H | C—CN | C—H | N | C—H | C—H | H |
| 493 | N | C—CN | C—H | N | C—H | C—H | H |
| 494 | C—H | C—CO₂Me | C—H | C—H | C—H | C—H | H |
| 495 | C—H | C—CONEt₂ | C—H | C—H | C—H | C—H | H |
| 496 | C—H | C—CONHMe | C—H | C—H | C—H | C—H | H |
| 497 | C—H | C—CONMe₂ | C—H | C—H | C—H | C—H | H |
| 498 | C—H | C-cPent | C—H | C—H | C—H | C—H | H |
| 499 | C—H | C—Et | C—H | C—H | C—H | C—H | H |
| 500 | C—H | C—F | C—H | C—H | C—H | C—H | H |
| 501 | C—H | C—F | C—F | C—H | C—H | C—H | H |
| 502 | C—H | C—F | C—H | N | C—H | C—H | H |
| 503 | C—CF₃ | C—H | C—H | C—H | C—H | C—H | H |
| 504 | C—Cl | C—H | C—H | C—H | C—H | C—H | H |
| 505 | C—Cl | C—H | C—H | C—H | C—H | C—H | H |
| 506 | C—Cl | C—H | C—H | C—Cl | C—H | C—H | H |
| 507 | C—H | C-iPr | C—H | C—H | C—H | C—H | H |
| 508 | C—H | C-isoxazol-3-yl | C—H | C—H | C—H | C—H | H |
| 509 | C—H | C-isoxazol-5-yl | C—H | C—H | C—H | C—H | H |
| 510 | C—H | C—Me | C—Me | C—H | C—H | C—H | H |
| 511 | C—H | C—Me | C—H | C—H | C—H | C—H | H |
| 512 | C—H | C—OCF₃ | C—H | C—H | C—H | C—H | H |
| 513 | C—H | C—OCF₃ | C—H | N | C—H | C—H | H |
| 514 | N | C—OCF₃ | C—H | N | C—H | C—H | H |
| 515 | C—H | C—OCF₃ | N | C—H | C—H | C—H | H |
| 516 | C—H | C—OCHF₂ | C—H | C—H | C—H | C—H | H |
| 517 | C—H | C—OEt | C—H | C—H | C—H | C—H | H |
| 518 | C—H | C—OEt | C—F | C—H | C—H | C—H | H |
| 519 | C—H | C—OEt | C—H | N | C—H | C—H | H |
| 520 | N | C—OEt | C—H | N | C—H | C—H | H |

TABLE 3-continued

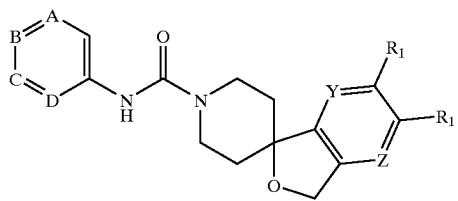

| Ex | A | B | C | D | Y | Z | $R_1$ |
|---|---|---|---|---|---|---|---|
| 521 | C—H | C—OEt | N | C—H | C—H | C—H | H |
| 522 | C—H | C—OMe | C—H | C—H | C—H | C—H | H |
| 523 | C—H | C—OMe | C—OMe | C—H | C—H | C—H | H |
| 524 | C—H | C-oxazol-2-yl | C—H | C—H | C—H | C—H | H |
| 525 | C—H | C-oxazol-2-yl | C—H | N | C—H | C—H | H |
| 526 | N | C-oxazol-2-yl | C—H | N | C—H | C—H | H |
| 527 | C—H | C-oxazol-2-yl | N | C—H | C—H | C—H | H |
| 528 | N | C-oxazol-2-yl | N | C—H | C—H | C—H | H |
| 529 | C—H | C-oxazol-4-yl | C—H | C—H | C—H | C—H | H |
| 530 | C—H | C-oxazol-5-yl | C—H | C—H | C—H | C—H | H |
| 531 | C—H | C—Ph | C—H | C—H | C—H | C—H | H |
| 532 | C—H | C—Ph | C—H | N | C—H | C—H | H |
| 533 | C—H | C—Ph | N | C—H | C—H | C—H | H |
| 534 | N | C—Ph | C—H | N | C—H | C—H | H |
| 535 | N | C—Ph | N | C—H | C—H | C—H | H |
| 536 | C—H | C-(2-F—Ph) | C—H | C—H | C—H | C—H | H |
| 537 | C—H | C-(4-F—Ph) | C—H | C—H | C—H | C—H | H |
| 538 | C—H | C-(3-CN—Ph) | C—H | C—H | C—H | C—H | H |
| 539 | C—H | C-(2-MeO—Ph) | C—H | C—H | C—H | C—H | H |
| 540 | C—H | C-(4-MeO—Ph) | C—H | C—H | C—H | C—H | H |
| 541 | C—H | C-pyrazin-2-yl | C—H | C—H | C—H | C—H | H |
| 542 | C—H | C-pyridin-2-yl | C—H | C—H | C—H | C—H | H |
| 543 | C—H | C-pyridin-3-yl | C—H | C—H | C—H | C—H | H |
| 544 | C—H | C-pyridin-3-yl | C—H | N | C—H | C—H | H |
| 545 | C—H | C-pyridin-3-yl | N | C—H | C—H | C—H | H |
| 546 | N | C-pyridin-3-yl | C—H | N | C—H | C—H | H |
| 547 | C—H | C-pyridin-4-yl | C—H | C—H | C—H | C—H | H |
| 548 | C—H | C-pyrimidin-2-yl | C—H | C—H | C—H | C—H | H |
| 549 | C—H | C-pyrimidin-4-yl | C—H | C—H | C—H | C—H | H |
| 550 | C—H | C-pyrimidin-5-yl | C—H | C—H | C—H | C—H | H |
| 551 | C—H | C—$SO_2CF_3$ | C—H | C—H | C—H | C—H | H |
| 552 | C—H | C—$SO_2Et$ | C—H | C—H | C—H | C—H | H |
| 553 | C—H | C—$SO_2iPr$ | C—H | C—H | C—H | C—H | H |
| 554 | C—H | C—$SO_2Me$ | C—H | C—H | C—H | C—H | H |
| 555 | C—H | C—$SO_2Pr$ | C—H | C—H | C—H | C—H | H |
| 556 | C—H | C—$SO_2Pr$ | C—H | N | C—H | C—H | H |
| 557 | C—H | C-tBu | C—H | C—H | C—H | C—H | H |
| 558 | C—H | C-thiazol-2-yl | C—H | C—H | C—H | C—H | H |
| 559 | C—H | C-thiazol-5-yl | C—H | C—H | C—H | C—H | H |
| 560 | C—H | C-thiophen-2-yl | C—H | C—H | C—H | C—H | H |
| 561 | C—H | C-thiophen-3-yl | C—H | C—H | C—H | C—H | H |
| 562 | C—H | C-triazol-2-yl | C—H | C—H | C—H | C—H | H |

TABLE 4

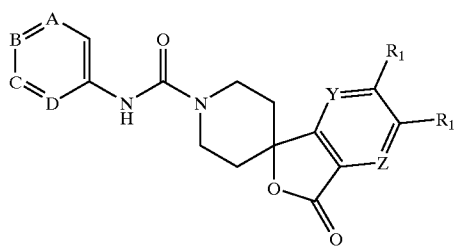

| Ex | A | B | C | D | Y | Z | $R_1$ |
|---|---|---|---|---|---|---|---|
| 563 | C—H | C-[1,2,4]oxadiazol-3-yl | C—H | C—H | C—H | C—H | H |
| 564 | C—H | C-[1,2,4]oxadiazol-5-yl | C—H | C—H | C—H | C—H | H |
| 565 | C—H | C-[1,3,4]oxadiazol-2-yl | C—H | C—H | C—H | C—H | H |
| 566 | C—H | C-2-Me-oxazol-4-yl | C—H | C—H | C—H | C—H | H |

TABLE 4-continued

| Ex | A | B | C | D | Y | Z | R₁ |
|---|---|---|---|---|---|---|---|
| 567 | C—H | C-2-Me-oxazol-5-yl | C—H | C—H | C—H | C—H | H |
| 568 | C—H | C-2-Me-pyrimidin-4-yl | C—H | C—H | C—H | C—H | H |
| 569 | C—H | C-2-Me-pyrimidin-5-yl | C—H | C—H | C—H | C—H | H |
| 570 | C—H | C-2-Me-thiazol-5-yl | C—H | C—H | C—H | C—H | H |
| 571 | C—H | C-3-Me-[1,2,4]oxadiazol-5-yl | C—H | C—H | C—H | C—H | H |
| 572 | C—H | C-3-Me-isoxazol-5-yl | C—H | C—H | C—H | C—H | H |
| 573 | C—H | C-4-Me-oxazol-2-yl | C—H | C—H | C—H | C—H | H |
| 574 | C—H | C-4-Me-thiazol-2-yl | C—H | C—H | C—H | C—H | H |
| 575 | C—H | C-5-Me-[1,2,4]oxadiazol-3-yl | C—H | C—H | C—H | C—H | H |
| 576 | C—H | C-5-Me-[1,3,4]oxadiazol-2-yl | C—H | C—H | C—H | C—H | H |
| 577 | C—H | C-5-Me-isoxazol-3-yl | C—H | C—H | C—H | C—H | H |
| 578 | C—H | C-5-Me-pyrazin-2-yl | C—H | C—H | C—H | C—H | H |
| 579 | C—H | C-6-Me-pyrazin-2-yl | C—H | C—H | C—H | C—H | H |
| 580 | C—H | C—Br | C—H | C—H | C—H | C—H | H |
| 581 | C—Cl | C—Br | C—H | C—H | C—H | C—H | H |
| 582 | C—H | C—C=O—Et | C—H | C—H | C—H | C—H | H |
| 583 | C—H | C—C=O-iPr | C—H | C—H | C—H | C—H | H |
| 584 | C—H | C—C=O—Me | C—H | C—H | C—H | C—H | H |
| 585 | C—H | C—C=O—nPr | C—H | C—H | C—H | C—H | H |
| 586 | C—H | C—C=O—Ph | C—H | C—H | C—H | C—H | H |
| 587 | C—H | C—C=O-tBu | C—H | C—H | C—H | C—H | H |
| 588 | C—H | C—CF₃ | C—H | C—H | C—H | C—H | H |
| 589 | C—H | C—CF₃ | C—F | C—H | C—H | C—H | H |
| 590 | C—H | C—CF₃ | C—H | N | C—H | C—H | H |
| 591 | N | C—CF₃ | C—H | N | C—H | C—H | H |
| 592 | C—H | C—CF₃ | N | C—H | C—H | C—H | H |
| 593 | N | C—CF₃ | N | C—H | C—H | C—H | H |
| 594 | C—H | C-cHex | C—H | C—H | C—H | C—H | H |
| 595 | C—H | C—Cl | C—H | C—H | C—H | C—H | H |
| 596 | C—H | C—Cl | C—H | C—Cl | C—H | C—H | H |
| 597 | C—H | C—Cl | C—H | N | C—H | C—H | H |
| 598 | N | C—Cl | C—H | N | C—H | C—H | H |
| 599 | C—H | C—CN | C—H | C—H | C—H | C—H | H |
| 600 | C—H | C—CN | C—H | N | C—H | C—H | H |
| 601 | N | C—CN | C—H | N | C—H | C—H | H |
| 602 | C—H | C—CO₂Me | C—H | C—H | C—H | C—H | H |
| 603 | C—H | C—CONEt₂ | C—H | C—H | C—H | C—H | H |
| 604 | C—H | C—CONHMe | C—H | C—H | C—H | C—H | H |
| 605 | C—H | C—CONMe₂ | C—H | C—H | C—H | C—H | H |
| 606 | C—H | C-cPent | C—H | C—H | C—H | C—H | H |
| 604 | C—H | C—Et | C—H | C—H | C—H | C—H | H |
| 608 | C—H | C—F | C—H | C—H | C—H | C—H | H |
| 609 | C—H | C—F | C—F | C—H | C—H | C—H | H |
| 610 | C—H | C—F | C—H | N | C—H | C—H | H |
| 611 | C—CF₃ | C—H | C—H | C—H | C—H | C—H | H |
| 612 | C—Cl | C—H | C—H | C—H | C—H | C—H | H |
| 613 | C—H | C—H | C—H | C—H | C—H | C—H | H |
| 614 | C—Cl | C—H | C—H | C—Cl | C—H | C—H | H |
| 615 | C—H | C-iPr | C—H | C—H | C—H | C—H | H |
| 616 | C—H | C-isoxazol-3-yl | C—H | C—H | C—H | C—H | H |
| 617 | C—H | C-isoxazol-5-yl | C—H | C—H | C—H | C—H | H |
| 618 | C—H | C—Me | C—Me | C—H | C—H | C—H | H |
| 619 | C—H | C—Me | C—H | C—H | C—H | C—H | H |
| 620 | C—H | C—OCF₃ | C—H | C—H | C—H | C—H | H |
| 621 | C—H | C—OCF₃ | C—H | N | C—H | C—H | H |
| 622 | N | C—OCF₃ | C—H | N | C—H | C—H | H |
| 623 | C—H | C—OCF₃ | N | C—H | C—H | C—H | H |
| 624 | C—H | C—OCHF₂ | C—H | C—H | C—H | C—H | H |
| 625 | C—H | C—OEt | C—H | C—H | C—H | C—H | H |
| 626 | C—H | C—OEt | C—F | C—H | C—H | C—H | H |
| 627 | C—H | C—OEt | C—H | N | C—H | C—H | H |
| 628 | N | C—OEt | C—H | N | C—H | C—H | H |
| 629 | C—H | C—OEt | N | C—H | C—H | C—H | H |
| 630 | C—H | C—OMe | C—H | C—H | C—H | C—H | H |

TABLE 4-continued

| Ex | A | B | C | D | Y | Z | R₁ |
|---|---|---|---|---|---|---|---|
| 631 | C—H | C—OMe | C—OMe | C—H | C—H | C—H | H |
| 632 | C—H | C-oxazol-2-yl | C—H | C—H | C—H | C—H | H |
| 633 | C—H | C-oxazol-2-yl | C—H | N | C—H | C—H | H |
| 634 | N | C-oxazol-2-yl | C—H | N | C—H | C—H | H |
| 635 | C—H | C-oxazol-2-yl | N | C—H | C—H | C—H | H |
| 636 | N | C-oxazol-2-yl | N | C—H | C—H | C—H | H |
| 637 | C—H | C-oxazol-4-yl | C—H | C—H | C—H | C—H | H |
| 638 | C—H | C-oxazol-5-yl | C—H | C—H | C—H | C—H | H |
| 639 | C—H | C—Ph | C—H | C—H | C—H | C—H | H |
| 640 | C—H | C—Ph | C—H | N | C—H | C—H | H |
| 641 | C—H | C—Ph | N | C—H | C—H | C—H | H |
| 642 | N | C—Ph | C—H | N | C—H | C—H | H |
| 643 | N | C—Ph | N | C—H | C—H | C—H | H |
| 644 | C—H | C-(2-F—Ph) | C—H | C—H | C—H | C—H | H |
| 645 | C—H | C-(4-F—Ph) | C—H | C—H | C—H | C—H | H |
| 646 | C—H | C-(3-CN—Ph) | C—H | C—H | C—H | C—H | H |
| 647 | C—H | C-(2-MeO—Ph) | C—H | C—H | C—H | C—H | H |
| 648 | C—H | C-(4-MeO—Ph) | C—H | C—H | C—H | C—H | H |
| 649 | C—H | C-pyrazin-2-yl | C—H | C—H | C—H | C—H | H |
| 650 | C—H | C-pyridin-2-yl | C—H | C—H | C—H | C—H | H |
| 651 | C—H | C-pyridin-3-yl | C—H | C—H | C—H | C—H | H |
| 652 | C—H | C-pyridin-3-yl | C—H | N | C—H | C—H | H |
| 653 | N | C-pyridin-3-yl | C—H | N | C—H | C—H | H |
| 654 | C—H | C-pyridin-3-yl | N | C—H | C—H | C—H | H |
| 655 | C—H | C-pyridin-4-yl | C—H | C—H | C—H | C—H | H |
| 656 | C—H | C-pyrimidin-2-yl | C—H | C—H | C—H | C—H | H |
| 657 | C—H | C-pyrimidin-4-yl | C—H | C—H | C—H | C—H | H |
| 658 | C—H | C-pyrimidin-5-yl | C—H | C—H | C—H | C—H | H |
| 659 | C—H | C—SO₂CF₃ | C—H | C—H | C—H | C—H | H |
| 660 | C—H | C—SO₂Et | C—H | C—H | C—H | C—H | H |
| 661 | C—H | C—SO₂iPr | C—H | C—H | C—H | C—H | H |
| 662 | C—H | C—SO₂Me | C—H | C—H | C—H | C—H | H |
| 663 | C—H | C—SO₂Pr | C—H | C—H | C—H | C—H | H |
| 664 | C—H | C—SO₂Pr | C—H | N | C—H | C—H | H |
| 665 | C—H | C-tBu | C—H | C—H | C—H | C—H | H |
| 666 | C—H | C-thiazol-2-yl | C—H | C—H | C—H | C—H | H |
| 667 | C—H | C-thiazol-5-yl | C—H | C—H | C—H | C—H | H |
| 668 | C—H | C-thiophen-2-yl | C—H | C—H | C—H | C—H | H |
| 669 | C—H | C-thiophen-3-yl | C—H | C—H | C—H | C—H | H |
| 670 | C—H | C-triazol-2-yl | C—H | C—H | C—H | C—H | H |
| 671 | N | C-piperidin-1-yl | C—H | C—H | C—H | C—H | H |
| 672 | N | C—OCH₃ | C—H | C—H | C—H | C—H | H |
| 673 | C—H | C—CH₃ | C—H | N | C—H | C—H | H |
| 674 | N | C-pyrrolidin-1-yl | C—H | C—H | C—H | C—H | H |

Example 675

Preparation of NPY5 Chimeric Receptors

This Example illustrates the preparation of a representative NPY5 receptor for use in assays described herein.

A. DNA Clones Encoding NPY Receptors

Human Y5 receptor was cloned from genomic DNA using a 5'Primer TTTTGGTTGCTGACAAATGTC (SEQ ID NO:1) and a 3' Primer CCTTGGTAAACAGTGAGAAT-TATTAC (SEQ ID NO:2). The fall length PCR product was initially cloned into the vector pCR 2.1 (Invitrogen, Carlsbad, Calif.) and then subcloned into pBluescript SK Minus (PBSSKM, Stratagene, La Jolla Calif.). This was designated pNN32

Bases 197 to 1433 of Y1 receptor (Genbank Accession number M88461, SEQ ID NO:3) were subcloned into pBSSKM and designated pNN22. A pBSSKM clone encoding a 5' truncated form of the Y5 receptor was made which deleted the 5' end of the coding region to the Nco I site. This was designated pNN39.

B. Chimeric Receptors hNPY5ΔY1IC3 (SEQ ID NO:5)

For the IC loop 3 chimera, pNN39 was digested with PstI (located at about residues 748–753 of human Y5 receptor sequence (SEQ ID NO:6) and Bgl II (located at about residues 1130–1135 of the human Y5 receptor sequence) removing bases 753 to 1130.

The portion of IC loop 3 from bases 903–964 (TACGCCTAAAAAGGAGAAACAACATGATGGACA-AGATGAGAGACAATAAGTACAGGTCCAGT; SEQ ID NO: 8) of human Y5 receptor, corresponding to amino acids 236–256 (IRLKRRNNMMDKMRDNKYRSS;

SEQ ID NO:9) of the human Y5 receptor amino acid sequence, was inserted into Y5 using the HY1L3S sense oligo (SEQ ID NO:10) and the HY1L3AS antisense oligo (SEQ ID NO: 11). A reaction mixture containing the 2 oligos was heated to 100° C. and allowed to cool slowly to anneal the oligos. The double stranded annealing product was then ligated into the PstI-Bgl II digested pNN39 to yield plasmid pNN100. The pNN100 insert was then reintroduced into the full-length human Y5 gene (pNN32) at the Cel 2 site and the resulting plasmid was designated pNN42.

(2) hNPY5ΔY1CT (SEQ ID NO:12)

To add the Y1 C-terminus to Y5, an Eco RI site was added to each gene. For Y1, bases 1173 to 1178 (ACTTCC) of human Y1 receptor (SEQ ID NO:3) were mutated to create an Eco R1site via PCR from forward primer HY1R1 (SEQ ID NO: 13) to a T3 reverse primer (priming from the multiple cloning site—"MCS"—of pBSSKM). The Y1 3' tail was then isolated by digesting with Eco RI and Xba (which later enzyme cuts out the Y1 3' tail in the MCS of pBSSKM).

For Y5, bases 1338 to 1343 (GGATTA) of human Y5 receptor were mutated using the PCR reverse primer HY5R1 (SEQ ID NO: 14). This primer was paired with a forward primer corresponding to bases 527–551 (GCTACTGTCTGGACACTAGGTTTTG; SEQ ID NO:15) of human Y5 receptor, and PCR carried out with the human Y5 coding sequence as template. The resulting PCR band was cut Pst I to the introduced Eco RI site.

pNN39 was then opened Pst I to Xba from the MCS of pBSSKM and the mutated Y5 segment Pst1 to Eco RI was mixed with the mutated Y1 3' fragment Eco RI to Xba from the MCS to set up a three-way ligation. The resulting mutated gene fragment was then introduced into the full-length Y5 gene at the Bgl 2 site.

(3) hNPY5ΔY1IC3/ΔY1CT (SEQ ID NO: 16)

The IC loop 3 +CT tail exchange was obtained by combining the above 2 mutant genes in the following manner. Full length hY5 (pNN32) was digested with Cel 2 (located at about residues 619–625 of human Y5 receptor) and Xba in the vector MCS. The loop 3 mutation pNN42 fragment Cel II to Bgl II was combined with the CT mutation pNN43 fragment Bgl II to Xba from the MCS resulting in pNN44. pNN44 encodes a human chimeric NPY$_5$/NPY, NPY receptor, consisting of N-terminal amino acids 1–442 of the human NPY$_5$ receptor and C-terminal amino acids 328–384 of the human NPY, receptor. The amino acid sequence of this chimeric receptor, referred to herein as hNPY5ΔY1IC3/ΔY1CT is shown in SEQ ID NO: 017:).

PNN44 was then digested with Kpn I and Xba I and subcloned into the commercial expression vector pBacPAK9 (Clontech, Palo Alto, Calif.) for expression in SF9 cells.

C. Baculoviral Preparations

The Baculoviral expression vector was co-transfected along with BACULOGOLD DNA (BD PharMingen, San Diego, Calif.) into Sƒ9 cells. The Sƒ9 cell culture supernatant was harvested three days post-transfection. The recombinant virus-containing supernatant was serially diluted in Hink's TNM-FH insect medium (JRH Biosciences, Kansas City) supplemented Grace's salts and with 4.1 mM L-Gln, 3.3 g/L LAH, 3.3 g/L ultrafiltered yeastolate and 10% heat-inactivated fetal bovine serum (hereinafter "insect medium") and plaque assayed for recombinant plaques. After four days, recombinant plaques were selected and harvested into 1 ml of insect medium for amplification. Each 1 ml volume of recombinant baculovirus (at passage 0) was used to infect a separate T25 flask containing 2×10$^6$ Sƒ9 cells in 5 ml of insect medium. After five days of incubation at 27° C., supernatant medium was harvested from each of the T25 infections for use as passage 1 inoculum. Two of the seven recombinant baculoviral clones were then chosen for a second round of amplification, using 1 ml of passage 1 stock to infect 1×10$^8$ cells in 100 ml of insect medium divided into 2 T175 flasks. Forty-eight hours post infection, passage 2 medium from each 100 m1 prep was harvested and plaque assayed for titer. The cell pellets from the second round of amplification were assayed by affinity binding as described below to verify recombinant receptor expression. A third round of amplification was then initiated using an M.O.I. of 0.1 to infect a liter of Sƒ9 cells. Forty hours post-infection the supernatant medium was harvested to yield passage 3 baculoviral stock and the cell pellet assayed for affinity binding. Titer of the passage 3 baculoviral stock was determined by plaque assay and an M.O.I. and Incubation Time Course experiment was carried out to determine conditions for optimal receptor expression. Results from the receptor optimization experiment show that an M.O.I. of 0.1 and a 72 hour incubation were the ideal infection parameters in order to achieve optimum Y5 receptor expression in up to 1 liter Sƒ9 cell infection cultures.

Log-phase Sƒ9 cells infected with recombinant baculovirus encoding the human chimeric NPY$_5$/NPY, NPY receptor designated hNPY5ΔY1IC3/ΔY1CT, above, were cultured in insect medium at 27° C. 72 hours post-infection, a sample of cell suspension was analyzed for viability by trypan blue dye exclusion, and the remaining Sƒ9 cells were harvested via centrifugation (3000 rpm/10 minutes/4° C).

Example 676

Assay For NPY5 Receptor Binding Activity

This Example illustrates the measurement of binding activity for representative compounds.

The baculovirus-infected Sƒ9 cells expressing recombinant human chimeric NPY5/NPY1 receptor, as described in Example 675, are harvested at 42–48 hours, at which time batches of 500 mL of cell suspension are pelleted by centrifugation. Each pellet is re-suspended in 30 mL of homogenization buffer (10 mM HEPES, 250 mM sucrose, 0.5 µg/mL leupeptin, 2 µg/mL Aprotinin, 200 µM PMSF and 2.5 mM EDTA, pH 7.4) and homogenized using a POLY-TRON homogenizer (setting 5 for 30 seconds). The homogenate is centrifuged at 4° C. for 10 minutes at 536×g to pellet the nuclei. The supernatant containing isolated membranes is decanted into a clean centrifuge tube, centrifuged in the same buffer at 48,000×g for 30 minutes at 4° C. and resuspended in 30 ml homogenization buffer. This centrifugation and resuspension step is repeated twice. The final pellet is re-suspended in ice cold Dulbecco's PBS containing 5 mM EDTA, and stored in frozen aliquots at ×80° C. The protein concentration of the resulting membrane preparation (P2 preparation) is measured using the Bradford protein assay (Bio-Rad Laboratories, Hercules, Calif.). By this measure, a 1-liter culture of cells typically yields 50–75 mg of total membrane protein.

Purified P2 membranes are thawed, centrifuged and washed by PBS and re-suspended by Dounce homogenization (tight pestle) in binding buffer (50 mM Tris(HCl), 5 mM KCl, 120 mM NaCl, 2 mM CaCl$_2$, 1mM MgCl$_2$, 0.1% bovine serum albumin (BSA), pH 7.4). For competition analysis, membranes (5–50kg) are added to polypropylene tubes containing 0.050 nM [$^{125}$I]PYY(porcine) and 2tl test compound in DMSO (1 μM-4μM final concentration). For saturation binding analysis, membranes (5–50 μg) are added to polypropylene tubes containing 0.010–0.500nM [$^{125}$I] pYY (porcine; New England Nuclear Corp., Boston, Mass.). Nonspecific binding is determined in the presence of 1 μM NPY (human; American Peptide Co., Sunnyvale, Calif.) and accounts for less than 10% of total binding. Following a 2-hour incubation at room temperature, the reaction is terminated by rapid vacuum filtration. Samples are filtered over presoaked (in 1.0% polyethyleneimine for 2 hours prior to use) GF/C WHATMAN filters and rinsed 2 times with 5 mL cold binding buffer without BSA. Remaining bound radioactivity is measured by gamma counting. $K_i$ and Hill coefficient ("nH") are determined by fitting the Hill equation to the measured values with the aid of SIGMAPLOT software (SPSS Inc., Chicago). The binding affinity for compounds provided herein, expressed as a Ki value, ranges from about 0.1 nanomolar to about 10 micromolar. The most active of these compounds have a Ki of less than 100 nanomolar.

Example 677

Calcium Mobilization Assay for Determining NPY5 Receptor Modulation

This Example illustrates a representative assay for evaluating the effect of compounds on NPY5 receptor signal transduction.

Bowes Melanoma cells stably transfected with an expression vector encoding the NPY5/NPY1 chimeric receptor described above are plated at a density of 26,000 cells/well in FALCON black-walled, clear-bottomed 96-well plates (#3904, BECTON-DICKINSON, Franklin Lakes, N.J.) and grown to confluency, approximately 24 hours. The culture medium is emptied from the 96 well plate, and Fluo-3 calcium sensitive dye (Molecular Probes, Eugene, Oreg.) is added to each well (dye solution: 1 mg FLUO-3 AM, 440 μL DMSO and 440 μL 20% pluronic acid in DMSO, diluted 1:2, 50 μL diluted solution per well). Plates are covered with aluminum foil and incubated at 37° C. for 1–2 hours. After the incubation, the dye solution is emptied from the plates, cells are washed once in 100 μl KRH buffer (0.05 mM KCl, 0.115 M NaCl, 9.6 mM NaH$_2$PO$_4$, 0.01 mM MgSO$_4$, 25 mM HEPES, pH 7.4) to remove excess dye. After washing, 80 μl KRH buffer with carbachol/Thomae (KRH buffer containing 1 mM carbachol, 10 micromolar BIBP 3226 (Sigma RBI, St. Louis Mo.)) is added to each well. Assay plates are incubated in the dark, 20 minutes.

To measure the ability of a test compound to antagonize the response of cells expressing NPY5 receptor to NPY, the EC$_{50}$ of NPY is first determined. An additional 20 μl of KRH/Thomae buffer and 1 μl DMSO is added to each well of cells, prepared as described above. 100 μl human NPY in KRH/Thomae buffer is automatically transferred by the FLIPR instrument to each well. An 8-point concentration response curve, with final NPY concentrations of 1 nM to 3 μM, is used to determine NPY EC$_{50}$.

Test compounds are dissolved in 1 μl DMSO, diluted in 20 μl KRH buffer with carbachol/Thomae, and added to cells prepared as described above. The 96 well plates containing prepared cells and test compounds are incubated in the dark, at room temperature for 0.5–6 hours. It is important that the incubation not continue beyond 6 hours. Just prior to determining the fluorescence response, 100 μl human NPY diluted in KRH/Thomae buffer to 2×EC$_{50}$ is automatically added by the FLIPR instrument to each well of the 96 well plate for a final sample volume of 200 μl and a final NPY concentration of EC$_{50}$. The final concentration of test compounds in the assay wells is between 1 μM and 5 μM. Typically, cells exposed to one EC$_{50}$ of NPY exhibit a fluorescence response of about 10,000 Relative Fluorescence Units. Antagonists of the NPY5 receptor exhibit a response that is significantly less than that of the control cells to the p≦0.05 level, as measured using a parametric test of statistical significance. Typically, antagonists of the NPY5 receptor decrease the fluorescence response relative to control cells by about 20%, preferably by about 50%, and most preferably by at least 80% as compared to matched control.

Example 678

Antagonism of Bovine Pancreatic Polypeptide-Induced Food Intake

This Example illustrates the use of representative compounds to decrease food intake.

Male Sprague-Dawley rats aged 7 weeks are maintained under controlled temperature (23±3° C.), humidity (55±15%) and light-dark cycle (7:00–19:00 light on). Rats are housed individually with ad libitum access to food and water.

Rats are anesthetized with sodium pentobarbital (50 mg/kg, i.p.). A permanent stainless steel guide cannula for intracerebroventricular (ICV) injection (21 gauge, 10 mm long) is stereotaxically implanted into the right lateral ventricle. The stereotaxic coordinates used are as follows: 0.9 mm posterior and 1.2 mm lateral to the bregma and 0.5 mm ventral to the brain surface.

Animals are allowed to recover at least 6 days postoperatively before the start of the feeding experiment. The day before the experiment, animals are handled and undergo mock injection, and nocturnal food intake is measured. Rats that eat more than 15 g during the night before the experiment are used for the BPP feeding antagonism experiment.

Test compounds are suspended in 0.5% methylcellulose and orally administered by gavage. Administration of test compounds usually begins at 10:00. Dosing volume is about 5 ml/kg. One hour after administration of the test compound, bovine pancreatic polypeptide (Bovine PP 5 μg 10 μl/1 min.) is injected ICV through a stainless steel injector (26 gauge) attached to a 50 μl Hamilton microsyringe by polyethylene tubing. Bovine PP is dissolved in 10 mM PBS containing 0.05% BSA. Two hour post-injection food intake is measured for each rat.

Test compounds that reduce food intake two hours post-injection relative to food intake of control animals (animals inject with Bovine PP but not a test compound) are identified as compounds that antagonize bovine PP induced feeding.

Example 679

Food Deprivation Model

This Example illustrates the use of representative NPY5 modulators to decrease food intake within a food deprivation model.

Experimentally naive and experienced male Sprague-Dawley rats (Sasco, St. Louis, Mo.) weighing 210–300g at the beginning of the experiment are used. Animals are triple-housed in stainless steel hanging cages in a temperature (22° C.±2°) and humidity (40–70% RH) controlled animal facility with a 12:12 hour light-dark cycle. Food (Standard Rat Chow, PMI Feeds Inc., #5012) and water are available ad libitum.

Consumption data is collected while the animals were housed in Nalgene Metabolic cages (Model #650-0100). Each cage is comprised of subassemblies made of clear polymethylpentene (PMP), polycarbonate (PC), or stainless steel (SS). All parts disassemble for quick and accurate data collection and for cleaning. The entire cylinder-shaped plastic and SS cage rests on a SS stand and houses one animal.

The animal is contained in the round Upper Chamber (PC) assembly (12 cm high and 20 cm in diameter) and rests on a SS floor. Two subassemblies are attached to the Upper Chamber. The first assembly consists of a SS feeding chamber (10 cm long, 5 cm high and 5 cm wide) with a PC feeding drawer attached to the bottom. The feeding drawer has two compartments: a food storage compartment with the capacity for approximately 50 g of pulverized rat chow, and a food spillage compartment. The animal is allowed access to the pulverized chow by an opening in the SS floor of the feeding chamber. The floor of the feeding chamber does not allow access to the food dropped into the spillage compartment. The second assembly includes a water bottle support, a PC water bottle (100 ml capacity) and a graduated water spillage collection tube. The water bottle support funnels any spilled water into the water spillage collection tube.

The lower chamber consists of a PMP separating cone, PMP collection funnel, PMP fluid (urine) collection tube, and a PMP solid (feces) collection tube. The separating cone is attached to the top of the collection funnel, which in turn is attached to the bottom of the Upper Chamber. The urine runs off the separating cone onto the walls of the collection funnel and into the urine collection tube. The separating cone also separates the feces and funnels it into the feces collection tube. Food consumption, water consumption, and body weight were measured with an Ohaus Portable Advanced scale (±0.1 g accuracy).

Prior to the day of testing, animals were habituated to the testing apparatus by placing each animal in a Metabolic cage for 1 hour. On the day of the experiment, animals that were food deprived the previous night were weighed and assigned to treatment groups. Assignments were made using a quasi-random method utilizing the body weights to assure that the treatment groups had similar average body weight. Animals were then administered either vehicle (0.5% methyl cellulose, MC) or NPY5 modulator. At that time, the feeding drawer filled with pulverized chow, the filled water bottle, and the empty urine and feces collection tubes were weighed. Two hours after modulator treatment, each animal is weighed and placed in a Metabolic Cage. Following a one hour test session, animals are removed and body weight obtained. The food and water containers are then weighed and the data recorded.

NPY5 modulators (suspended in 0.5% MC) or 0.5% MC are administered orally (PO) using a gavage tube connected to a 3 or 5 ml syringe at a volume of 10 ml/kg. Each modulator was made into a homogenous suspension by stirring and ultrasonicating for at least 1 hour prior to dosing.

The means and standard errors of the mean (SEM) for food consumption, water consumption, and body weight change are presented. One-way analysis of variance using Systat (5.2.1) was used to test for group differences. A significant effect is defined as having a p value of <0.05.

The following parameters are defined: Body weight change is the difference between the body weight of the animal immediately prior to placement in the metabolic cage and its body weight at the end of the one hour test session. Food consumption is the difference in the weight of the food drawer prior to testing and the weight following the 1 hour test session. Water consumption is the difference in the weight of the water bottle prior to testing and the weight following the 1 hour test session. The most potent compounds of the invention significantly reduce food intake and body weight gain.

Description Of The Sequence Listing

SEQ ID NO: 1 is a 5' human NPY5 receptor primer

SEQ ID NO: 2 is a 3' human NPY5 receptor primer

SEQ ID NO: 3 is human NPY1 receptor

SEQ ID NO: 4 is NPY1 amino acid sequence

SEQ ID NO: 5 is the chimeric DNA sequence designated hNPY5ΔY1IC3

SEQ ID NO: 6 is human NPY5 receptor nucleotide sequence

SEQ ID NO: 7 is human NPY5 receptor amino acid sequence

SEQ ID NO: 8 is nucleotides 903–964 of human NPY5 receptor

SEQ ID NO: 9 is amino acids 236–256 of human NPY5 receptor

SEQ ID NO: 10 is the HY1L3S sense oligo

SEQ ID NO: 11 is HY1L3AS antisense oligo

SEQ ID NO: 12 is the chimeric DNA sequence designated hNPY5ΔY1CT

SEQ ID NO: 13 is primer HY1R1

SEQ ID NO: 14 is primer HY5R1

SEQ ID NO: 15 is forward primer corresponding to bases 527–551 of human Y5 receptor SEQ ID NO: 16 is the chimeric DNA sequence designated hNPY5ΔY1IC3/ΔY1CT SEQ ID NO: 17 is amino acid sequence of the chimeric receptor hNPY5ΔY1IC3/ΔY1CT From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound of Formula I:

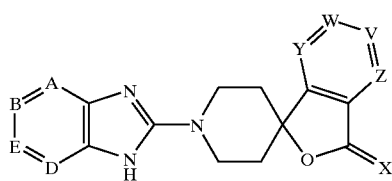

Formula I or a pharmaceutically acceptable salt or prodrug thereof, wherein:

X is oxygen or $H_2$;

A, D, V, W, Y and Z are independently N or $CR_1$;

B is $CR_2$;

E is $CR_3$;

$R_1$ is independently selected at each occurrence from:
(i) hydrogen, halogen, hydroxy, amino, nitro, cyano, —C(=O)NH$_2$ and —COOH; and
(ii) L-R$_A$-Q-G, wherein:
L is a bond, —O—, —C(=O)—, —OC(=O)—, —C(=O)O—, —O—C(=O)O—, —S(O)$_n$—, —NR$_B$—, —C(=O)NHR$_B$—, —NHR$_B$C(=O)—, —NR$_B$S(O)$_n$— or —S(O)$_n$NR$_B$—;
n is independently chosen at each occurrence from 0, 1 or 2;
R$_A$ is (C$_1$–C$_8$)alkyl, (C$_2$–C$_8$)alkenyl, (C$_2$–C$_8$) alkynyl, (C$_3$–C$_8$)cycloalkyl, (C$_3$–C$_8$)cycloalkenyl, (C$_3$–C$_8$)cycloalkynyl, quinazoline, pyridine, oxazole, pyrazine, piperazinyl, pyrimidinyl, morpholinyl each of which is optionally substituted with from 1 to 5 substituents independently selected from hydroxy, halogen, amino, cyano, nitro, (C$_1$–C$_6$)alkyl and halo(C$_1$–C$_6$)alkyl;
Q is a bond, —O—, —C(=O)—, —OC(=O)—, —C(=O)O—, —O—C(=O)O—, —S(O)$_n$—, —CHR$_B$—, —NR$_B$—, —C(=O)NHR$_B$—, —NHR$_B$C(=O)—, —NR$_B$S(O)$_n$— or —S(O)$_n$NR$_B$—;
R$_B$ is independently selected at each occurrence from hydrogen, (C$_1$–C$_8$)alkyl, (C$_3$–C$_8$)cyclOalkyl, (C$_3$–C$_8$)cycloalkyl(C$_1$–C$_8$)alkyl and (C$_1$–C$_8$)alkyl(C$_3$–C$_8$)cycloalkyl; and
G is: hydrogen; or
(C$_1$–C$_8$)alkyl, (C$_2$–C$_8$)alkenyl, (C$_2$–C$_8$)alkynyl, (C$_3$–C$_8$)cycloalkyl(C$_1$–C$_8$)alkyl, or a 3- to 10-membered carbocyclic, quinazoline, pyridine, oxazole, pyrazine, piperazinyl, pyrimidinyl, morpholinyl, each of which is optionally substituted with from 1 to 5 substituents independently selected from hydroxy, halogen, amino, cyano, nitro, (C$_1$–C$_8$)alkyl, halo(C$_1$–C$_8$)alkyl, (C$_1$–C$_8$)alkoxy, —NH (C$_1$–C$_8$)alkyl, —N((C$_1$–C$_8$)alkyl)$_2$, NHC (=O)(C$_1$–C$_8$)alkyl, —N(C$_1$–C$_8$)alkylC(=O) (alkyl), —NHS(O)$_s$(C$_1$–C$_8$)alkyl, S(O)$_s$ (C$_1$–C$_8$)alkyl, —S(O)$_s$NH(C$_1$–C$_8$)alkyl and —S(O)$_s$N((C$_1$–C$_8$)alkyl)$_2$, wherein s is 0, 1 or 2;

R$_2$ and R$_3$ are independently selected at each occurrence from:
(i) hydrogen, halogen, hydroxy, amino, nitro, cyano, —C(=O)NH$_2$ and —COOH; and
(ii) T-R$_C$-U-M, wherein:
T is a bond, —O—, —C(=O)—, —OC(=O)—, —C(=O)O—, —O—C(=O)O—, —S(O)$_n$—, —NR$_D$—, —C(O)NHR$_D$—, —NHR$_D$C(=O)—, —NR$_D$S(O)$_n$— or —S(O)$_n$NR$_D$—;
n is independently chosen at each occurrence from 0, 1 or 2;
R$_C$ is (C$_1$–C$_8$)alkyl, (C$_2$–C$_8$)alkenyl, (C$_2$–C$_8$)alkynyl or a 3- to 10-membered carbo cyclic, quinazoline, pyridine, oxazole, pyrazine, piperazinyl, pyrimidinyl, morpholinyl, each of which is optionally substituted with from 1 to 5 substituents independently selected from hydroxy, halogen, amino, cyano, nitro, (C$_1$–C$_6$)alkyl and halo(C$_1$–C$_6$)alkyl;
U is a bond, —O—, —C(=O)—, —OC(=O)—, —C(=O)O—, —O—C(=O)O—, —S(O)$_n$—, —CHR$_D$—, —NR$_D$—, —C(=O)NHR$_D$—, —NHR$_D$C(=O)—, —NR$_D$S(O)$_n$— or —S(O)$_n$NR$_D$—;

R$_D$ is independently selected at each occurrence from hydrogen, (C$_1$–C$_8$)alkyl, (C$_3$–C$_8$)cycloalkyl, (C$_3$–C$_8$)cycloalkyl(C$_1$–C$_8$)alkyl and (C$_1$–C$_8$)alkyl (C$_3$–C$_8$)cycloalkyl; and M is: hydrogen; or (C$_1$–C$_8$)alkyl, (C$_2$–C$_8$)alkenyl, (C$_2$–C$_8$) alkynyl or a 3- to 10-membered carbocyclic, quinazoline, pyridine, oxazole, pyrazine, piperazinyl, pyrimidinyl, morpholinyl, each of which is optionally substituted with from 1 to 5 substituents independently selected from hydroxy, halogen, amino, cyano, nitro, (C$_1$–C$_8$) alkyl, halo (C$_1$–C$_8$)alkyl, (C$_1$–C$_8$)alkoxy, —NH(C$_1$–C$_8$) alkyl, —N((C$_1$–C$_8$)alkyl)$_2$, NHC(=O)(C$_1$–C$_8$) alkyl, —N(C$_1$–C$_8$)alkyl C(=O)(alkyl), —NHS (O)$_s$(C$_1$–C$_8$)alkyl, —S(O)$_s$(C$_1$–C$_8$)alkkyl, —S(O)$_s$NH($_1$–C$_8$)alkyl and —S(O)$_s$N((C$_1$–C$_8$) alkyl)$_2$, wherein s is 0, 1 or 2.

2. A compound according to claim 1, wherein Y and Z are both CH, and V and W are both CR$_1$.

3. A compound according to claim 2, wherein V, W, Y and Z are all CH.

4. A compound according to claim 1, wherein A and D are each independently selected from CH and C-halogen.

5. A compound according to claim 1, wherein A and D are both CR$_1$, B is CR$_2$ and E is CR$_3$.

6. A compound according to claim 1, wherein R$_1$ is independently selected at each occurrence from hydrogen, halogen, hydroxy, nitro, cyano, amino, (C$_1$–C$_6$)alkyl, (C$_1$–C$_6$)alkoxy, (C$_1$–C$_6$)alkoxy substituted with amino, mono- or di-(C$_1$–C$_6$)alkylamino or (C$_1$–C$_6$)alkoxy, (C$_3$–C$_7$) cycloalkyl, (C$_3$–C$_7$)cycloalkyl(C$_1$–C$_4$)alkyl, (C$_2$–C$_6$) alkenyl, (C$_3$–C$_7$)cycloalkenyl, (C$_2$–C$_6$)alkynyl, (C$_3$–C$_7$) cycloalkynyl, halo(C$_1$–C$_6$)alkyl, halo(C$_1$–C$_6$)alkoxy, mono and di(C$_1$–C$_6$)alkylamino, amino(C$_1$–C$_6$)alkyl, and mono- and di(C$_1$–C$_6$)alkylamino(C$_1$–C$_6$)alkyl.

7. A compound according to claim 6, wherein:

T is a bond, —O—, —C(=O)—, —OC(=O)—, —C(=O)O—, —S(O)$_n$— or —NR$_D$—;

U is a bond, —O—, —C(=O)—, —OC(=O)—, —C(=O)O—, —S(O)$_n$—, —CHR$_D$ or —NR$_D$—, and M is hydrogen; or (C$_1$–C$_6$)alkyl, (C$_2$–C$_6$)alkenyl, (C$_2$–C$_6$)alkynyl, or a 3- to 10-membered carbocyclic, quinazoline, pyridine, oxazole, pyrazine, piperazinyl, pyrimidinyl, morpholinyl, each of which is optionally independently substituted with from 1 to 5 substituents selected from hydroxy, halogen, amino, cyano, nitro, (C$_1$–C$_6$)alkyl, halo(C$_1$–C$_6$) alkyl, (C$_1$–C$_6$)alkoxy, —NH(C$_1$–C$_6$)alkyl and —N((C$_1$–C$_6$) alkyl)$_2$.

8. A compound according to claim 1, wherein R$_1$ is independently selected at each occurrence from hydrogen, methyl, ethyl, methoxy, ethoxy, trifluoromethyl, trifluoromethoxy and difluoromethoxy.

9. A compound according to claim 6, wherein R$_2$ and R$_3$ are independently selected from:

(i) hydrogen and halogen; and (ii) T-R$_C$, wherein T is a bond, —O—, —C(=O)—, —OC(=O)—, —C(=O)O— or —S(O)$_2$—; and R$_C$ is (C$_1$–C$_6$)alkyl or a 5- to 6-membered carbocyclic, quinazoline, pyridine, oxazole, pyrazine, piperazinyl, pyrimidinyl, morpholinyl, each of which is optionally substituted with from 1 to 3 substituents independently selected from hydroxyl, halogen, cyano, (C$_1$–C$_6$)alkyl and halo(C$_1$–C$_6$)alkyl.

10. A compound according to claim 1, wherein Q is a bond, —O— or —NR$_B$—.

11. A compound according to claim 1, wherein G is hydrogen or (C$_1$–C$_6$) alkyl, (C$_2$–C$_6$)alkenyl, (C$_2$–C$_6$) alkynyl, (C$_5$–C$_7$)cycloalkyl, (C$_5$–C$_7$)cycloalkyl(C$_1$–C$_6$) alkyl, quinazoline, pyridine, oxazole, pyrazine, piperazinyl, pyrimidinyl, morpholinyl, each of which is optionally substituted with from 1 to 5 substituents independently selected from hydroxy, (C$_1$–C$_6$)alkyl, (C$_1$–C$_6$)alkoxy, halogen, amino, cyano and nitro.

12. A compound according to claim 1, wherein:

R$_D$ is independently selected at each occurrence from hydrogen, (C$_1$–C$_6$)alkyl and (C$_5$–C$_7$)cycloalkyl;

U is a bond, —O—, —C(=O)—, —CHR$_D$— or —NR$_D$—; and

M is: hydrogen; or (C$_1$–C$_6$)alkyl, (C$_2$–C$_6$)alkenyl, (C$_2$–C$_6$)alkynyl or a 3- to 10-membered carbocyclic, quinazoline, pyridine, oxazole, pyrazine, piperazinyl, pyrimidinyl, morpholinyl, each of which is optionally substituted with from 1 to 5 substituents independently selected from hydroxy, halogen, amino, cyano, nitro, (C$_1$–C$_6$) alkyl, halo(C$_1$–C$_6$)alkyl, (C$_1$–C$_6$)alkoxy and halo (C$_1$–C$_6$)alkoxy.

13. A compound according to claim 1, wherein at least two of V, W, Y and Z are CR$_1$, and wherein:

L is a bond, —O—, —C(=O)—, —OC(=O)—, —C(=O)O— or —NR$_B$—;

R$_B$ is hydrogen, (C$_1$–C$_8$)alkyl or (C$_3$–C$_8$)cycloalkyl;

Q is a bond; and

G is hydrogen.

14. A compound according to claim 1, wherein R$_C$ is selected from phenyl, oxazolyl, piperazinyl, pyrimidinyl, pyrazinyl, and morpholinyl, each of which is substituted with from 0 to 2 substituents independently selected from hydroxy, halogen, amino, cyano, nitro, (C$_1$–C$_6$)alkyl, halo (C$_1$–C$_6$)alkyl, (C$_1$–C$_6$)alkoxy and halo(C$_1$–C$_6$)alkoxy.

15. A compound according to claim 6, wherein R$_2$ and R$_3$ are independently selected at each occurrence from:

trifluoromethoxy, trifluoromethyl, trifluorosulfonyl, hydrogen, halogen, hydroxy, nitro, cyano, amino, haloalkyl, and —COOH; and benzoyl, benzhydryl, phenoxy, benzyloxy, phenyl, oxazolyl, piperazinyl, pyrimidinyl, pyrazinyl, and morpholinyl, each of which is substituted with from 0 to 2 substituents independently selected from hydroxy, halogen, amino, cyano, nitro, (C$_1$–C$_6$)alkyl, halo(C$_1$–C$_6$)alkyl, (C$_1$–C$_6$)alkoxy and halo(C$_1$–C$_6$) alkoxy.

16. A compound according to claim 6, wherein:

R$_1$ is independently selected at each occurrence from hydrogen, hydroxy, halogen, (C$_1$–C$_6$)alkyl, halo (C$_1$–C$_6$)alkyl, (C$_1$–C$_6$)alkoxy and halo(C$_1$–C$_6$)alkoxy;

R$_2$ is selected from hydrogen, hydroxy, halogen, (C$_1$–C$_6$) alkyl, halo(C$_1$–C$_6$) alkyl, (C$_1$–C$_6$)alkoxy and halo (C$_1$–C$_6$)alkoxy; and R$_3$ is selected from hydroxy, halogen, cyano, and (C$_1$–C$_6$) alkyl, (C$_5$–C$_7$) cycloalkyl, halo(C$_1$–C$_6$)alkyl, (C$_1$–C$_6$) alkoxy, halo(C$_1$–C$_6$)alkoxy, (C$_1$–C$_6$)alkanoyl, (C$_1$–C$_6$) alkanoyloxy, (C$_1$–C$_6$)alkoxycarbonyl, (C$_1$–C$_6$) alkylaminocarbonyl, (C$_1$–C$_6$) carbamate, (C$_1$–C$_6$) alkylsulfonyl, oxazolyl, pyridinyl, pyrazinyl, phenyl, benzyl, phenoxy, benzyloxy and benzoyl, wherein each is optionally substituted with from 1 to 3 substituents independently selected from hydroxy, halogen, (C$_1$–C$_6$)alkyl, halo(C$_1$–C$_6$) alkyl, (C$_1$–C$_6$)alkoxy and halo(C$_1$–C$_6$) alkoxy.

17. A compound according to claim 6, wherein:

$R_1$ is independently selected at each occurrence from hydrogen, hydroxy, halogen, $(C_1-C_6)$alkyl, halo$(C_1-C_6)$alkyl, $(C_1-C_6)$alkoxy and halo$(C_1-C_6)$alkoxy;

$R_2$ is selected from hydroxy, halogen, cyano, and $(C_1-C_6)$ alkyl, $(C_5-C_7)$ cycloalkyl, halo$(C_1-C_6)$alkyl, $(C_1-C_6)$ alkoxy, halo$(C_1-C_6)$alkoxy, $(C_1-C_6)$alkanoyl, $(C_1-C_6)$ alkanoyloxy, $(C_1-C_6)$alkoxycarbonyl, $(C_1-C_6)$ alkylaminocarbonyl, $(C_1-C_6)$ carbamate, $(C_1-C_6)$ lkylsulfonyl, oxazolyl, pyrimidinyl, pyridinyl, pyrazinyl, phenyl, benzyl, phenoxy, benzyloxy and benzoyl, wherein each is optionally substituted with from 1 to 3 substituents independently selected from hydroxy, halogen, $(C_1-C_6)$alkyl, halo$(C_1-C_6)$ alkyl, $(C_1-C_6)$ alkoxy and halo$(C_1-C_6)$alkoxy; and $R_3$ is selected from hydrogen, hydroxy, halogen, $(C_1-C_6)$ alkyl, halo$(C_1-C_6)$ alkyl, $(C_1-C_6)$alkoxy and halo$(C_1-C_6)$alkoxy.

18. A compound according to claim 1, wherein:

V, W, Y and Z are all $CR_1$, and $R_1$ is independently selected at each occurrence from hydrogen, halogen, $(C_1-C_6)$alkyl, halo$(C_1-C_6)$alkyl and $(C_1-C_6)$alkoxy;

A and D are $CR_1$, wherein $R_1$ is independently selected at each occurrence from hydrogen, halogen, $(C_1-C_6)$ alkyl, halo$(C_1-C_6)$alkyl and $(C_1-C_6)$alkoxy; and B and E are $CR_2$ and $CR_3$, respectively, wherein $R_2$ and $R_3$ are independently selected from:
(i) hydrogen, halogen and cyano; and
(ii) $(C_1-C_6)$alkyl, $(C_3-C_7)$cycloalkyl, halo$(C_1-C_6)$ alkyl, $(C_1-C_6)$alkoxy, halo$(C_1-C_6)$alkoxy, $(C_1-C_6)$ alkanoyl, $(C_1-C_6)$alkoxycarbonyl, $(C_1-C_6)$ alkylaminocarbonyl, $(C_1-C_6)$alkylsulfonyl, oxazolyl, pyrimidinyl, pyridinyl, pyrazinyl, phenyl, benzyl, phenoxy, benzyloxy and benzoyl, wherein each is optionally substituted with 1 to 3 substituents selected from halogen and $(C_1-C_6)$alkyl.

19. A compound according to claim 1, wherein the compound is selected from:

1'-(7-chloro-1H-benzimidazol-2-yl)-spiro[isobenzofuran-1,4'-piperidin]-3-one;

1'-(1H-benzimidazol-2-yl)-spiro[isobenzofuran-1,4'-piperidin]-3-one;

1'-(5-n-propylsulfonyl-1H benzimidazol-2-yl) spiro [isobenzofuran-1,4'-piperidin]-3-one;

1'-(5-cyano-1H-benzimidazol-2-yl)-spiro[isobenzofuran-1,4'-piperidin]-3-one;

1'-(5-acetyl-1H-benzimidazol-2-yl)-spiro[isobenzofuran-1,4'-piperidin]-3-one;

1'-(5-carboxy-1H-benzimidazol-2-yl)-spiro [isobenzofuran-1,4'-piperidin]-3-one, methyl ester;

1'-(5'pyrazin-2-yl-1H-benzimidazol-2-yl)-spiro [isobenzofuran-1,4'-pipendin]-3-one;

1'-(5'pyridin-3-yl-1H-benzimidazol-2-yl)-spiro [isobenzofuran-1,4'-piperidin]-3-one;

1'-(5-trifluoromethoxy-1H-benzimidazol-2-yl)-spiro [isobenzofuran-1,4'-piperidin]-3-one;

1'-(5-methyl-1H-benzimidazol-2-yl)-spiro [isobenzofuran-1,4'-piperidin]-3-one;

1'-(5-benzoyl-1H-benzimidazol-2-yl)-spiro [isobenzofuran-1,4'-piperidin]-3-one;

1'-(5-methoxy-1H-benzimidazol-2-yl)-spiro [isobenzofuran-1,4'-piperidin]-3-one;

1'-(5-chloro-1H-benzimidazol-2-yl)-spiro[isobenzofuran-1,4'-piperidin]-3-one;

1'-(5-fluoro-1H-benzimidazol-2-yl)-spiro[isobenzofuran-1,4'-piperidin]-3-one;

1'-(5-methyl-1H-benzimidazol-2-yl)-spiro [isobenzofuran-1,4'-piperidin]-3-one;

1'-(5-methylsulfonyl-1H-benzimidazol-2-yl)-spiro [isobenzofuran-1,4'-piperidin]-3-one;

1'-(5-oxazol-2-yl-1H-benzimidazol-2-yl)-spiro [isobenzofuran-1,4'-piperidin]-3-one;

1'-(5,6-difluoro-1H-benzimidazol-2-yl)-spiro [isobenzofuran-1,4'-piperidin]-3-one;

1'-(5-trifluoromethyl-1H-benzimidazol-2-yl)-spiro [isobenzofuran-1,4'-piperidin]-3-one;

1'-(5,7-dichloro-1H-benzimidazol-2-yl)-spiro [isobenzofuran-1,4'-piperidin]-3-one;

1'-(5,6-dimethoxy-1H-benzimidazol-2-yl)-spiro [isobenzofuran-1,4'-piperidin]-3-one;

1'-(5-trifluoromethylsulfonyl-1H-benzimidazol-2-yl)-spiro[isobenzofuran-1,4'-piperidin]-3-one;

1'-(5-(3,5-dimethyl-isoxazol-4-yl)-1H-benzimidazol-2-yl)-spiro[isobenzofuran-1,4'-piperidin]-3-one;

1'-(5-ethoxy-1H-benzimidazol-2-yl)-spiro [isobenzofuran-1,4'-piperidin]-3-one; and.

20. A compound according to claim 1, wherein the compound exhibits a $K_i$ of 1 micromolar or less in an NPY5 receptor ligand binding assay.

21. A compound according to claim 1, wherein the compound exhibits a $K_i$ of 100 nanomolar or less in an NPY5 receptor ligand binding assay.

22. A compound according to claim 1, wherein the compound exhibits a $K_i$ of 10 nanomolar or less in an NPY5 receptor ligand binding assay.

23. A pharmaceutical composition comprising a compound according to claim 1, in combination with a physiologically acceptable carrier or excipient.

* * * * *

SEQUENCE LISTING

<160> NUMBER OF SEQ ID NOS: 17

<210> SEQ ID NO 1
<211> LENGTH: 21
<212> TYPE: DNA
<213> ORGANISM: Artificial Sequence
<220> FEATURE:
<223> OTHER INFORMATION: HUMAN NPY5 RECEPTOR PRIMER - 5'

<400> SEQUENCE: 1
ttttggttgc tgacaaatgt c                                         21

<210> SEQ ID NO 2
<211> LENGTH: 26
<212> TYPE: DNA
<213> ORGANISM: Artificial Sequence
<220> FEATURE:
<223> OTHER INFORMATION: HUMAN NPY5 RECEPTOR PRIMER - 3'

<400> SEQUENCE: 2
ccttggtaaa cagtgagaat tattac                                    26

<210> SEQ ID NO 3
<211> LENGTH: 1605
<212> TYPE: DNA
<213> ORGANISM: Homo sapiens

<400> SEQUENCE: 3
ccttctttaa tgaagcagga gcgaaaaaga caaattccaa agaggattgt tcagttcaag    60
ggaatgaaga attcagaata attttggtaa atggattcca atatgggaa taagaataag    120
ctgaacagtt gacctgcttt gaagaaacat actgtccatt tgtctaaaat aatctataac    180
aaccaaacca atcaaaatga attcaacatt attttcccag gttgaaaatc attcagtcca    240
ctctaatttc tcagagaaga atgcccagct tctggctttt gaaaatgatg attgtcatct    300
gcccttggcc atgatattta ccttagctct tgcttatgga gctgtgatca ttcttggtgt    360
ctctggaaac ctggccttga tcataatcat cttgaaacaa aaggagatga gaaatgttac    420
caacatcctg attgtgaacc tttccttctc agacttgctt gttgccatca tgtgtctccc    480
ctttacattt gtctacacat taatggacca ctgggtcttt ggtgaggcga tgtgtaagtt    540
gaatccttt gtgcaatgtg tttcaatcac tgtgtccatt ttctctctgg ttctcattgc    600
tgtggaacga catcagctga taatcaaccc tcgagggtgg agaccaaata atagacatgc    660
ttatgtaggt attgctgtga tttgggtcct tgctgtggct tcttctttgc ctttcctgat    720
ctaccaagta atgactgatg agccgttcca aaatgtaaca cttgatgcgt acaaagacaa    780
atacgtgtgc tttgatcaat ttccatcgga ctctcatagg ttgtcttata ccactctcct    840
cttggtgctg cagtattttg gtccactttg ttttatattt atttgctact tcaagatata    900
tatacgccta aaaggagaa acaacatgat ggacaagatg agagacaata agtacaggtc    960
cagtgaaacc aaaagaatca atatcatgct gctctccatt gtggtagcat ttgcagtctg   1020
ctggctccct cttaccatct ttaacactgt gtttgattgg aatcatcaga tcattgctac   1080
ctgcaaccac aatctgttat tcctgctctg ccacctcaca gcaatgatat ccacttgtgt   1140
caacccaata tttatggggt tcctgaacaa aaacttccag agagacttgc agttcttctt   1200
caacttttgt gatttccggt ctcgggatga tgattatgaa acaatagcca tgtccacgat   1260
gcacacagat gtttccaaaa cttctttgaa gcaagcaagc ccagtcgcat ttaaaaaaat   1320

-continued

```
caacaacaat gatgataatg aaaaaatctg aaactactta tagcctatgg tcccggatga    1380
catctgttta aaaacaagca caacctgcaa catactttga ttacctgttc tcccaaggaa    1440
tggggttgaa atcatttgaa aatgactaag attttcttgt cttgcttttt actgcttttg    1500
ttgtagttgt cataattaca tttggaacaa aaggtgtggg ctttggggtc ttctggaaat    1560
agttttgacc agacatcttt gaagtgcttt ttgtgaattt accag                   1605
```

<210> SEQ ID NO 4
<211> LENGTH: 384
<212> TYPE: PRT
<213> ORGANISM: homosapiens

<400> SEQUENCE: 4

```
Met Asn Ser Thr Leu Phe Ser Gln Val Glu Asn His Ser Val His Ser
1               5                   10                  15

Asn Phe Ser Glu Lys Asn Ala Gln Leu Leu Ala Phe Glu Asn Asp Asp
            20                  25                  30

Cys His Leu Pro Leu Ala Met Ile Phe Thr Leu Ala Leu Ala Tyr Gly
        35                  40                  45

Ala Val Ile Ile Leu Gly Val Ser Gly Asn Leu Ala Leu Ile Ile Ile
    50                  55                  60

Ile Leu Lys Gln Lys Glu Met Arg Asn Val Thr Asn Ile Leu Ile Val
65                  70                  75                  80

Asn Leu Ser Phe Ser Asp Leu Leu Val Ala Ile Met Cys Leu Pro Phe
                85                  90                  95

Thr Phe Val Tyr Thr Leu Met Asp His Trp Val Phe Gly Glu Ala Met
            100                 105                 110

Cys Lys Leu Asn Pro Phe Val Gln Cys Val Ser Ile Thr Val Ser Ile
        115                 120                 125

Phe Ser Leu Val Leu Ile Ala Val Glu Arg His Gln Leu Ile Ile Asn
    130                 135                 140

Pro Arg Gly Trp Arg Pro Asn Asn Arg His Ala Tyr Val Gly Ile Ala
145                 150                 155                 160

Val Ile Trp Val Leu Ala Val Ala Ser Ser Leu Pro Phe Leu Ile Tyr
                165                 170                 175

Gln Val Met Thr Asp Glu Pro Phe Gln Asn Val Thr Leu Asp Ala Tyr
            180                 185                 190

Lys Asp Lys Tyr Val Cys Phe Asp Gln Phe Pro Ser Asp Ser His Arg
        195                 200                 205

Leu Ser Tyr Thr Thr Leu Leu Leu Val Leu Gln Tyr Phe Gly Pro Leu
    210                 215                 220

Cys Phe Ile Phe Ile Cys Tyr Phe Lys Ile Tyr Ile Arg Leu Lys Arg
225                 230                 235                 240

Arg Asn Asn Met Met Asp Lys Met Arg Asp Asn Lys Tyr Arg Ser Ser
                245                 250                 255

Glu Thr Lys Arg Ile Asn Ile Met Leu Leu Ser Ile Val Val Ala Phe
            260                 265                 270

Ala Val Cys Trp Leu Pro Leu Thr Ile Phe Asn Thr Val Phe Asp Trp
        275                 280                 285

Asn His Gln Ile Ile Ala Thr Cys Asn His Asn Leu Leu Phe Leu Leu
    290                 295                 300

Cys His Leu Thr Ala Met Ile Ser Thr Cys Val Asn Pro Ile Phe Tyr
305                 310                 315                 320
```

```
Gly Phe Leu Asn Lys Asn Phe Gln Arg Asp Leu Gln Phe Phe Asn
            325                 330                 335

Phe Cys Asp Phe Arg Ser Arg Asp Asp Tyr Glu Thr Ile Ala Met
            340                 345                 350

Ser Thr Met His Thr Asp Val Ser Lys Thr Ser Leu Lys Gln Ala Ser
            355                 360                 365

Pro Val Ala Phe Lys Lys Ile Asn Asn Asp Asp Asn Glu Lys Ile
            370                 375             380
```

<210> SEQ ID NO 5
<211> LENGTH: 1069
<212> TYPE: DNA
<213> ORGANISM: Artificial Sequence
<220> FEATURE:
<223> OTHER INFORMATION: Y5/Y1 CHIMERA

<400> SEQUENCE: 5

| | | | | | |
|---|---|---|---|---|---|
| ttttggttgc | tgacaaatgt | cttttattc | caagcaggac | tataatatgg | atttagagct | 60 |
| cgacgagtat | tataacaaga | cacttgccac | agagaataat | actgctgcca | ctcggaattc | 120 |
| tgatttccca | gtctgggatg | actataaaag | cagtgtagat | gacttacagt | attttctgat | 180 |
| tgggctctat | acatttgtaa | gtcttcttgg | ctttatgggg | aatctactta | ttttaatggc | 240 |
| tctcatgaaa | aagcgtaatc | agaagactac | ggtaaacttc | ctcataggca | atctggcctt | 300 |
| ttctgatatc | ttggttgtgc | tgttttgctc | acctttcaca | ctgacgtctg | tcttgctgga | 360 |
| tcagtggatg | tttggcaaag | tcatgtgcca | tattatgcct | tttcttcaat | gtgtgtcagt | 420 |
| tttggtttca | actttaattt | taatatcaat | tgccattgtc | aggtatcata | tgataaaaca | 480 |
| tcccatatct | aataatttaa | cagcaaacca | tggctacttt | ctgatagcta | ctgtctggac | 540 |
| actaggtttt | gccatctgtt | ctccccttcc | agtgtttcac | agtcttgtgg | aacttcaaga | 600 |
| aacatttggt | tcagcattgc | tgagcagcag | gtatttatgt | gttgagtcat | ggccatctga | 660 |
| ttcatacaga | attgccttta | ctatctcttt | attgctagtt | cagtatattc | tgcccttagt | 720 |
| ttgtcttact | gtaagtcata | caagtgtctg | catacgccta | aaaaggagaa | acaacatgat | 780 |
| ggacaagatg | agagacaata | agtacaggtc | cagtagatct | cgaagtgttt | tctacagact | 840 |
| gaccatactg | atattagtat | ttgctgttag | ttggatgcca | ctacaccttt | tccatgtggt | 900 |
| aactgatttt | aatgacaatc | ttatttcaaa | taggcatttc | aagttggtgt | attgcatttg | 960 |
| tcatttgttg | ggcatgatgt | cctgttgtct | taatccaatt | ctatatgggt | tcttaataa | 1020 |
| tgggattaaa | gctgatttag | tgtcccttat | acactgtctt | catatgtaa | | 1069 |

<210> SEQ ID NO 6
<211> LENGTH: 1406
<212> TYPE: DNA
<213> ORGANISM: Homo sapiens

<400> SEQUENCE: 6

| | | | | | |
|---|---|---|---|---|---|
| ttttggttgc | tgacaaatgt | cttttattc | caagcaggac | tataatatgg | atttagagct | 60 |
| cgacgagtat | tataacaaga | cacttgccac | agagaataat | actgctgcca | ctcggaattc | 120 |
| tgatttccca | gtctgggatg | actataaaag | cagtgtagat | gacttacagt | attttctgat | 180 |
| tgggctctat | acatttgtaa | gtcttcttgg | ctttatgggg | aatctactta | ttttaatggc | 240 |
| tctcatgaaa | aagcgtaatc | agaagactac | ggtaaacttc | ctcataggca | atctggcctt | 300 |
| ttctgatatc | ttggttgtgc | tgttttgctc | acctttcaca | ctgacgtctg | tcttgctgga | 360 |
| tcagtggatg | tttggcaaag | tcatgtgcca | tattatgcct | tttcttcaat | gtgtgtcagt | 420 |

```
tttggtttca actttaattt taatatcaat tgccattgtc aggtatcata tgataaaaca    480
tcccatatct aataatttaa cagcaaacca tggctacttt ctgatagcta ctgtctggac    540
actaggtttt gccatctgtt ctccccttcc agtgtttcac agtcttgtgg aacttcaaga    600
aacatttggt tcagcattgc tgagcagcag gtatttatgt gttgagtcat ggccatctga    660
ttcatacaga attgccttta ctatctcttt attgctagtt cagtatattc tgcccttagt    720
ttgtcttact gtaagtcata caagtgtctg cagaagtata agctgtggat tgtccaacaa    780
agaaaacaga cttgaagaaa atgagatgat caacttaact cttcatccat ccaaaaagag    840
tgggcctcag gtgaaactct ctggcagcca taaatggagt tattcattca tcaaaaaaca    900
cagaagaaga tatagcaaga agacagcatg tgtgttacct gctccagaaa gaccttctca    960
agagaaccac tccagaatac ttccagaaaa ctttggctct gtaagaagtc agctctcttc   1020
atccagtaag ttcataccag gggtccccac ttgctttgag ataaaacctg aagaaaattc   1080
agatgttcat gaattgagag taaaacgttc tgttacaaga ataaaaaaga gatctcgaag   1140
tgttttctac agactgacca tactgatatt agtatttgct gttagttgga tgccactaca   1200
ccttttccat gtggtaactg attttaatga caatcttatt tcaaataggc atttcaagtt   1260
ggtgtattgc atttgtcatt tgttgggcat gatgtcctgt tgtcttaatc caattctata   1320
tgggtttctt aataatggga ttaaagctga tttagtgtcc cttatacact gtcttcatat   1380
gtaataattc tcactgttta ccaagg                                        1406
```

<210> SEQ ID NO 7
<211> LENGTH: 455
<212> TYPE: PRT
<213> ORGANISM: homosapiens

<400> SEQUENCE: 7

```
Met Ser Phe Tyr Ser Lys Gln Asp Tyr Asn Met Asp Leu Glu Leu Asp
1               5                   10                  15

Glu Tyr Tyr Asn Lys Thr Leu Ala Thr Glu Asn Asn Thr Ala Ala Thr
            20                  25                  30

Arg Asn Ser Asp Phe Pro Val Trp Asp Asp Tyr Lys Ser Ser Val Asp
        35                  40                  45

Asp Leu Gln Tyr Phe Leu Ile Gly Leu Tyr Thr Phe Val Ser Leu Leu
    50                  55                  60

Gly Phe Met Gly Asn Leu Leu Ile Leu Met Ala Leu Met Lys Lys Arg
65                  70                  75                  80

Asn Gln Lys Thr Thr Val Asn Phe Leu Ile Gly Asn Leu Ala Phe Ser
                85                  90                  95

Asp Ile Leu Val Val Leu Phe Cys Ser Pro Phe Thr Leu Thr Ser Val
            100                 105                 110

Leu Leu Asp Gln Trp Met Phe Gly Lys Val Met Cys His Ile Met Pro
        115                 120                 125

Phe Leu Gln Cys Val Ser Val Leu Val Ser Thr Leu Ile Leu Ile Ser
    130                 135                 140

Ile Ala Ile Val Arg Tyr His Met Ile Lys His Pro Ile Ser Asn Asn
145                 150                 155                 160

Leu Thr Ala Asn His Gly Tyr Phe Leu Ile Ala Thr Val Trp Thr Leu
                165                 170                 175

Gly Phe Ala Ile Cys Ser Pro Leu Pro Val Phe His Ser Leu Val Glu
            180                 185                 190
```

```
Leu Gln Glu Thr Phe Gly Ser Ala Leu Leu Ser Ser Arg Tyr Leu Cys
            195                 200                 205

Val Glu Ser Trp Pro Ser Asp Ser Tyr Arg Ile Ala Phe Thr Ile Ser
    210                 215                 220

Leu Leu Leu Val Gln Tyr Ile Leu Pro Leu Val Cys Leu Thr Val Ser
225                 230                 235                 240

His Thr Ser Val Cys Arg Ser Ile Ser Cys Gly Leu Ser Asn Lys Glu
            245                 250                 255

Asn Arg Leu Glu Glu Asn Glu Met Ile Asn Leu Thr Leu His Pro Ser
            260                 265                 270

Lys Lys Ser Gly Pro Gln Val Lys Leu Ser Gly Ser His Lys Trp Ser
            275                 280                 285

Tyr Ser Phe Ile Lys Lys His Arg Arg Arg Tyr Ser Lys Lys Thr Ala
    290                 295                 300

Cys Val Leu Pro Ala Pro Glu Arg Pro Ser Gln Glu Asn His Ser Arg
305                 310                 315                 320

Ile Leu Pro Glu Asn Phe Gly Ser Val Arg Ser Gln Leu Ser Ser Ser
            325                 330                 335

Ser Lys Phe Ile Pro Gly Val Pro Thr Cys Phe Glu Ile Lys Pro Glu
            340                 345                 350

Glu Asn Ser Asp Val His Glu Leu Arg Val Lys Arg Ser Val Thr Arg
            355                 360                 365

Ile Lys Lys Arg Ser Arg Ser Val Phe Tyr Arg Leu Thr Ile Leu Ile
    370                 375                 380

Leu Val Phe Ala Val Ser Trp Met Pro Leu His Leu Phe His Val Val
385                 390                 395                 400

Thr Asp Phe Asn Asp Asn Leu Ile Ser Asn Arg His Phe Lys Leu Val
            405                 410                 415

Tyr Cys Ile Cys His Leu Leu Gly Met Met Ser Cys Cys Leu Asn Pro
            420                 425                 430

Ile Leu Tyr Gly Phe Leu Asn Asn Gly Ile Lys Ala Asp Leu Val Ser
            435                 440                 445

Leu Ile His Cys Leu His Met
    450                 455

<210> SEQ ID NO 8
<211> LENGTH: 62
<212> TYPE: DNA
<213> ORGANISM: Artificial Sequence
<220> FEATURE:
<223> OTHER INFORMATION: HUMAN NPY5 NUCLEOTIDES 903-964

<400> SEQUENCE: 8
tacgcctaaa aaggagaaac aacatgatgg acaagatgag agacaataag tacaggtcca    60
gt                                                                  62

<210> SEQ ID NO 9
<211> LENGTH: 21
<212> TYPE: PRT
<213> ORGANISM: Artificial Sequence
<220> FEATURE:
<223> OTHER INFORMATION: HUMAN NPY5 AMINO ACIDS 236-256

<400> SEQUENCE: 9

Ile Arg Leu Lys Arg Arg Asn Asn Met Met Asp Lys Met Arg Asp Asn
1               5                   10                  15

Lys Tyr Arg Ser Ser
```

```
<210> SEQ ID NO 10
<211> LENGTH: 63
<212> TYPE: DNA
<213> ORGANISM: Artificial Sequence
<220> FEATURE:
<223> OTHER INFORMATION: CHIMERIC Y1/Y5 PRIMER

<400> SEQUENCE: 10
tacgcctaaa aaggagaaac aacatgatgg acaagatgag agacaataag tacaggtcca    60
gta                                                                  63

<210> SEQ ID NO 11
<211> LENGTH: 71
<212> TYPE: DNA
<213> ORGANISM: Artificial Sequence
<220> FEATURE:
<223> OTHER INFORMATION: CHIMERIC Y1/Y5 PRIMER

<400> SEQUENCE: 11
gatctactgg acctgtactt attgtctctc atcttgtcca tcatgttgtt tctccttttt    60
aggcgtatgc a                                                         71

<210> SEQ ID NO 12
<211> LENGTH: 1500
<212> TYPE: DNA
<213> ORGANISM: Artificial Sequence
<220> FEATURE:
<223> OTHER INFORMATION: Y1/Y5 CHIMERA

<400> SEQUENCE: 12
atgtcttttt attccaagca ggactataat atggatttag agctcgacga gtattataac      60
aagacacttg ccacagagaa taatactgct gccactcgga attctgattt cccagtctgg     120
gatgactata aaagcagtgt agatgactta cagtattttc tgattgggct ctatacattt     180
gtaagtcttc ttggctttat ggggaatcta cttatttaa tggctctcat gaaaaagcgt      240
aatcagaaga ctacggtaaa cttcctcata ggcaatctgg ccttttctga tatcttggtt     300
gtgctgtttt gctcaccttt cacactgacg tctgtcttgc tggatcagtg gatgtttggc     360
aaagtcatgt gccatattat gcctttcctt caatgtgtgt cagttttggt ttcaacttta     420
attttaatat caattgccat tgtcaggtat catatgataa acatcccat atctaataat      480 ttaacagcaa accatggcta ctttctgata gctactgtct ggacactagg ttttgccatc     540
tgttctcccc ttccagtgtt tcacagtctt gtggaacttc aagaaacatt tggttcagca     600
ttgctgagca gcaggtattt atgtgttgag tcatggccat ctgattcata cagaattgcc     660
tttactatct ctttattgct agttcagtat attctgccct tagtttgtct tactgtaagt     720
catacaagtg tctgcagaag tataagctgt ggattgtcca acaaagaaaa cagacttgaa     780
gaaaatgaga tgatcaactt aactcttcat ccatccaaaa agagtgggcc tcaggtgaaa     840
ctctctggca gccataaatg gagttattca ttcatcaaaa aacacagaag aagatatagc     900
aagaagacag catgtgtgtt acctgctcca gaaagacctt tcaagagaa ccactccaga     960 atacttccag aaaactttgg ctctgtaaga agtcagctct cttcatccag taagttcata    1020 ccagggtcc ccacttgctt tgagataaaa cctgaagaaa attcagatgt tcatgaattg    1080
agagtaaaac gttctgttac aagaataaaa aagagatctc gaagtgtttt ctacagactg    1140
accatactga tattagtatt tgctgttagt tggatgccac tacaccttt ccatgtggta    1200
```

```
actgatttta atgacaatct tatttcaaat aggcatttca agttggtgta ttgcatttgt    1260
catttgttgg gcatgatgtc ctgttgtctt aatccaattc tatatgggtt tcttaataat    1320
ggaattcaga gagacttgca gttcttcttc aacttttgtg atttccggtc tcgggatgat    1380
gattatgaaa caatagccat gtccacgatg cacacagatg tttccaaaac ttctttgaag    1440
caagcaagcc cagtcgcatt taaaaaaatc aacaacaatg atgataatga aaaaatctga    1500
```

<210> SEQ ID NO 13
<211> LENGTH: 31
<212> TYPE: DNA
<213> ORGANISM: Artificial Sequence
<220> FEATURE:
<223> OTHER INFORMATION: MUTAGENIC R1 PRIMER

<400> SEQUENCE: 13

```
gaacaaaaga attcagagag acttgcagtt c                                    31
```

<210> SEQ ID NO 14
<211> LENGTH: 28
<212> TYPE: DNA
<213> ORGANISM: Artificial Sequence
<220> FEATURE:
<223> OTHER INFORMATION: MUTAGENIC R1 PRIMER

<400> SEQUENCE: 14

```
cagcttgaat tccattatta agaaaccc                                        28
```

<210> SEQ ID NO 15
<211> LENGTH: 25
<212> TYPE: DNA
<213> ORGANISM: Artificial Sequence
<220> FEATURE:
<223> OTHER INFORMATION: HUMAN NPY5 PRIMER

<400> SEQUENCE: 15

```
gctactgtct ggacactagg ttttg                                           25
```

<210> SEQ ID NO 16
<211> LENGTH: 1201
<212> TYPE: DNA
<213> ORGANISM: Artificial Sequence
<220> FEATURE:
<223> OTHER INFORMATION: Y5/Y1 CHIMERA

<400> SEQUENCE: 16

```
ttttggttgc tgacaaatgt cttttattc caagcaggac tataatatgg atttagagct      60
cgacgagtat tataacaaga cacttgccac agagaataat actgctgcca ctcggaattc     120
tgatttccca gtctgggatg actataaaag cagtgtagat gacttacagt attttctgat    180
tgggctctat acatttgtaa gtcttcttgg ctttatgggg aatctactta ttttaatggc    240
tctcatgaaa aagcgtaatc agaagactac ggtaaacttc ctcataggca atctggcctt     300
ttctgatatc ttggttgtgc tgttttgctc acctttcaca ctgacgtctg tcttgctgga     360
tcagtggatg tttggcaaag tcatgtgcca tattatgcct tttcttcaat gtgtgtcagt     420 tttggttca actttaatttt taatatcaat tgccattgtc aggtatcata tgataaaaca     480
tcccatatct aataatttaa cagcaaacca tggctacttt ctgatagcta ctgtctggac     540
actaggtttt gccatctgtt ctccccttcc agtgtttcac agtcttgtgg aacttcaaga     600
aacatttggt tcagcattgc tgagcagcag gtatttatgt gttgagtcat ggccatctga     660
```

-continued

```
ttcatacaga attgccttta ctatctcttt attgctagtt cagtatattc tgcccttagt      720
ttgtcttact gtaagtcata caagtgtctg catacgccta aaaggagaaa acaacatgat      780
ggacaagatg agagacaata agtacaggtc cagtagatct cgaagtgttt tctacagact      840
gaccatactg atattagtat ttgctgttag ttggatgcca ctacaccttt tccatgtggt      900
aactgatttt aatgacaatc ttatttcaaa taggcatttc aagttggtgt attgcatttg      960
tcatttgttg ggcatgatgt cctgttgtct taatccaatt ctatatgggt ttcttaataa     1020
tggaattcag agagacttgc agttcttctt caacttttgt gatttccggt ctcgggatga     1080
tgattatgaa acaatagcca tgtccacgat gcacacagat gtttccaaaa cttctttgaa     1140
gcaagcaagc ccagtcgcat ttaaaaaaat caacaacaat gatgataatg aaaaaatctg     1200
a                                                                    1201
```

<210> SEQ ID NO 17
<211> LENGTH: 394
<212> TYPE: PRT
<213> ORGANISM: Artificial Sequence
<220> FEATURE:
<223> OTHER INFORMATION: Y5/Y1 CHIMERA

<400> SEQUENCE: 17

```
Met Ser Phe Tyr Ser Lys Gln Asp Tyr Asn Met Asp Leu Glu Leu Asp
1               5                   10                  15

Glu Tyr Tyr Asn Lys Thr Leu Ala Thr Glu Asn Asn Thr Ala Ala Thr
            20                  25                  30

Arg Asn Ser Asp Phe Pro Val Trp Asp Asp Tyr Lys Ser Ser Val Asp
        35                  40                  45

Asp Leu Gln Tyr Phe Leu Ile Gly Leu Tyr Thr Phe Val Ser Leu Leu
    50                  55                  60

Gly Phe Met Gly Asn Leu Leu Ile Leu Met Ala Leu Met Lys Lys Arg
65                  70                  75                  80

Asn Gln Lys Thr Thr Val Asn Phe Leu Ile Gly Asn Leu Ala Phe Ser
                85                  90                  95

Asp Ile Leu Val Val Leu Phe Cys Ser Pro Phe Thr Leu Thr Ser Val
            100                 105                 110

Leu Leu Asp Gln Trp Met Phe Gly Lys Val Met Cys His Ile Met Pro
        115                 120                 125

Phe Leu Gln Cys Val Ser Val Leu Val Ser Thr Leu Ile Leu Ile Ser
    130                 135                 140

Ile Ala Ile Val Arg Tyr His Met Ile Lys His Pro Ile Ser Asn Asn
145                 150                 155                 160

Leu Thr Ala Asn His Gly Tyr Phe Leu Ile Ala Thr Val Trp Thr Leu
                165                 170                 175

Gly Phe Ala Ile Cys Ser Pro Leu Pro Val Phe His Ser Leu Val Glu
            180                 185                 190

Leu Gln Glu Thr Phe Gly Ser Ala Leu Leu Ser Ser Arg Tyr Leu Cys
        195                 200                 205

Val Glu Ser Trp Pro Ser Asp Ser Tyr Arg Ile Ala Phe Thr Ile Ser
    210                 215                 220

Leu Leu Leu Val Gln Tyr Ile Leu Pro Leu Val Cys Leu Thr Val Ser
225                 230                 235                 240

His Thr Ser Val Cys Ile Arg Leu Lys Arg Arg Asn Asn Met Met Asp
                245                 250                 255

Lys Met Arg Asp Asn Lys Tyr Arg Ser Ser Arg Ser Arg Ser Val Phe
```

-continued

```
                          260                 265                 270
Tyr Arg Leu Thr Ile Leu Ile Leu Val Phe Ala Val Ser Trp Met Pro
        275                 280                 285
Leu His Leu Phe His Val Val Thr Asp Phe Asn Asp Asn Leu Ile Ser
    290                 295                 300
Asn Arg His Phe Lys Leu Val Tyr Cys Ile Cys His Leu Leu Gly Met
305                 310                 315                 320
Met Ser Cys Cys Leu Asn Pro Ile Leu Tyr Gly Phe Leu Asn Asn Gly
                325                 330                 335
Ile Gln Arg Asp Leu Gln Phe Phe Phe Asn Phe Cys Asp Phe Arg Ser
            340                 345                 350
Arg Asp Asp Asp Tyr Glu Thr Ile Ala Met Ser Thr Met His Thr Asp
        355                 360                 365
Val Ser Lys Thr Ser Leu Lys Gln Ala Ser Pro Val Ala Phe Lys Lys
        370                 375                 380
Ile Asn Asn Asn Asp Asp Asn Glu Lys Ile
385                 390
```